(12) United States Patent
Sorge et al.

(10) Patent No.: US 6,946,273 B1
(45) Date of Patent: Sep. 20, 2005

(54) COMPOSITIONS AND METHODS UTILIZING DNA POLYMERASES

(75) Inventors: Joseph A. Sorge, Wilson, WY (US); Holly Hurlbut Hogrefe, San Diego, CA (US); Connie Jo Hansen, San Diego, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 09/698,341

(22) Filed: Oct. 27, 2000

Related U.S. Application Data

(60) Provisional application No. 60/162,600, filed on Oct. 29, 1999.

(51) Int. Cl.[7] .............................. C12N 9/12; C07K 1/00
(52) U.S. Cl. ....................... 435/194; 435/183; 530/350; 536/23.2; 424/94.5
(58) Field of Search ................................ 435/194, 183; 530/350; 536/23.2

(56) References Cited

U.S. PATENT DOCUMENTS

| | | | |
|---|---|---|---|
| 5,674,679 A | 10/1997 | Fuller | 435/6 |
| 5,882,904 A * | 3/1999 | Riedl et al. | 435/91.2 |

FOREIGN PATENT DOCUMENTS

| | | | |
|---|---|---|---|
| EP | 0655506 A1 | 5/1995 | C12Q/1/68 |
| EP | 0727496 A2 | 8/1996 | C12Q/1/68 |
| WO | WO 97/39150 | 10/1997 | |
| WO | WO 99/06538 | 2/1999 | |

OTHER PUBLICATIONS

Dong et al., Mutational Studies of Human DNA Polymerase alpha, Journal of Biological Chemistry, vol. 268, No. 15, pp. 24163–24174, 1993.*
Stryer, Biochemistry, Third Edition, 1988, W.H. Freeman and Co., New York, p. 72.*
International Search Report of International Application No. PCT/US02/20562.
Gardner and Jack, *Nucleic Acids Research*, 1999, vol., 27, No. 12 2545–2553.

* cited by examiner

*Primary Examiner*—Richard Hutson
(74) *Attorney, Agent, or Firm*—Kathleen M. Williams; Palmer & Dodge, LLP

(57) ABSTRACT

The invention features a novel isolated Family B DNA polymerase, a *Thermococcus* polymerase JDF-3, and mutant recombinant forms thereof. Mutant polymerases of the invention are deficient in 3' to 5' exonuclease activity and/or exhibit reduced discrimination against non-conventional nucleotides relative to the wild-type form of the polymerase.

25 Claims, 20 Drawing Sheets

```
ATGATCCTTGACGTTGATTACATCACCGAGAATGGAAAGCCCGTCATCAGGGTCTTCAAGAAGGAGAACGGC
GAGTTCAGGATTGAATACGACCGCGAGTTCGAGCCCTACTTCTACGCGCTCCTCAGGGACGACTCTGCCATC
GAAGAAATCAAAAAGATAACCGCGGAGAGGCACGGCAGGGTCGTTAAGGTTAAGCGCGCGGAGAAGGTGAAG
AAAAAGTTCCTCGGCAGGTCTGTGGAGGTCTGGGTCCTCTACTTCACGCACCCGCAGGACGTTCCGGCAATC
CGCGACAAAATAAGGAAGCACCCCGCGGTCATCGACATCTACGAGTACGACATACCCTTCGCCAAGCGCTAC
CTCATAGACAAGGGCCTAATCCCGATGGAAGGTGAGGAAGAGCTTAAACTCATGTCCTTCGACATCGAGACG
CTCTACCACGAGGGAGAAGAGTTTGGAACCGGGCCGATTCTGATGATAAGCTACGCCGATGAAAGCGAGGCG
CGCGTGATAACCTGGAAGAAGATCGACCTTCCTTACGTTGAGGTTGTCTCCACCGAGAAGGAGATGATTAAG
CGCTTCTTGAGGGTCGTTAAGGAGAAGGACCCGGACGTGCTGATAACATACAACGGCGACAACTTCGACTTC
GCCTACCTGAAAAAGCGCTGTGAGAAGCTTGGCGTGAGCTTTACCCTCGGGAGGGACGGGAGCGAGCCGAAG
ATACAGCGCATGGGGGACAGGTTTGCGGTCGAGGTGAAGGGCAGGGTACACTTCGACCTTTATCCAGTCATA
AGGCGCACCATAAACCTCCCGACCTACACCCTTGAGGCTGTATACGAGGCGGTTTTCGGCAAGCCCAAGGAG
AAGGTCTACGCCGAGGAGATAGCCACCGCCTGGGAGACCGGCGAGGGGCTTGAGAGGGTCGCGCGCTACTCG
ATGGAGGACGCGAGGGTTACCTACGAGCTTGGCAGGGAGTTCTTCCCGATGGAGGCCCAGCTTTCCAGGCTC
ATCGGCCAAGGCCTCTGGGACGTTTCCCGCTCCAGCACCGGCAACCTCGTCGAGTGGTTCCTCCTAAGGAAG
GCCTACGAGAGGAACGAACTCGCTCCCAACAAGCCCGACGAGAGGGAGCTGGCGAGGAGAAGGGGGGGCTAC
gcCGGTGGCTACGTCAAGGAGCCGGAGCGGGGACTGTGGGACAATATCGTGTATCTAGACTTTCGTAGTCTC
TACCCTTCAATCATAATCACCCACAACGTCTCGCCAGATACGCTCAACCGCGAGGGGTGTAGGAGCTACGAC
GTTGCCCCCGAGGTCGGTCACAAGTTCTGCAAGGACTTCCCCGGCTTCATTCCGAGCCTGCTCGGAAACCTG
CTGGAGGAAAGGCAGAAGATAAAGAGGAAGATGAAGGCAACTCTCGACCCGCTGGAGAAGAATCTCCTCGAT
TACAGGCAACGCGCCATCAAGATTCTCGCCAACAGCTACTACGGCTACTACGGCTATGCCAGGGCAAGATGG
TACTGCAGGGAGTGCGCCGAGAGCGTTACGGCATGGGGAAGGGAGTACATCGAAATGGTCATCAGAGAGCTT
GAGGAAAAGTTCGGTTTTAAAGTCCTCTATGCAGACACAGACGGTCTCCATGCCACCATTCCTGGAGCGGAC
GCTGAAACAGTCAAGAAAAAGGCAATGGAGTTCTTAAACTATATCAATCCCAAACTGCCCGGCCTTCTCGAA
CTCGAATACGAGGGCTTCTACGTCAGGGGCTTCTTCGTCACGAAGAAAAAGTACGCGGTCATCGACGAGGAG
GGCAAGATAACCACGCGCGGGCTTGAGATAGTCAGGCGCGACTGGAGCGAGATAGCGAAGGAGACGCAGGCG
AGGGTTTTGGAGGCGATACTCAGGCACGGTGACGTTGAAGAGGCCGTCAGAATTGTCAGGGAAGTCACCGAA
AAGCTGAGCAAGTACGAGGTTCCGCCGGAGAAGCTGGTTATCCACGAGCAGATAACGCGCGAGCTCAAGGAC
TACAAGGCCACCGGCCCGCACGTAGCCATAGCCGAAgcGTTTGGCCGCCAGAGGTGTTAAAATCCGGCCCGGA
ACTGTGATAAGCTACATCGTTCTGAAGGGCTCCGGAAGGATAGGCGACAGGGCGATTCCCTTCGACGAGTTC
GACCCGACGAAGCACAAGTACGATGCGGACTACTACATCGAGAACCAGGTTCTGCCGGCAGTTGAGAGAATC
CTCAGGGCCTTCGGCTACCGCAAGGAAGACCTGCGCTACCAGAAGACGAGGCAGGTCGGGCTTGGCGCGTGG
CTGAAGCCGAAGGGGAAGAAGAAGTGA
```

FIG. 1

MILDVDYITENGKPVIRVFKKENGEFRIEYDREFEPYFYALLRDDSAIEEIKKITAERHGRVVKVKRAEKVK
KKFLGRSVEVWVLYFTHPQDVPAIRDKIRKHPAVIDIYEYDIPFAKRYLIDKGLIPMEGEEELKLMSFDIET
LYHEGEEFGTGPILMISYADESEARVITWKKIDLPYVEVVSTEKEMIKRFLRVVKEKDPDVLITYNGDNFDF
AYLKKRCEKLGVSFTLGRDGSEPKIQRMGDRFAVEVKGRVHFDLYPVIRRTINLPTYTLEAVYEAVFGKPKE
KVYAEEIATAWETGEGLERVARYSMEDARVTYELGREFFPMEAQLSRLIGQGLWDVSRSSTGNLVEWFLLRK
AYERNELAPNKPDERELARRRGGYAGGYVKEPERGLWDNIVYLDFRSLYPSIIITHNVSPDTLNREGCRSYD
VAPEVGHKFCKDFPGFIPSLLGNLLEERQKIKRKMKATLDPLEKNLLDYRQRAIKILANSYYGYYGYARARW
YCRECAESVTAWGREYIEMVIRELEEKFGFKVLYADTDGLHATIPGADAETVKKKAMEFLNYINPKLPGLLE
LEYEGFYVRGFFVTKKKYAVIDEEGKITTRGLEIVRRDWSEIAKETQARVLEAILRHGDVEEAVRIVREVTE
KLSKYEVPPEKLVIHEQITRELKDYKATGPHVAIAKRLAARGVKIRPGTVISYIVLKGSGRIGDRAIPFDEF
DPTKHKYDADYYIENQVLPAVERILRAFGYRKEDLRYQKTRQVGLGAWLKPKGKKK

FIG. 2

```
MILDVDYITENGKPVIRVFKKENGEFRIEYDREFEPYFYALLRDDSAIEE
IKKITAERHGRVVKVKRAEKVKKKFLGRSVEVWVLYFTHPQDVPAIRDKI
RKHPAVIDIYEYDIPFAKRYLIDKGLIPMEGEEELKLMSFDIETLYHEGE
EFGTGPILMISYADESEARVITWKKIDLPYVEVVSTEKEMIKRFLRVVKE
KDPDVLITYNGDNFDFAYLKKRCEKLGVSFTLGRDGSEPKIQRMGDRFAV      Extein 1
EVKGRVHFDLYPVIRRTINLPTYTLEAVYEAVFGKPKEKVYAEEIATAWE
TGEGLERVARYSMEDARVTYELGREFFPMEAQLSRLIGQGLWDVSRSSTG
NLVEWFLLRKAYERNELAPNKPDERELARRRGGYAGGYVKEPERGLWDNI
VYLDFRSLYPSIIITHNVSPDTLNREGCRSYDVAPEVGHKFCKDFPGFIP
SLLGNLLEERQKIKRKMKATLDPLEKNLLDYRQRAIKILAN SLLPGEWVA
VIEGGKLRPVRIGELVDGLMEASGERVKRDGDTEVLEVEGLYASPSTGSP
RKPAQCR*KP**GTAMPGKFTE*LSTPEGGLSVTRGHSLFAYRDASLWR*
RGRRRFKPGDLLAVPSG*PSRRGGRGSTSLNCSSNCPRRKRPTCHRHSGK
GRKNFFRGMLRTLRWIFGEEKTGGRPGATWSTLRGLGYVKLRKIGYGVVD
REGLGKVPRFYERLVEVIRYNGNRGEFIADFNALRPVLRLMMPEKELEEW     Intein 1
LVGTRNGFRIRPFIEVDWKFAKLLGYYVSEGSAGKWKNRTGGWSYSVRLY
NEDGSVLDDMERLARSSLGA*ARGELRRDFKEDGLHNLRGALRFTGREQE
GSVAYLHVP*GGPLGLP*GVLHRRRRRSPEQDGSALHQERASG*RPRPAP
ELAGRLSDKRPPRQRGLQGLRERGTALYRVPEAEERLTYSHVIPREVLEE
TSAGPSRRT*VTGNSGSWWKAGSSTRKGPVG*AGSSTGI*SSTGSRKSGR
KATRGTSTT*ALRRTRTSGGLWVPLRAQX SYYGYYGYARARWYCRECAES
VTAWGREYIEMVIRELEEKFGFKVLYADTDGLHATIPGADAETVKKKAME
FLNYINPKLPGLLELEYEGFYVRGFFVTKKKYAVIDEEGKITTRGLEIVR
RDWSEIAKETQARVLEAILRHGDVEEAVRIVREVTEKLSKYEVPPEKLVI     Extein 2
HEQITRELKDYKATGPHVAIAKRLAARGVKIRPGTVISYIVLKGSGRIGD
RAIPFDEFDPTKHKYDADYYIENQVLPAVERILRAFGYRKEDLRYQKTRQ
VGLGAWLKPKGKKK
```

FIG. 3

```
AATTCCACTGCCGTGTTTAACCTTTCCACCGTTGAACTTGAGGGTGATTT
TCTGAGCCTCCTCAATCACTTAATCGAGACCGCGGATTACCTTGAACTGG
TACACGTTCAACGATTCGGTTCTTGTAATGGTCGATACTGGGCCGTGCTG
GATTTTCTAAACGTCTCAAGAACGGCTTTCATCAACGGAAACTGCCACGT   5' untranslated sequence
CTCCGCCGTCGTGAGGGTTAAACCTGAAGTTCAAGACTTTGCAACGGAAT
GGCGAGAGAACGGCGACTACCCCAGTGGAAGAGCTTTTGAAAGCCAAAGC
CGAGCTTCAGCGAATGTGCGGTGCCCTTGTTCAAGAGTTGTGAGCCCTTG
ATTGTTGTTTTCTCCTCTTTTCTGATAACATCGATGGCGAAGTTTATTAG
TTCTCAGTTCGATAATCAGGCAGGTGTTGGTC ATGATCCTTGACGTTGAT
TACATCACCGAGAATGGAAAGCCCGTCATCAGGGTCTTCAAGAAGGAGAA
CGGCGAGTTCAGGATTGAATACGACCGCGAGTTCGAGCCCTACTTCTACG
CGCTCCTCAGGGACGACTCTGCCATCGAAGAAATCAAAAAGATAACCGCG
GAGAGGCACGGCAGGGTCGTTAAGGTTAAGCGCGCGGAGAAGGTGAAGAA
AAAGTTCCTCGGCAGGTCTGTGGAGGTCTGGGTCCTCTACTTCACGCACC
CGCAGGACGTTCCGGCAATCCGCGACAAAATAAGGAAGCACCCCGCGGTC
ATCGACATCTACGAGTACGACATACCCTTCGCCAAGCGCTACCTCATAGA
CAAGGGCCTAATCCCGATGGAAGGTGAGGAAGAGCTTAAACTCATGTCCT
TCGACATCGAGACGCTCTACCACGAGGGAGAAGAGTTTGGAACCGGGCCG
ATTCTGATGATAAGCTACGCCGATGAAAGCGAGGCGCGCGTGATAACCTG
GAAGAAGATCGACCTTCCTTACGTTGAGGTTGTCTCCACCGAGAAGGAGA
TGATTAAGCGCTTCTTGAGGGTCGTTAAGGAGAAGGACCCGGACGTGCTG
ATAACATACAACGGCGACAACTTCGACTTCGCCTACCTGAAAAAGCGCTG
TGAGAAGCTTGGCGTGAGCTTTACCCTCGGGAGGGACGGGAGCGAGCCGA   Extein 1
AGATACAGCGCATGGGGGACAGGTTTGCGGTCGAGGTGAAGGGCAGGGTA
CACTTCGACCTTTATCCAGTCATAAGGCGCACCATAAACCTCCCGACCTA
CACCCTTGAGGCTGTATACGAGGCGGTTTTCGGCAAGCCCAAGGAGAAGG
TCTACGCCGAGGAGATAGCCACCGCCTGGGAGACCGGCGAGGGGCTTGAG
AGGGTCGCGCGCTACTCGATGGAGGACGCGAGGGTTACCTACGAGCTTGG
CAGGGAGTTCTTCCCGATGGAGGCCCAGCTTTCCAGGCTCATCGGCCAAG
GCCTCTGGGACGTTTCCCGCTCCAGCACCGGCAACCTCGTCGAGTGGTTC
CTCCTAAGGAAGGCCTACGAGAGGAACGAACTCGCTCCCAACAAGCCCGA
CGAGGGGAGCTGGCGAGGAGAAGGGGGGGCTACGCCGGTGGCTACGTCA
AGGAGCCGGAGCGGGACTGTGGGACAATATCGTGTATCTAGACTTTCGT
AGTCTCTACCCTTCAATCATAATCACCCACAACGTCTCGCCAGATACGCT
CAACCGCGAGGGGTGTAGGAGCTACGACGTTGCCCCCGAGGTCGGTCACA
AGTTCTGCAAGGACTTCCCCGGCTTCATTCCGAGCCTGCTCGGAAACCTG
CTGGAGGAAAGGCAGAAGATAAAGAGGAAGATGAAGGCAACTCTCGACCC
GCTGGAGAAGAATCTCCTCGATTACAGGCAACGCGCCATCAAGATTCTCG
CCAAC
```

FIG. 4

AGCCTTCTTCCCGGGGAGTGGGTTGCGGTCATTGAAGGGGGGAAA
CTCAGGCCCGTCCGCATCGGCGAGCTGGTTGATGGACTGATGGAAGCCAG
CGGGGAGAGGGTGAAAAGAGACGGCGACACCGAGGTCCTTGAAGTCGAGG
GGCTTTACGCCTCTCCTTCGACAGGGAGTCCAAGAAAGCCCGCACAATGC
CGGTGAAAGCCGTGATAAGGCACCGCTATGCCGGGGAAGTTTACAGAATA
GCTCTCAACTCCGGAAGGAGGATTAAGCGTGACGCGCGGCCACAGCCTCT
TCGCGTACCGGGACGCGAGCTTGTGGAGGTGACGGGGGAGGAGGAGGTTC
AAGCCCGGCGACCTCCTGGCGGTGCCAAGCGGATAACCCTCCCGGAGAGG
AGGGAGAGGCTCAACATCGTTGAACTGCTCCTCGAACTGCCCGAGGAGGA

AACGGCCGACATGTCATCGACATTCCGGCAAGGGTAGAAAGAACTTCTTC
AGGGGAATGCTCAGAACCCTCCGCTGGATTTTCGGGGAGGAGAAGACCGG  Intein 1
AGGGCGGCCAGGCGCTACCTGGAGCACCTTGCGTGGGCTCGGCTACGTGA
AGCTGAGGAAAATCGGCTACGGGGTGGTTGATAGGGAGGGACTGGGAAAG
GTACCGCGCTTCTACGAGAGGCTCGTGGAGGTAATCCGCTACAACGGCAA
CAGGGGGGAGTTCATCGCCGATTTCAACGCGCTCCGCCCCGTCCTCCGCC
TGATGATGCCCGAGAAGGAGCTTGAAGAGTGGCTCGTTGGGACGAGGAAC
GGGTTCAGGATAAGGCCGTTCATAGAGGTTGATTGGAAGTTCGCAAAGCT
CCTCGGCTACTACGTGAGCGAGGGGAGCGCCGGGAAGTGGAAAAACCGGA
CCGGGGGCTGGAGCTACTCGGTGAGGCTTTACAACGAGGACGGGAGCGTT
CTCGACGACATGGAGAGACTCGCGAGGAGTTCTTTGGGGGCGTGAGCGCG
GGGGGAACTACGTCGAGATTTCAAAGAAGATGGCCTACATAATCTTCGAG
GGGCTCTGCGGTTCACCGGCCGAGAACAAGAGGGTTCCGTGGCTTATCTT
CACGTCCCCTGAGGAGGTCCGCTGGGCCTTCCTTGAGGGGTACTTCATCG
GCGACGGCGACGTTCACCCGAGCAAGATGGTTCGGCTCTCCACCAAGAGC
GAGCTTCTGGCTAACGGCCTCGTCCTGCTCCTGAACTCGCTGGGCGTCTC
AGCGATAAACGTCCGCCACGACAGCGGGGTTTACAGGGTCTACGTGAACG
AGGAACTGCCCTTTTACAGAGTACCGGAAGCGGAAGAACGCCTCACTTACT
CCCACGTCATACCGAGGGAAGTGCTGGAGGAGACTTCGGCCGGGCCTTCC
AGAAGAACATGAGTCACGGGAAATTCAGGGAGCTGGTGGAAAGCGGGGAG
CTCGACGCGGAAAGGGCCGGTAGGATAGGCTGGCTCCTCGACGGGGATAT
AGTCCTCGACAGGGTCTCGGAAGTCAGGAAGGAAAGCTACGAGGGGTACG
TCTACGACCTGAGCGTTGAGGAGGACGAGAACTTCTGGCGGGCTTTGGGT
TCCTCTACGCGCACAACNN

FIG. 4 (cont.)

```
                        AGCTACTACGGCTACTACGGCTATGCCAGGG
CAAGATGGTACTGCAGGGAGTGCGCCGAGAGCGTTACGGCATGGGGAAGG
GAGTACATCGAAATGGTCATCAGAGAGCTTGAGGAAAAGTTCGGTTTTAA
AGTCCTCTATGCAGACACAGACGGTCTCCATGCCACCATTCCTGGAGCGG
ACGCTGAAACAGTCAAGAAAAAGGCAATGGAGTTCTTAAACTATATCAAT
CCCAAACTGCCCGGCCTTCTCGAACTCGAATACGAGGGCTTCTACGTCAG
GGGCTTCTTCGTCACGAAGAAAAAGTACGCGGTCATCGACGAGGAGGGCA
AGATAACCACGCGCGGGCTTGAGATAGTCAGGCGCGACTGGAGCGAGATA
GCGAAGGAGACGCAGGCGAGGGTTTTGGAGGCGATACTCAGGCACGGTGA    Extein 2
CGTTGAAGAGGCCGTCAGAATTGTCAGGGAAGTCACCGAAAAGCTGAGCA
AGTACGAGGTTCCGCCGGAGAAGCTGGTTATCCACGAGCAGATAACGCGC
GAGCTCAAGGACTACAAGGCCACCGGCCCGCACGTAGCCATAGCGAAGCG
TTTGGCCGCCAGAGGTGTTAAAATCCGGCCCGGAACTGTGATAAGCTACA
TCGTTCTGAAGGGCTCCGGAAGGATAGGCGACAGGGCGATTCCCTTCGAC GAGTTCGACCCGACGAAGCACAAGTACGATGCGGACTACTACATCGAGAA
CCAGGTTCTGCCGGCAGTTGAGAGAATCCTCAGGGCCTTCGGCTACCGCA
AGGAAGACCTGCGCTACCAGAAGACGAGGCAGGTCGGGCTTGGCGCGTGG
CTGAAGCCGAAGGGGAAGAAGAAGTGA GGAATTATCTGGTTTCTTTTCCC
AGCATTAAATGCTTCCGACATTGCCTTATTTATGAAACTCCTGTTGTGCC
TGAGTTTGTGCCAGAAAACAGCCTGTTCTGACGGCGCTTTTTCTTGCCAG
GTCTCTTGAGTTTCGCAAGGGTCTTCTCGACCAGCTCAATGGTCTTGTCG
TCATTGTTTNNNNNNNNNNNNNNNNNNNNNNNNNCCCGGGGACTTCATACTGGC
GGTAATAGACAGGGATTCCTTCCTCAAGGACTTCCCGGGAGGCATTGGAG
TTTTTTGGTGGGGCTTTCACAGGATTTGCTCATCTTGTGGATTTCTCGTT
CGATTGAATCTGTCCACTTGAGGGTGTAGGTCGAGACGGTGGAGCGCGTA
TTCCGGGAGCGGGTCTTGAGGCTCCATTTTTCAGTCCTCCTCCGGCGAAG    3' Untranslated sequence
AAGTGGAACTCAAGCCGGGTGTTAGCTTATGTTATGTTCCCAACTCCTCC
AGCACCTCCAGGATCCCCTCAATCCCGGAACCTCGAAGCCCCTCTCGTGG
ATCTTTCTAACTTCCTCTGCCTCCGGGTTTATCCAGACCGCCCACATGCC
GGCTCTCAGCGCACCCTCGAAATCCTCCGCGTAGGTGTCGCCGATGTGGA
TTGCCTCGTCCGGCTCGACCCCGAAGCATCGAGCGGTTTTCTGAACATCT
CGGGCATCGGCTTATACGCCAGAACCTCGTCGGCGAAGAAGGTTCCCTCA
ATGTAGTCCATCAGGCCGAACCTCTCGAGGGGGGCCCGGTACCCAATTC
GCCCTATAGTGAGTCGATTACAATTCACTGGCCGTCGTTTTACAACGTCG
TGACTGGGAAAACCCTGGCGTTACCCAACTTAAGTCGCTTTGCAGCACAT
CCCCC
```

FIG. 4 (cont.)

Sequencing with Purified Mutants

```
4    1 ------------------------------------LVXNAXSTGNLVEWFLLRK
10   1 ---------------------------------VWDVSRSSTGNLVERFLLRK
13   1 ---------------------------------VWDVSRSSTGNLVEWFLLRK
16   1 ---------------------------------VWDVSRSSTGNLVEWFLLRK
18   1 ---------------------------------VWDVSRSSTGNLVEWFLLRK
19   1 ---------------------------------VWDVXRSSTGNLVEWFLLRK
28   1 ---------------------------------VWDVPRSSTGNLVEWFLLRK
34   1 ---------------------------------VWDVSRSSTGNLVEWFLLRK
41   1 ---------------------------------VWDVSRSSTGNLVEWFLLRK
33   1 ---------------------------------VWDVSRSSTGNLVEWFLLRK
48   1 ---------------------------------YWSXPXLRTGNLVEWFLLRK
55   1 -------------------------------VLGTXPRSSTGNLVEWFLLRK
64   1 ------------------------------XXXFWDVSRSSTGNLVEWFLLRK
Jdf3 301 TGEGLERVARYSMEDARVTYELGREFFPMEAQLSRLIGQGLWDVSRSSTGNLVEWFLLRK
              310       320       330       340       350       360

4    20 AYERNELAPNKPDERELARRRGGYAGGYVKEPERGLWDNIVYLDFRSLYPSIIITHNVSP
10   21 AYERNELAPNKPDERELARRRGGYAGGYVKEPERGLWDNIVYLDFRSLYPSIIITHSVSP
13   21 AYERNELAPNKPDERELARRRGGYAGGYVKEPERGLWDNIVYLDFRSLYPSIIITHNVSP
16   21 AYERNELAPNKPDERELARRRGGYAGGYVKEPERGLWDNIVYLDFRSLYPSIIITHNVSP
18   21 AYERNELAPNKPDERELARRRGGYAGGYVKEPERGLWDNIVYLDFRSLYPSIIITHNVSP
19   21 AYERNELAPNKPDERELARRRGGYAGGYVKEPERGQWDNIAYLDFRSLYPSIIITHNVSP
28   21 AYERNELAPNKPDERELARRRGGYAGGYVKEPERGLWDNIVYLDFRSLYPSIIITHNVSP
34   21 AYERNELAPNKPDERELARRRGGYAGGYVKEPERGLWDNIVYLDFRSLYPSIIITHNVSP
41   21 AYERNELAPNKPDERELARRRGGYAGGYVKEPERGPWDNIVYLDFRSLYPSIIITHNVSP
33   21 AYERNKLAPNKPDERELARRRGGYAGGYVKEPERGLWDNIVYLDFRSLYPSIIITHNVSP
48   21 AYERNELAPNKPDERELARRRGGYAGGYVKEPERGLWDNIVYLDFRSLYPSIIITHNVSP
55   22 AYERNELAPNKPDERELARRRGGYAGGYVKEPERGLWDNIVYLDFRSHYPSIIITHNVSP
64   24 AYERNELAPNKPDERELARRRGGYAGGYVKEPERGLWDNIVYLDFRSLYPSIIITHNVSP
Jdf3 361 AYERNELAPNKPDERELARRRGGYAGGYVKEPERGLWDNIVYLDFRSLYPSIIITHNVSP
              370       380       390       400       410       420
```

FIG. 14

```
4     80  DTLNREGCRSYDVAPEVGHKFCKDFPGFIPSLLGNLLEERQKIKRKMKATLDPLEKNLLD
10    81  DTLDREGCRSYDVAPEVGHKFCKDFPGFIPSLLGNLLEERQKIKRKMKATLDPLEKNLLD
13    81  DTLNREGCRSYDVAPEVGHKFCKDFPGFIPSLLGNLLEERQKIKRKMKATLDPLEKNLLD
16    81  DTLNREGCRSYDVAPEVGHKFCKDFPGFIPSLLGNLLEERQKIKMKMKATLDPLEKNLLD
18    81  DTLNREGCRSYDVAPEVGHKFCKDFPGFIPSLLGNLLEERQKIKRKMKATLDPLEKNLLD
19    81  DTLKREGCRSYDVAPEVGHKFCKDFPGFIPSLLGNLLEERQKIKRKMKATLDPLEKNLLD
28    81  DTLNREGCRSYDVAPEVGHKFCKDFPGFIPSLLGNLLEERQKIKRKMKATLDPLEKNLLD
34    81  DTLNREGCRSYXVAPEVGHKFCKDFPGFIPSLLGNLLEERQKIKRKMKATLDPLEKNLLD
41    81  DTLNREGCRSYXVAPEVGHKFCKDFPGFIPSLLGNLLEVRQKIKRKMKATLDPLEKNLLD
33    81  DTLNREGCRSYDVAPEVGHKFCKDFPGFIPSLLGNLLEERQKIKRKMKATLDPLEKNLLD
48    81  DTLNREGCRSYDVAPEVGHKFCKDFPGFIPSLLGNPLEERQKIKRKMKATLDPLEKNLLD
55    82  DTLNREGCRSYDVAPEDGHKFCKDFPGFIPSLLGNLLEERQKIKRKMKATLDPLEKNHLD
64    84  DTLNREGCRSYDVAPEVGHKFCKDFPGFIPSLLGNLLEERQKIKRKMKATLDPLEKNLLD
Jdf3  421 DTLNREGCRSYDVAPEVGHKFCKDFPGFIPSLLGNLLEERQKIKRKMKATLDPLEKNLLD
               430       440       450       460       470       480
```

FIG. 14 (cont.)

```
4     140  YRQRAIKILANSYYGYCGYARARWYCRECAESVTAWGREYIEMVIRELEEKFGFKVLYAD
10    141  YRQRAIKILANSYYGYYGYARARWYCRECAESVTAWGREYIEMVIRELEEKFGFKVLYAD
13    141  YRQRAIKILANSYYGYYGYARARWYCRECAESVTAWGREYIEMVIRELEEKFGFKVLYAD
16    141  YRQRAIKILANSYYGYYGYARARWYCRECAESVTAWGREYIEMVIRELEEKFGFKVLYAD
18    141  YRQRAIKILANNYYGYYGYARARWYCRECAESVTAWGREYIEMVIRELEEKFGFKVLYAD
19    141  YRQRAIKILANSYYGYYGYARARWYCRECAESVTAWGREYIEMVIRELEEKFGFKVLYAD
28    141  YRQRAIKILANSYYGYYGYARARWYCRECAESVTAWGREYIEMVIRELEEKFGFKVLYAD
34    141  YRQRAIKILANSYYGYYGYARARWYCRECAESVTAWGREYIEMVIRELEEKFGFKVLYAD
41    141  YRQRAIKILANSYYGYYGYARARWYCRECAESVTAWGREYIEMVIRELEEKFGFKVLYAD
33    141  YRQRAIKILANSYYGYYGYARARWYCRECAESVTAWGREYIEMVIRELEEKFGFKVLYAD
48    141  YRQRAIKILANSYYGYYGYARARWYCRECAESVTAWGREYIEMVIRELEEKFGFKVLYAD
55    142  YRQRAIKILANSYYGYYGYARARWYCRECAESVTAWGREYIEMVIRELEEKFGFKVLYAD
64    144  YRQRAIKILANSYYGNYGYARARWYCRECAESVTAWGREYIEMVIRELEEKFGFKVLYAD
Jdf3  481  YRQRAIKILANSYYGYYGYARARWYCRECAESVTAWGREYIEMVIRELEEKFGFKVLYAD
                    490       500

4     200  TDGLHATIPGADAETVKKKAMEFLNYINPKLPGLLELEYEGFYVRGFFVTKKKYAVIDEE
10    201  TDGLHATIPGADAETVKKKAMEFLNYINPKLPGLLELEYEGFYVRGFFVTKKKYAVIDEE
13    201  TDGLHATIPGADAETVKKKAMEFLNYINPKLPGLLELEYEGFYVRGFFVTKKKYAVIDEE
16    201  TDGLHATIPGADAETVKKKAMEFLNYINPKLPGLLELKYEGFYVRGFFVTKKKYAVIDEE
18    201  TDGLHATIPGADAETVKKKAMEFLNYINPKLPGLLELEYEGFYVRGFFVTKKKYAVIDEE
19    201  TDGLHATIPGADAETVKKKAMEFLNYINLKLPGLLELEYEGFYVRGFFVTKKKXAVIDEE
28    201  TDGLHATIPGADAETVKKKAMEFLNYINPKLPGLLELEYEGFYVRGPFVTKKKYAVIDEE
34    201  TDGLHATIPGADAETVKKKAMEFLNYINPKLPGLLELEYEGFYVRGFFVTKKKYAVIDEE
41    201  TDGLHATIPGADAETVKKKAMEFLNYINPKLPGLLELEYEGFYVRGFFVTKKKYAVIDEE
33    201  TDGLHATIPGADAETVKKKAMEFLNYINPKLPGLLEPEYEGFYVRGFFVTKKKYAVIDEE
48    201  TDGLHATIPGADAETVKKKAMEFLNYINPKLPGLLELEYEGFYVRGFFVTKKKYAVIDEE
55    202  TDGLHATIPGADAETVKKKAMEFLNYINPKLPGLLELEYEGFYVRGFFVTKKKYAVIDEE
64    204  TDGLHATIPGADAETVKKKAMEFLNYINPKLPGLLELEYEGFYVRGFFVTKKKYAVIDEE
Jdf3  541  TDGLHATIPGADAETVKKKAMEFLNYINPKLPGLLELEYEGFYVRGFFVTKKKYAVIDEE
                    550      560      570      580      590      600
```

FIG. 15

```
4    260 GKITTRGLEIVRRDWSEIAKETQARVLEAVLRHGDVEEAVRIVREVTEKLSKYEVPPEKL
10   261 GKITTRGLEIVRRDWSEIAKETQARVLEAILRHGDVEEAVRIVREVTEKLSKYEVPPEEL
13   261 GKITTRGLEIVRRDWSEIAKETQARVLEAILRHGDVEEAVRIVRKVTEKLSKYEVPPEKL
16   261 GKITTRGLEIVRRDWSEIAKETQARVLEAILRHGDVEEAVRIVREVTEKLSKYEVPPEKL
18   261 GKITTRGLEIVRRDWSEIAKETQARVLEAILRHDDVEEAVRIVREVTEKLSKYEVPPEKL
19   261 GKITTRGLEIVRRDWSKIAKETQARVLEAILRHGDVEEAIRIVREVTEKLSKYEVPPEKL
28   261 GKIATRGLEIVRRDWSEIAKETQARVLEAILRHGDVEEAVRIVREVTEKLSKYEVPPEKL
34   261 GKITTRGLEIVRRDWSEIAKETQARVLEAILRHGDVEEAVRIVREVTEKLNKYEVPPEKL
41   261 GKITTRGLEIVRRDWSEIAKETQARVLEAILRHGDVEEAVRIVREVTEKLSKYEVPPEKL
33   261 GKITTRGLEIVRRDWSEIAKETQARVLEAILRHGDVEEAVRIVREVTEKLSKYEVPPEKL
48   261 GKITTRGLEIVRRDWSEIAKETQARVLEAILRHGDVEEAVRIVREVTEKLSKYEVPPVKL
55   262 GKITTRGLEIVRRDWSEIAKETQARVLEAILRHGDVEEAVRIVREVTEKLSKYEVPPGEA
64   264 GKITTRGLEIVRRDWSEIAKETQARVLEAILRHGDVEEAVRIVREVTEKLSKYEVPPEKL
Jdf3 601 GKITTRGLEIVRRDWSEIAKETQARVLEAILRHGDVEEAVRIVREVTEKLSKYEVPPEKL
         610       620       630       640       650       660
```

FIG. 15 (cont.)

SEQUENCE LISTING

<160> NUMBER OF SEQ ID NOS: 48

<210> SEQ ID NO 1
<211> LENGTH: 2331
<212> TYPE: DNA
<213> ORGANISM: Thermococcus sp. JDF-3

<400> SEQUENCE: 1

```
atgatccttg acgttgatta catcaccgag aatggaaagc ccgtcatcag ggtcttcaag      60
aaggagaacg gcgagttcag gattgaatac gaccgcgagt tcgagcccta cttctacgcg     120
ctcctcaggg acgactctgc catcgaagaa atcaaaaaga taaccgcgga gaggcacggc     180
agggtcgtta aggttaagcg cgcggagaag gtgaagaaaa agttcctcgg caggtctgtg     240
gaggtctggg tcctctactt cacgcacccg caggacgttc cggcaatccg cgacaaaata     300
aggaagcacc ccgcggtcat cgacatctac gagtacgaca taccccttcgc caagcgctac     360 ctcatagaca agggcctaat cccgatggaa ggtgaggaag agcttaaact catgtccttc     420
gacatcgaga cgctctacca cgagggagaa gagtttggaa ccgggccgat tctgatgata     480
agctacgccg atgaaagcga ggcgcgcgtg ataacctgga agaagatcga ccttccttac     540
gttgaggttg tctccaccga gaaggagatg attaagcgct tcttgagggt cgttaaggag     600
aaggacccgg acgtgctgat aacatacaac ggcgacaact cgacttcgc ctacctgaaa     660 aagcgctgtg agaagcttgg cgtgagcttt accctcggga gggacgggag cgagccgaag     720
atacagcgca tgggggacag gtttgcggtc gaggtgaagg gcagggtaca cttcgaccttt     780 tatccagtca taaggcgcac cataaacctc ccgacctaca cccttgaggc tgtatacgag     840
```

-continued

```
gcggttttcg gcaagcccaa ggagaaggtc tacgccgagg agatagccac cgcctgggag      900
accggcgagg ggcttgagag ggtcgcgcgc tactcgatgg aggacgcgag ggttacctac      960
gagcttggca gggagttctt cccgatggag gcccagcttt ccaggctcat cggccaaggc     1020
ctctgggacg tttcccgctc cagcaccggc aacctcgtcg agtggttcct cctaaggaag     1080
gcctacgaga ggaacgaact cgctcccaac aagcccgacg agggagct ggcgaggaga       1140
agggggggct acgccggtgg ctacgtcaag gagccggagc ggggactgtg ggacaatatc     1200
gtgtatctag actttcgtag tctctaccct tcaatcataa tcacccacaa cgtctcgcca     1260
gatacgctca accgcgaggg gtgtaggagc tacgacgttg cccccgaggt cggtcacaag     1320
ttctgcaagg acttccccgg cttcattccg agcctgctcg aaacctgct ggaggaaagg      1380
cagaagataa agaggaagat aaggcaact ctcgacccgc tggagaagaa tctcctcgat      1440
tacaggcaac gcgccatcaa gattctcgcc aacagctact acggctacta cggctatgcc     1500
agggcaagat ggtactgcag ggagtgcgcc gagagcgtta cggcatgggg aagggagtac     1560
atcgaaatgg tcatcagaga gcttgaggaa aagttcggtt ttaaagtcct ctatgcagac     1620
acagacggtc tccatgccac cattcctgga gcggacgctg aaacagtcaa gaaaaaggca     1680
atggagttct taaactatat caatcccaaa ctgcccggcc ttctcgaact cgaatacgag     1740
ggcttctacg tcagggctt cttcgtcacg aagaaaaagt acgcggtcat cgacgaggag     1800
ggcaagataa ccacgcgcgg gcttgagata gtcaggcgcg actggagcga gatagcgaag     1860
gagacgcagg cgagggtttt ggaggcgata ctcaggcacg tgacgttga agaggccgtc      1920
agaattgtca gggaagtcac cgaaaagctg agcaagtacg aggttccgcc ggagaagctg     1980
gttatccacg agcagataac gcgcgagctc aaggactaca aggccaccgg cccgcacgta     2040
gccatagcga agcgtttggc cgccagaggt gttaaaatcc ggcccggaac tgtgataagc     2100
tacatcgttc tgaagggctc cggaaggata ggcgacaggg cgattccctt cgacgagttc     2160
gacccgacga agcacaagta cgatgcggac tactacatcg agaaccaggt tctgccggca     2220
gttgagagaa tcctcagggc cttcggctac cgcaaggaag acctgcgcta ccagaagacg     2280
aggcaggtcg ggcttggcgc gtggctgaag ccgaagggga agaagaagtg a              2331
```

<210> SEQ ID NO 2
<211> LENGTH: 776
<212> TYPE: PRT
<213> ORGANISM: Thermococcus sp. JDF-3

<400> SEQUENCE: 2

```
Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110
```

-continued

```
Asp Ile Pro Phe Ala Lys Arg Tyr Leu Ile Asp Lys Gly Leu Ile Pro
        115                 120                 125

Met Glu Gly Glu Glu Leu Lys Leu Met Ser Phe Asp Ile Glu Thr
130                 135                 140

Leu Tyr His Glu Gly Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
        210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
        290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
        450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525
```

-continued

Glu Glu Lys Phe Gly Phe Lys Val Leu Tyr Ala Asp Thr Asp Gly Leu
    530             535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
            645                 650                 655

Pro Glu Lys Leu Val Ile His Glu Gln Ile Thr Arg Glu Leu Lys Asp
        660                 665                 670

Tyr Lys Ala Thr Gly Pro His Val Ala Ile Ala Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
            725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Gly Ala Trp
    755                 760                 765

Leu Lys Pro Lys Gly Lys Lys Lys
    770                 775

<210> SEQ ID NO 3
<211> LENGTH: 1300
<212> TYPE: PRT
<213> ORGANISM: Thermococcus sp. JDF-3
<220> FEATURE:
<221> NAME/KEY: UNSURE
<222> LOCATION: (1015)..(1015)
<223> OTHER INFORMATION: X = unknown

<400> SEQUENCE: 3

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
            85                  90                  95

Arg Asp Lys Ile Arg Lys His Pro Ala Val Ile Asp Ile Tyr Glu Tyr

-continued

```
            100                 105                 110
Asp Ile Pro Phe Ala Lys Arg Tyr Leu Ile Asp Lys Gly Leu Ile Pro
            115                 120                 125
Met Glu Gly Glu Glu Leu Lys Leu Met Ser Phe Asp Ile Glu Thr
130                 135                 140
Leu Tyr His Glu Gly Glu Glu Phe Gly Thr Gly Pro Ile Leu Met Ile
145                 150                 155                 160
Ser Tyr Ala Asp Glu Ser Glu Ala Arg Val Ile Thr Trp Lys Lys Ile
                    165                 170                 175
Asp Leu Pro Tyr Val Glu Val Val Ser Thr Glu Lys Glu Met Ile Lys
                180                 185                 190
Arg Phe Leu Arg Val Val Lys Glu Lys Asp Pro Asp Val Leu Ile Thr
            195                 200                 205
Tyr Asn Gly Asp Asn Phe Asp Phe Ala Tyr Leu Lys Lys Arg Cys Glu
210                 215                 220
Lys Leu Gly Val Ser Phe Thr Leu Gly Arg Asp Gly Ser Glu Pro Lys
225                 230                 235                 240
Ile Gln Arg Met Gly Asp Arg Phe Ala Val Glu Val Lys Gly Arg Val
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
            275                 280                 285
Lys Val Tyr Ala Glu Glu Ile Ala Thr Ala Trp Glu Thr Gly Glu Gly
290                 295                 300
Leu Glu Arg Val Ala Arg Tyr Ser Met Glu Asp Ala Arg Val Thr Tyr
305                 310                 315                 320
Glu Leu Gly Arg Glu Phe Phe Pro Met Glu Ala Gln Leu Ser Arg Leu
                325                 330                 335
Ile Gly Gln Gly Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
            355                 360                 365
Pro Asn Lys Pro Asp Glu Arg Glu Leu Ala Arg Arg Arg Gly Gly Tyr
370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Arg Ser Tyr Asp
                420                 425                 430
Val Ala Pro Glu Val Gly His Lys Phe Cys Lys Asp Phe Pro Gly Phe
            435                 440                 445
Ile Pro Ser Leu Leu Gly Asn Leu Leu Glu Glu Arg Gln Lys Ile Lys
            450                 455                 460
Arg Lys Met Lys Ala Thr Leu Asp Pro Leu Glu Lys Asn Leu Leu Asp
465                 470                 475                 480
Tyr Arg Gln Arg Ala Ile Lys Ile Leu Ala Asn Ser Leu Leu Pro Gly
                485                 490                 495
Glu Trp Val Ala Val Ile Glu Gly Gly Lys Leu Arg Pro Val Arg Ile
                500                 505                 510
Gly Glu Leu Val Asp Gly Leu Met Glu Ala Ser Gly Glu Arg Val Lys
            515                 520                 525
```

-continued

```
Arg Asp Gly Asp Thr Glu Val Leu Glu Val Gly Leu Tyr Ala Ser
    530                 535                 540

Pro Ser Thr Gly Ser Pro Arg Lys Pro Ala Gln Cys Arg Lys Pro Gly
545                 550                 555                 560

Thr Ala Met Pro Gly Lys Phe Thr Glu Leu Ser Thr Pro Glu Gly Gly
                565                 570                 575

Leu Ser Val Thr Arg Gly His Ser Leu Phe Ala Tyr Arg Asp Ala Ser
            580                 585                 590

Leu Trp Arg Arg Gly Arg Arg Phe Lys Pro Gly Asp Leu Leu Ala
        595                 600                 605

Val Pro Ser Gly Pro Ser Arg Gly Gly Arg Gly Ser Thr Ser Leu
    610                 615                 620

Asn Cys Ser Ser Asn Cys Pro Arg Arg Lys Arg Pro Thr Cys His Arg
625                 630                 635                 640

His Ser Gly Lys Gly Arg Lys Asn Phe Phe Arg Gly Met Leu Arg Thr
                645                 650                 655

Leu Arg Trp Ile Phe Gly Glu Glu Lys Thr Gly Gly Arg Pro Gly Ala
            660                 665                 670

Thr Trp Ser Thr Leu Arg Gly Leu Gly Tyr Val Lys Leu Arg Lys Ile
        675                 680                 685

Gly Tyr Gly Val Val Asp Arg Glu Gly Leu Gly Lys Val Pro Arg Phe
    690                 695                 700

Tyr Glu Arg Leu Val Glu Val Ile Arg Tyr Asn Gly Asn Arg Gly Glu
705                 710                 715                 720

Phe Ile Ala Asp Phe Asn Ala Leu Arg Pro Val Leu Arg Leu Met Met
                725                 730                 735

Pro Glu Lys Glu Leu Glu Glu Trp Leu Val Gly Thr Arg Asn Gly Phe
            740                 745                 750

Arg Ile Arg Pro Phe Ile Glu Val Asp Trp Lys Phe Ala Lys Leu Leu
        755                 760                 765

Gly Tyr Tyr Val Ser Glu Gly Ser Ala Gly Lys Trp Lys Asn Arg Thr
    770                 775                 780

Gly Gly Trp Ser Tyr Ser Val Arg Leu Tyr Asn Glu Asp Gly Ser Val
785                 790                 795                 800

Leu Asp Asp Met Glu Arg Leu Ala Arg Ser Ser Leu Gly Ala Ala Arg
                805                 810                 815

Gly Glu Leu Arg Arg Asp Phe Lys Glu Asp Gly Leu His Asn Leu Arg
            820                 825                 830

Gly Ala Leu Arg Phe Thr Gly Arg Glu Gln Glu Gly Ser Val Ala Tyr
        835                 840                 845

Leu His Val Pro Gly Gly Pro Leu Gly Leu Pro Gly Val Leu His Arg
    850                 855                 860

Arg Arg Arg Arg Ser Pro Glu Gln Asp Gly Ser Ala Leu His Gln Glu
865                 870                 875                 880

Arg Ala Ser Gly Arg Pro Arg Pro Ala Pro Glu Leu Ala Gly Arg Leu
                885                 890                 895

Ser Asp Lys Arg Pro Pro Arg Gln Arg Gly Leu Gln Gly Leu Arg Glu
            900                 905                 910

Arg Gly Thr Ala Leu Tyr Arg Val Pro Glu Ala Glu Arg Leu Thr
        915                 920                 925

Tyr Ser His Val Ile Pro Arg Glu Val Leu Glu Glu Thr Ser Ala Gly
    930                 935                 940
```

```
Pro Ser Arg Arg Thr Val Thr Gly Asn Ser Gly Ser Trp Trp Lys Ala
945                 950                 955                 960

Gly Ser Ser Thr Arg Lys Gly Pro Val Gly Ala Gly Ser Ser Thr Gly
            965                 970                 975

Ile Ser Ser Thr Gly Ser Arg Lys Ser Gly Arg Lys Ala Thr Arg Gly
        980                 985                 990

Thr Ser Thr Thr Ala Leu Arg Arg  Thr Arg Thr Ser Gly  Gly Leu Trp
    995                 1000                1005

Val Pro  Leu Arg Ala Gln Xaa  Ser Tyr Tyr Gly Tyr  Tyr Gly Tyr
1010                 1015                1020

Ala Arg  Ala Arg Trp Tyr Cys  Arg Glu Cys Ala Glu  Ser Val Thr
1025                 1030                1035

Ala Trp  Gly Arg Glu Tyr Ile  Glu Met Val Ile Arg  Glu Leu Glu
1040                 1045                1050

Glu Lys  Phe Gly Phe Lys Val  Leu Tyr Ala Asp Thr  Asp Gly Leu
1055                 1060                1065

His Ala  Thr Ile Pro Gly Ala  Asp Ala Glu Thr Val  Lys Lys Lys
1070                 1075                1080

Ala Met  Glu Phe Leu Asn Tyr  Ile Asn Pro Lys Leu  Pro Gly Leu
1085                 1090                1095

Leu Glu  Leu Glu Tyr Glu Gly  Phe Tyr Val Arg Gly  Phe Phe Val
1100                 1105                1110

Thr Lys  Lys Lys Tyr Ala Val  Ile Asp Glu Glu Gly  Lys Ile Thr
1115                 1120                1125

Thr Arg  Gly Leu Glu Ile Val  Arg Arg Asp Trp Ser  Glu Ile Ala
1130                 1135                1140

Lys Glu  Thr Gln Ala Arg Val  Leu Glu Ala Ile Leu  Arg His Gly
1145                 1150                1155

Asp Val  Glu Glu Ala Val Arg  Ile Val Arg Glu Val  Thr Glu Lys
1160                 1165                1170

Leu Ser  Lys Tyr Glu Val Pro  Pro Glu Lys Leu Val  Ile His Glu
1175                 1180                1185

Gln Ile  Thr Arg Glu Leu Lys  Asp Tyr Lys Ala Thr  Gly Pro His
1190                 1195                1200

Val Ala  Ile Ala Lys Arg Leu  Ala Ala Arg Gly Val  Lys Ile Arg
1205                 1210                1215

Pro Gly  Thr Val Ile Ser Tyr  Ile Val Leu Lys Gly  Ser Gly Arg
1220                 1225                1230

Ile Gly  Asp Arg Ala Ile Pro  Phe Asp Glu Phe Asp  Pro Thr Lys
1235                 1240                1245

His Lys  Tyr Asp Ala Asp Tyr  Tyr Ile Glu Asn Gln  Val Leu Pro
1250                 1255                1260

Ala Val  Glu Arg Ile Leu Arg  Ala Phe Gly Tyr Arg  Lys Glu Asp
1265                 1270                1275

Leu Arg  Tyr Gln Lys Thr Arg  Gln Val Gly Leu Gly  Ala Trp Leu
1280                 1285                1290

Lys Pro  Lys Gly Lys Lys Lys
1295                 1300

<210> SEQ ID NO 4
<211> LENGTH: 5255
<212> TYPE: DNA
<213> ORGANISM: Thermococcus sp. JDF-3
<220> FEATURE:
<221> NAME/KEY: misc_feature
```

-continued

```
<222> LOCATION: (3518)..(3519)
<223> OTHER INFORMATION: n = unknown
<221> NAME/KEY: misc_feature
<222> LOCATION: (4560)..(4580)
<223> OTHER INFORMATION: n = unknown

<400> SEQUENCE: 4
aattccactg ccgtgtttaa cctttccacc gttgaacttg agggtgattt tctgagcctc      60
ctcaatcact taatcgagac cgcggattac cttgaactgg tacacgttca acgattcggt     120
tcttgtaatg gtcgatactg ggccgtgctg gattttctaa acgtctcaag aacggctttc     180
atcaacggaa actgccacgt ctccgccgtc gtgagggtta aacctgaagt tcaagacttt     240
gcaacggaat ggcgagagaa cggcgactac cccagtggaa gagcttttga agccaaagc      300
cgagcttcag cgaatgtgcg gtgcccttgt tcaagagttg tgagcccttg attgttgttt     360
tctcctcttt tctgataaca tcgatggcga agtttattag ttctcagttc gataatcagg     420
caggtgttgg tcatgatcct tgacgttgat tacatcaccg agaatggaaa gcccgtcatc     480
agggtcttca agaaggagaa cggcgagttc aggattgaat acgaccgcga gttcgagccc     540
tacttctacg cgctcctcag ggacgactct gccatcgaag aaatcaaaaa gataaccgcg     600
gagaggcacg gcagggtcgt taaggttaag cgcgcggaga aggtgaagaa aaagttcctc     660
ggcaggtctg tggaggtctg ggtcctctac ttcacgcacc cgcaggacgt tccggcaatc     720
cgcgacaaaa taaggaagca ccccgcggtc atcgacatct acgagtacga catacccttc     780
gccaagcgct acctcataga caagggccta atcccgatgg aaggtgagga agagcttaaa     840
ctcatgtcct tcgacatcga gacgctctac cacgagggag aagagtttgg aaccgggccg     900
attctgatga taagctacgc cgatgaaagc gaggcgcgcg tgataacctg aagaagatc      960
gaccttcctt acgttgaggt tgtctccacc gagaaggaga tgattaagcg cttcttgagg    1020
gtcgttaagg agaaggaccc ggacgtgctg ataacataca acggcgacaa cttcgacttc    1080
gcctacctga aaaagcgctg tgagaagctt ggcgtgagct ttaccctcgg gagggacggg    1140
agcgagccga agatacagcg catgggggac aggtttgcgg tcgaggtgaa gggcagggta    1200
cacttcgacc tttatccagt cataaggcgc accataaacc tcccgaccta caccttgag    1260
gctgtatacg aggcggtttt cggcaagccc aaggagaagg tctacgccga ggagatagcc    1320
accgctgggg agaccggcga ggggcttgag agggtcgcgc gctactcgat ggaggacgcg    1380
agggttacct acgagcttgg cagggagttc ttcccgatgg aggcccagct ttccaggctc    1440
atcggccaag gcctctggga cgtttcccgc tccagcaccg gcaacctcgt cgagtggttc    1500
ctcctaagga aggcctacga gaggaacgaa ctcgctccca acaagcccga cgagagggag    1560
ctggcgagga gaagggggggg ctacgccggt ggctacgtca aggagccgga gcggggactg    1620
tgggacaata tcgtgtatct agactttcgt agtctctacc cttcaatcat aatcacccac    1680
aacgtctcgc cagatacgct caaccgcgag gggtgtagga gctacgacgt tgcccccgag    1740
gtcggtcaca agttctgcaa ggacttcccc ggcttcattc cgagcctgct cggaaacctg    1800
ctggaggaaa ggcagaagat aaagaggaag atgaaggcaa ctctcgaccc gctggagaag    1860
aatctcctcg attacaggca acgcgccatc aagattctcg ccaacagcct tcttcccggg    1920
gagtggggttg cggtcattga agggggaaa ctcaggcccg tccgcatcgg cgagctggtt    1980
gatggactga tggaagccag cggggagagg gtgaaaagag acggcgacac cgaggtcctt    2040
gaagtcgagg ggctttacgc ctctccttcg acagggagtc caagaaagcc cgcacaatgc    2100
cggtgaaagc cgtgataagg caccgctatg ccggggaagt ttacagaata gctctcaact    2160
```

-continued

```
ccggaaggag gattaagcgt gacgcgcggc cacagcctct tcgcgtaccg ggacgcgagc    2220
ttgtggaggt gacgggggag gaggaggttc aagcccggcg acctcctggc ggtgccaagc    2280
ggataaccct cccggagagg agggagaggc tcaacatcgt tgaactgctc ctcgaactgc    2340
ccgaggagga aacggccgac atgtcatcga cattccggca agggtagaaa gaacttcttc    2400
aggggaatgc tcagaaccct ccgctggatt ttcggggagg agaagaccgg agggcggcca    2460
ggcgctacct ggagcacctt gcgtgggctc ggctacgtga agctgaggaa atcggctac    2520 ggggtggttg atagggaggg actgggaaag gtaccgcgct tctacgagag gctcgtggag    2580
gtaatccgct acaacggcaa cagggggag ttcatcgccg atttcaacgc gctccgcccc    2640
gtcctccgcc tgatgatgcc cgagaaggag cttgaagagt ggctcgttgg gacgaggaac    2700
gggttcagga taaggccgtt catagaggtt gattggaagt tcgcaaagct cctcggctac    2760
tacgtgagcg aggggagcgc cgggaagtgg aaaaaccgga ccgggggctg gagctactcg    2820
gtgaggcttt acaacgagga cgggagcgtt ctcgacgaca tggagagact cgcgaggagt    2880
tctttggggg cgtgagcgcg gggggaacta cgtcgagatt tcaaagaaga tggcctacat    2940
aatcttcgag gggctctgcg gttcaccggc cgagaacaag agggttccgt ggcttatctt    3000
cacgtcccct gaggaggtcc gctgggcctt ccttgagggg tacttcatcg gcgacggcga    3060
cgttcacccg agcaagatgg ttcggctctc caccaagagc gagcttctgg ctaacggcct    3120
cgtcctgctc ctgaactcgc tgggcgtctc agcgataaac gtccgccacg acagcggggt    3180
ttacagggtc tacgtgaacg aggaactgcc ctttacagag taccggaagc ggaagaacgc    3240
ctcacttact cccacgtcat accgaggaa gtgctggagg agacttcggc cgggccttcc    3300
agaagaacat gagtcacggg aaattcaggg agctggtgga agcggggag ctcgacgcgg    3360 aaagggccgg taggataggc tggctcctcg acggggatat agtcctcgac agggtctcgg    3420
aagtcaggaa ggaaagctac gagggtacg tctacgacct gagcgttgag gaggacgaga    3480
acttctggcg ggcttttggt tcctctacgc gcacaacnna gctactacgg ctactacggc    3540
tatgccaggc aagatggta ctgcaggag tgcgccgaga gcgttacggc atggggaagg    3600
gagtacatcg aaatggtcat cagagagctt gaggaaaagt tcggttttaa agtcctctat    3660
gcagacacag acggtctcca tgccaccatt cctggagcgg acgctgaaac agtcaagaaa    3720
aaggcaatgg agttcttaaa ctatatcaat cccaaactgc ccggccttct cgaactcgaa    3780
tacgagggct tctacgtcag gggcttcttc gtcacgaaga aaaagtacgc ggtcatcgac    3840
gaggagggca agataaccac gcgcgggctt gagatagtca ggcgcgactg gagcgagata    3900
gcgaaggaga cgcaggcgag ggttttggag gcgatactca ggcacggtga cgttgaagag    3960
gccgtcagaa ttgtcaggga agtcaccgaa aagctgagca agtacgaggt tccgccggag    4020
aagctggtta tccacgagca gataacgcgc gagctcaagg actacaaggc caccggcccg    4080
cacgtagcca tagcgaagcg tttggccgcc agaggtgtta aaatccggcc cggaactgtg    4140
ataagctaca tcgttctgaa gggctccgga aggataggcg acaggggcgat tcccttcgac    4200 gagttcgacc cgacgaagca caagtacgat gcggactact acatcgagaa ccaggttctg    4260
ccggcagttg agagaatcct caggggccttc ggctaccgca aggaagacct gcgctaccag    4320
aagacgaggc aggtcgggct tggcgcgtgg ctgaagccga aggggaagaa gaagtgagga    4380
attatctggt ttcttttccc agcattaaat gcttccgaca ttgccttatt tatgaaactc    4440
ctgttgtgcc tgagtttgtg ccagaaaaca gcctgttctg acggcgcttt ttcttgccag    4500
```

-continued

```
gtctcttgag tttcgcaagg gtcttctcga ccagctcaat ggtcttgtcg tcattgtttn    4560
nnnnnnnnnn nnnnnnnnnn cccgggact tcatactggc ggtaatagac agggattcct    4620
tcctcaagga cttcccggga ggcattggag ttttttggtg gggctttcac aggatttgct    4680
catcttgtgg atttctcgtt cgattgaatc tgtccacttg agggtgtagg tcgagacggt    4740
ggagcgcgta ttccgggagc gggtcttgag gctccatttt tcagtcctcc tccggcgaag    4800
aagtggaact caagccgggt gttagcttat gttatgttcc caactcctcc agcacctcca    4860 ggatccctc aatcccggaa cctcgaagcc cctctcgtgg atctttctaa cttcctctgc    4920
ctccgggttt atccagaccg cccacatgcc ggctctcagc gcaccctcga atcctccgc    4980 gtaggtgtcg ccgatgtgga ttgcctcgtc cggctcgacc ccgaagcatc gagcggtttt    5040
ctgaacatct cgggcatcgg cttatacgcc agaacctcgt cggcgaagaa ggttccctca    5100
atgtagtcca tcaggccgaa cctctcgagg gggggcccgg tacccaattc gccctatagt    5160
gagtcgatta caattcactg gccgtcgttt tacaacgtcg tgactgggaa aaccctggcg    5220
ttacccaact taagtcgctt tgcagcacat ccccc                              5255
```

<210> SEQ ID NO 5
<211> LENGTH: 8
<212> TYPE: PRT
<213> ORGANISM: Thermococcus sp. JDF-3
<220> FEATURE:
<221> NAME/KEY: UNSURE
<222> LOCATION: (2)..(3)
<223> OTHER INFORMATION: X = unknown
<221> NAME/KEY: UNSURE
<222> LOCATION: (6)..(6)
<223> OTHER INFORMATION: X = unknown

<400> SEQUENCE: 5

Lys Xaa Xaa Asn Ser Xaa Tyr Gly
1               5

<210> SEQ ID NO 6
<211> LENGTH: 10
<212> TYPE: PRT
<213> ORGANISM: Thermococcus sp. JDF-3
<220> FEATURE:
<221> NAME/KEY: UNSURE
<222> LOCATION: (2)..(4)
<223> OTHER INFORMATION: unknown
<221> NAME/KEY: VARIANT
<222> LOCATION: (5)..(5)
<223> OTHER INFORMATION: X = F or Y

<400> SEQUENCE: 6

Lys Xaa Xaa Xaa Xaa Gly Xaa Xaa Tyr Gly
1               5                   10

<210> SEQ ID NO 7
<211> LENGTH: 10
<212> TYPE: PRT
<213> ORGANISM: Thermococcus sp. JDF-3
<220> FEATURE:
<221> NAME/KEY: UNSURE
<222> LOCATION: (2)..(3)
<223> OTHER INFORMATION: X = unknown

<400> SEQUENCE: 7

Asp Xaa Xaa Ser Leu Tyr Pro Ser Ile Ile
1               5                   10

<210> SEQ ID NO 8

```
<210> SEQ ID NO 8
<211> LENGTH: 10
<212> TYPE: PRT
<213> ORGANISM: Thermococcus sp. JDF-3

<400> SEQUENCE: 8

Asp Phe Arg Ser Leu Tyr Leu Ser Ile Ile
1               5                   10

<210> SEQ ID NO 9
<211> LENGTH: 10
<212> TYPE: PRT
<213> ORGANISM: Thermococcus sp. JDF-3

<400> SEQUENCE: 9

Asp Phe Arg Ser His Tyr Pro Ser Ile Ile
1               5                   10

<210> SEQ ID NO 10
<211> LENGTH: 10
<212> TYPE: PRT
<213> ORGANISM: Thermococcus sp. JDF-3

<400> SEQUENCE: 10

Asp Phe Arg Ser Phe Tyr Pro Ser Ile Ile
1               5                   10

<210> SEQ ID NO 11
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide PCR primer

<400> SEQUENCE: 11
gggaaacata tgatccttga cgttgattac                              30

<210> SEQ ID NO 12
<211> LENGTH: 31
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide PCR primer

<400> SEQUENCE: 12
gggaaaggat cctcacttct tcttcccctt c                            31

<210> SEQ ID NO 13
<211> LENGTH: 34
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide primer

<400> SEQUENCE: 13
tcagatgaat tcgatgatcc ttgacgttga ttac                         34

<210> SEQ ID NO 14
<211> LENGTH: 54
<212> TYPE: DNA
<213> ORGANISM: Artificial/Unknown
<220> FEATURE:
```

```
<221> NAME/KEY: misc_feature
<222> LOCATION: ()..()
<223> OTHER INFORMATION: Synthetic oligonucleotide primer

<400> SEQUENCE: 14
gagagaattc ataatgataa ggaggaaaaa attatgatcc ttgacgttga ttac        54

<210> SEQ ID NO 15
<211> LENGTH: 31
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide primer

<400> SEQUENCE: 15
tcagatctcg agtcacttct tcttcccctt c                                 31

<210> SEQ ID NO 16
<211> LENGTH: 29
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide sequencing primer

<400> SEQUENCE: 16
ccagctttcc agactagtcg gccaaggcc                                    29

<210> SEQ ID NO 17
<211> LENGTH: 16
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide sequencing primer

<400> SEQUENCE: 17
aactctcgac ccgctg                                                  16

<210> SEQ ID NO 18
<211> LENGTH: 37
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic oligonucleotide primer

<400> SEQUENCE: 18
ggtttcccag tcacgacgtt gtaaaacgac ggccagt                           37

<210> SEQ ID NO 19
<211> LENGTH: 18
<212> TYPE: DNA
<213> ORGANISM: Artificial/Unknown
<220> FEATURE:
<221> NAME/KEY: misc_feature
<222> LOCATION: ()..()
<223> OTHER INFORMATION: First strand of synthetic oligonucleotide
      duplex

<400> SEQUENCE: 19
taacgttggg gggggca                                                 18
```

-continued

<210> SEQ ID NO 20
<211> LENGTH: 18
<212> TYPE: DNA
<213> ORGANISM: Artificial/Unknown
<220> FEATURE:
<221> NAME/KEY: misc_feature
<222> LOCATION: ()..()
<223> OTHER INFORMATION: Second strand of synthetic oligonucleotide
      duplex

<400> SEQUENCE: 20
tgcaaccccc ccccgtat                                                    18

<210> SEQ ID NO 21
<211> LENGTH: 139
<212> TYPE: PRT
<213> ORGANISM: Thermococcus sp. JDF-3
<220> FEATURE:
<221> NAME/KEY: UNSURE
<222> LOCATION: (6)..(6)
<223> OTHER INFORMATION: X = unknown

<400> SEQUENCE: 21

Leu Val Cys Asn Ala Xaa Ser Thr Gly Asn Leu Val Glu Trp Phe Leu
1               5                   10                  15

Leu Arg Lys Ala Tyr Glu Arg Asn Glu Leu Ala Pro Asn Lys Pro Asp
            20                  25                  30

Glu Arg Glu Leu Ala Arg Arg Gly Gly Tyr Ala Gly Gly Tyr Val
        35                  40                  45

Lys Glu Pro Glu Arg Gly Leu Trp Asp Asn Ile Val Tyr Leu Asp Phe
    50                  55                  60

Arg Ser Leu Tyr Pro Ser Ile Ile Ile Thr His Asn Val Ser Pro Asp
65                  70                  75                  80

Thr Leu Asn Arg Glu Gly Cys Arg Ser Tyr Asp Val Ala Pro Glu Val
                85                  90                  95

Gly His Lys Phe Cys Lys Asp Phe Pro Gly Phe Ile Pro Ser Leu Leu
            100                 105                 110

Gly Asn Leu Leu Glu Glu Arg Gln Lys Ile Lys Arg Lys Met Lys Ala
        115                 120                 125

Thr Leu Asp Pro Leu Glu Lys Asn Leu Leu Asp
    130                 135

<210> SEQ ID NO 22
<211> LENGTH: 140
<212> TYPE: PRT
<213> ORGANISM: Thermococcus sp. JDF-3

<400> SEQUENCE: 22

Val Trp Asp Val Ser Arg Ser Ser Thr Gly Asn Leu Val Glu Arg Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Ser Val Ser Pro
65                  70                  75                  80

Asp Thr Leu Asp Arg Glu Gly Cys Arg Ser Tyr Asp Val Ala Pro Glu
                85                  90                  95

```
Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
            115                 120                 125

Ala Thr Leu Asp Pro Leu Glu Lys Asn Leu Leu Asp
        130                 135                 140
```

<210> SEQ ID NO 23
<211> LENGTH: 140
<212> TYPE: PRT
<213> ORGANISM: Thermococcus sp. JDF-3

<400> SEQUENCE: 23

```
Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
            115                 120                 125

Ala Thr Leu Asp Pro Leu Glu Lys Asn Leu Leu Asp
        130                 135                 140
```

<210> SEQ ID NO 24
<211> LENGTH: 140
<212> TYPE: PRT
<213> ORGANISM: Thermococcus sp. JDF-3

<400> SEQUENCE: 24

```
Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Met Lys Met Lys
            115                 120                 125

Ala Thr Leu Asp Pro Leu Glu Lys Asn Leu Leu Asp
        130                 135                 140
```

```
<210> SEQ ID NO 25
<211> LENGTH: 140
<212> TYPE: PRT
<213> ORGANISM: Thermococcus sp. JDF-3

<400> SEQUENCE: 25

Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140

<210> SEQ ID NO 26
<211> LENGTH: 140
<212> TYPE: PRT
<213> ORGANISM: Thermococcus sp. JDF-3
<220> FEATURE:
<221> NAME/KEY: UNSURE
<222> LOCATION: (5)..(5)
<223> OTHER INFORMATION: X = unknown

<400> SEQUENCE: 26

Val Trp Asp Val Xaa Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Gln Trp Asp Asn Ile Ala Tyr Leu Asp
    50                  55                  60

Phe Arg Ser Leu Tyr Pro Ser Ile Ile Ile Thr His Asn Val Ser Pro
65                  70                  75                  80

Asp Thr Leu Lys Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140

<210> SEQ ID NO 27
<211> LENGTH: 140
<212> TYPE: PRT
```

<213> ORGANISM: Thermococcus sp. JDF-3

<400> SEQUENCE: 27

```
Val Trp Asp Val Pro Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65              70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140
```

<210> SEQ ID NO 28
<211> LENGTH: 140
<212> TYPE: PRT
<213> ORGANISM: Thermococcus sp. JDF-3
<220> FEATURE:
<221> NAME/KEY: UNSURE
<222> LOCATION: (92)..(92)
<223> OTHER INFORMATION: X = unknown

<400> SEQUENCE: 28

```
Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65              70                  75                  80

Asp Thr Leu Asn Arg Glu Gly Cys Arg Ser Tyr Xaa Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140
```

<210> SEQ ID NO 29
<211> LENGTH: 140
<212> TYPE: PRT
<213> ORGANISM: Thermococcus sp. JDF-3
<220> FEATURE:
<221> NAME/KEY: UNSURE
<222> LOCATION: (92)..(92)
<223> OTHER INFORMATION: X = Unknown

```
<400> SEQUENCE: 29

Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
            35                  40                  45

Val Lys Glu Pro Glu Arg Gly Pro Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Xaa Val Ala Pro Glu
            85                  90                  95

Val Gly His Lys Phe Cys Lys Asp Phe Pro Gly Phe Ile Pro Ser Leu
            100                 105                 110

Leu Gly Asn Leu Leu Glu Val Arg Gln Lys Ile Lys Arg Lys Met Lys
            115                 120                 125

Ala Thr Leu Asp Pro Leu Glu Lys Asn Leu Leu Asp
    130                 135                 140

<210> SEQ ID NO 30
<211> LENGTH: 140
<212> TYPE: PRT
<213> ORGANISM: Thermococcus sp. JDF-3

<400> SEQUENCE: 30

Val Trp Asp Val Ser Arg Ser Ser Thr Gly Asn Leu Val Glu Trp Phe
1               5                   10                  15

Leu Leu Arg Lys Ala Tyr Glu Arg Asn Lys Leu Ala Pro Asn Lys Pro
            20                  25                  30

Asp Glu Arg Glu Leu Ala Arg Arg Gly Gly Tyr Ala Gly Gly Tyr
            35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
            85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
            115                 120                 125

Ala Thr Leu Asp Pro Leu Glu Lys Asn Leu Leu Asp
    130                 135                 140

<210> SEQ ID NO 31
<211> LENGTH: 140
<212> TYPE: PRT
<213> ORGANISM: Thermococcus sp. JDF-3
<220> FEATURE:
<221> NAME/KEY: UNSURE
<222> LOCATION: (4)..(4)
<223> OTHER INFORMATION: X = unknown
<221> NAME/KEY: UNSURE
<222> LOCATION: (6)..(6)
<223> OTHER INFORMATION: X = unknown

<400> SEQUENCE: 31
```

Tyr Trp Ser Xaa Pro Xaa Leu Arg Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65              70                  75                  80

Asp Thr Leu Asn Arg Glu Gly Cys Arg Ser Tyr Asp Val Ala Pro Glu
            85                  90                  95

Val Gly His Lys Phe Cys Lys Asp Phe Pro Gly Phe Ile Pro Ser Leu
            100                 105                 110

Leu Gly Asn Pro Leu Glu Glu Arg Gln Lys Ile Lys Arg Lys Met Lys
            115                 120                 125

Ala Thr Leu Asp Pro Leu Glu Lys Asn Leu Leu Asp
    130                 135                 140

<210> SEQ ID NO 32
<211> LENGTH: 141
<212> TYPE: PRT
<213> ORGANISM: Thermococcus sp. JDF-3
<220> FEATURE:
<221> NAME/KEY: Unsure
<222> LOCATION: (5)..(5)
<223> OTHER INFORMATION: X = unknown

<400> SEQUENCE: 32

Val Asp Gly Thr Xaa Pro Arg Ser Ser Thr Gly Asn Leu Val Glu Trp
1               5                   10                  15

Phe Leu Leu Arg Lys Ala Tyr Glu Arg Asn Glu Leu Ala Pro Asn Lys
            20                  25                  30

Pro Asp Glu Arg Glu Leu Ala Arg Arg Gly Gly Tyr Ala Gly Gly
        35                  40                  45

Tyr Val Lys Glu Pro Glu Arg Gly Leu Trp Asp Asn Ile Val Tyr Leu
    50                  55                  60

Asp Phe Arg Ser His Tyr Pro Ser Ile Ile Ile Thr His Asn Val Ser
65              70                  75                  80

Pro Asp Thr Leu Asn Arg Glu Gly Cys Arg Ser Tyr Asp Val Ala Pro
            85                  90                  95

Glu Asp Gly His Lys Phe Cys Lys Asp Phe Pro Gly Phe Ile Pro Ser
            100                 105                 110

Leu Leu Gly Asn Leu Leu Glu Glu Arg Gln Lys Ile Lys Arg Lys Met
            115                 120                 125

Lys Ala Thr Leu Asp Pro Leu Glu Lys Asn His Leu Asp
    130                 135                 140

<210> SEQ ID NO 33
<211> LENGTH: 143
<212> TYPE: PRT
<213> ORGANISM: Thermococcus sp. JDF-3
<220> FEATURE:
<221> NAME/KEY: Unsure
<222> LOCATION: (1)..(3)
<223> OTHER INFORMATION: X = unknown

<400> SEQUENCE: 33

```
Xaa Xaa Xaa Phe Trp Asp Val Ser Arg Ser Thr Gly Asn Leu Val
1               5                   10                  15

Glu Trp Phe Leu Leu Arg Lys Ala Tyr Glu Arg Asn Glu Leu Ala Pro
                20                  25                  30

Asn Lys Pro Asp Glu Arg Glu Leu Ala Arg Arg Gly Gly Tyr Ala
            35                  40                  45

Gly Gly Tyr Val Lys Glu Pro Glu Arg Gly Leu Trp Asp Asn Ile Val
50                      55                  60

Tyr Leu Asp Phe Arg Ser Leu Tyr Pro Ser Ile Ile Thr His Asn
65              70                  75                  80

Val Ser Pro Asp Thr Leu Asn Arg Glu Gly Cys Arg Ser Tyr Asp Val
                85                  90                  95

Ala Pro Glu Val Gly His Lys Phe Cys Lys Asp Phe Pro Gly Phe Ile
                100                 105                 110

Pro Ser Leu Leu Gly Asn Leu Leu Glu Glu Arg Gln Lys Ile Lys Arg
            115                 120                 125

Lys Met Lys Ala Thr Leu Asp Pro Leu Glu Lys Asn Leu Leu Asp
            130                 135                 140
```

<210> SEQ ID NO 34
<211> LENGTH: 180
<212> TYPE: PRT
<213> ORGANISM: Thermococcus sp. JDF-3

<400> SEQUENCE: 34

```
Thr Gly Glu Gly Leu Glu Arg Val Ala Arg Tyr Ser Met Glu Asp Ala
1               5                   10                  15

Arg Val Thr Tyr Glu Leu Gly Arg Glu Phe Phe Pro Met Glu Ala Gln
                20                  25                  30

Leu Ser Arg Leu Ile Gly Gln Gly Asp Trp Asp Val Ser Arg Ser Ser
            35                  40                  45

Thr Gly Asn Leu Val Glu Trp Phe Leu Leu Arg Lys Ala Tyr Glu Arg
50                  55                  60

Asn Glu Leu Ala Pro Asn Lys Pro Asp Glu Arg Glu Leu Ala Arg Arg
65                  70                  75                  80

Arg Gly Gly Tyr Ala Gly Gly Tyr Val Lys Glu Pro Glu Arg Gly Leu
                85                  90                  95

Trp Asp Asn Ile Val Tyr Leu Asp Phe Arg Ser Leu Tyr Pro Ser Ile
                100                 105                 110

Ile Ile Thr His Asn Val Ser Pro Asp Thr Leu Asn Arg Glu Gly Cys
            115                 120                 125

Arg Ser Tyr Asp Val Ala Pro Glu Val Gly His Lys Phe Cys Lys Asp
        130                 135                 140

Phe Pro Gly Phe Ile Pro Ser Leu Leu Gly Asn Leu Leu Glu Glu Arg
145                 150                 155                 160

Gln Lys Ile Lys Arg Lys Met Lys Ala Thr Leu Asp Pro Leu Glu Lys
                165                 170                 175

Asn Leu Leu Asp
            180
```

<210> SEQ ID NO 35
<211> LENGTH: 180
<212> TYPE: PRT
<213> ORGANISM: Thermococcus sp. JDF-3

<400> SEQUENCE: 35

```
Tyr Arg Gln Arg Ala Ile Lys Ile Leu Ala Asn Ser Tyr Tyr Gly Tyr
1               5                   10                  15

Cys Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
                100                 105                 110

Lys Tyr Ala Val Ile Asp Glu Glu Gly Lys Ile Thr Thr Arg Gly Leu
            115                 120                 125

Glu Ile Val Arg Arg Asp Trp Ser Glu Ile Ala Lys Glu Thr Gln Ala
    130                 135                 140

Arg Val Leu Glu Ala Val Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
        180

<210> SEQ ID NO 36
<211> LENGTH: 180
<212> TYPE: PRT
<213> ORGANISM: Thermococcus sp. JDF-3

<400> SEQUENCE: 36

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
                100                 105                 110

Lys Tyr Ala Val Ile Asp Glu Glu Gly Lys Ile Thr Thr Arg Gly Leu
            115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Glu Leu
        180
```

```
<210> SEQ ID NO 37
<211> LENGTH: 180
<212> TYPE: PRT
<213> ORGANISM: Thermococcus sp. JDF-3

<400> SEQUENCE: 37

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
130                 135                 140

Arg Val Leu Glu Ala Ile Leu Arg His Gly Asp Val Glu Glu Ala Val
145                 150                 155                 160

Arg Ile Val Arg Lys Val Thr Glu Lys Leu Ser Lys Tyr Glu Val Pro
                165                 170                 175

Pro Glu Lys Leu
            180

<210> SEQ ID NO 38
<211> LENGTH: 180
<212> TYPE: PRT
<213> ORGANISM: Thermococcus sp. JDF-3

<400> SEQUENCE: 38

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Lys Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
130                 135                 140
```

```
Arg Val Leu Glu Ala Ile Leu Arg His Gly Asp Val Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 39
<211> LENGTH: 180
<212> TYPE: PRT
<213> ORGANISM: Thermococcus sp. JDF-3

<400> SEQUENCE: 39

Tyr Arg Gln Arg Ala Ile Lys Ile Leu Ala Asn Asn Tyr Tyr Gly Tyr
1               5                   10                  15

Tyr Gly Tyr Ala Arg Ala Arg Trp Tyr Cys Arg Glu Cys Ala Glu Ser
                20                  25                  30

Val Thr Ala Trp Gly Arg Glu Tyr Ile Glu Met Val Ile Arg Glu Leu
            35                  40                  45

Glu Glu Lys Phe Gly Phe Lys Val Leu Tyr Ala Asp Thr Asp Gly Leu
50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Val Thr Lys Lys
                100                 105                 110

Lys Tyr Ala Val Ile Asp Glu Glu Gly Lys Ile Thr Thr Arg Gly Leu
            115                 120                 125

Glu Ile Val Arg Arg Asp Trp Ser Glu Ile Ala Lys Glu Thr Gln Ala
130                 135                 140

Arg Val Leu Glu Ala Ile Leu Arg His Asp Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 40
<211> LENGTH: 180
<212> TYPE: PRT
<213> ORGANISM: Thermococcus sp. JDF-3
<220> FEATURE:
<221> NAME/KEY: Unsure
<222> LOCATION: (114)..(114)
<223> OTHER INFORMATION: X = Unknown

<400> SEQUENCE: 40

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
                20                  25                  30

Val Thr Ala Trp Gly Arg Glu Tyr Ile Glu Met Val Ile Arg Glu Leu
            35                  40                  45

Glu Glu Lys Phe Gly Phe Lys Val Leu Tyr Ala Asp Thr Asp Gly Leu
50                  55                  60

His Ala Thr Ile Pro Gly Ala Asp Ala Glu Thr Val Lys Lys Lys Ala
```

```
                65                  70                  75                  80
Met Glu Phe Leu Asn Tyr Ile Asn Leu Lys Leu Pro Gly Leu Leu Glu
                    85                  90                  95

Leu Glu Tyr Glu Gly Phe Tyr Val Arg Gly Phe Phe Val Thr Lys Lys
                100                 105                 110

Lys Xaa Ala Val Ile Asp Glu Glu Gly Lys Ile Thr Thr Arg Gly Leu
                115                 120                 125

Glu Ile Val Arg Arg Asp Trp Ser Lys Ile Ala Lys Glu Thr Gln Ala
            130                 135                 140

Arg Val Leu Glu Ala Ile Leu Arg His Gly Asp Val Glu Glu Ala Ile
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 41
<211> LENGTH: 180
<212> TYPE: PRT
<213> ORGANISM: Thermococcus sp. JDF-3

<400> SEQUENCE: 41

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
                20                  25                  30

Val Thr Ala Trp Gly Arg Glu Tyr Ile Glu Met Val Ile Arg Glu Leu
            35                  40                  45

Glu Glu Lys Phe Gly Phe Lys Val Leu Tyr Ala Asp Thr Asp Gly Leu
        50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
                100                 105                 110

Lys Tyr Ala Val Ile Asp Glu Glu Gly Lys Ile Ala Thr Arg Gly Leu
                115                 120                 125

Glu Ile Val Arg Arg Asp Trp Ser Glu Ile Ala Lys Glu Thr Gln Ala
            130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 42
<211> LENGTH: 180
<212> TYPE: PRT
<213> ORGANISM: Thermococcus sp. JDF-3

<400> SEQUENCE: 42

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
```

-continued

```
            20                  25                  30
Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
                100                 105                 110

Lys Tyr Ala Val Ile Asp Glu Glu Gly Lys Ile Thr Thr Arg Gly Leu
                115                 120                 125

Glu Ile Val Arg Arg Asp Trp Ser Glu Ile Ala Lys Glu Thr Gln Ala
            130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Asn Lys Tyr Glu Val Pro
                165                 170                 175

Pro Glu Lys Leu
            180

<210> SEQ ID NO 43
<211> LENGTH: 180
<212> TYPE: PRT
<213> ORGANISM: Thermococcus sp. JDF-3

<400> SEQUENCE: 43

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
                20                  25                  30

Val Thr Ala Trp Gly Arg Glu Tyr Ile Glu Met Val Ile Arg Glu Leu
            35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
                100                 105                 110

Lys Tyr Ala Val Ile Asp Glu Glu Gly Lys Ile Thr Thr Arg Gly Leu
            115                 120                 125

Glu Ile Val Arg Arg Asp Trp Ser Glu Ile Ala Lys Glu Thr Gln Ala
            130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 44
<211> LENGTH: 180
```

```
<212> TYPE: PRT
<213> ORGANISM: Thermococcus sp. JDF-3

<400> SEQUENCE: 44

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Pro Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 45
<211> LENGTH: 180
<212> TYPE: PRT
<213> ORGANISM: Thermococcus sp. JDF-3

<400> SEQUENCE: 45

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
130                 135                 140

Arg Val Leu Glu Ala Ile Leu Arg His Gly Asp Val Glu Glu Ala Val
145                 150                 155                 160
```

-continued

Arg Ile Val Arg Glu Val Thr Glu Lys Leu Ser Lys Tyr Glu Val Pro
            165                 170                 175

Pro Val Lys Leu
            180

<210> SEQ ID NO 46
<211> LENGTH: 180
<212> TYPE: PRT
<213> ORGANISM: Thermococcus sp. JDF-3

<400> SEQUENCE: 46

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Gly Glu Ala
            180

<210> SEQ ID NO 47
<211> LENGTH: 180
<212> TYPE: PRT
<213> ORGANISM: Thermococcus sp. JDF-3

<400> SEQUENCE: 47

Tyr Arg Gln Arg Ala Ile Lys Ile Leu Ala Asn Ser Tyr Tyr Gly Asn
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

-continued

```
Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
        130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 48
<211> LENGTH: 180
<212> TYPE: PRT
<213> ORGANISM: Thermococcus sp. JDF-3

<400> SEQUENCE: 48

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
        130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180
```

COMPOSITIONS AND METHODS UTILIZING DNA POLYMERASES

This application claims the benefit of U.S. Provisional Application No. 60/162,600, filed Oct. 29, 1999.

FIELD OF THE INVENTION

The present invention relates to compositions and methods utilizing DNA polymerase enzymes with reduced discrimination for non-conventional nucleotides. The enzymes of the invention are useful in many applications calling for the detectable labeling of nucleic acids and are particularly useful in DNA sequencing applications.

BACKGROUND OF THE INVENTION

Detectable labeling of nucleic acids is required for many applications in molecular biology, including applications for research as well as clinical diagnostic techniques. A commonly used method of labeling nucleic acids uses one or more unconventional nucleotides and a polymerase enzyme that catalyzes the template-dependent incorporation of the unconventional nucleotide(s) into the newly synthesized complementary strand.

The ability of a DNA polymerase to incorporate the correct deoxynucleotide is the basis for high fidelity DNA replication in vivo. Amino acids within the active site of polymerases form a specific binding pocket that favors the placement of the correct complementary nucleotide opposite the template nucleotide. If a mismatched nucleotide, ribonucleotide, or nucleotide analog fills that position, the precise alignment of the amino acids contacting the incoming nucleotide may be distorted into a position unfavorable for DNA polymerization. Because of this, the unconventional nucleotides or nucleotide analogs used to label DNA tend to be incorporated into the elongated strand less efficiently than do the standard deoxynucleotide triphosphates (dNTPs; the so-called "standard" dNTPs include deoxyadenosine triphosphate (dATP), deoxycytosine triphosphate (dCTP), deoxyguanosine triphosphate (dGTP), and thymidine triphosphate (TTP)).

The reduced efficiency with which unconventional nucleotides are incorporated by the polymerase increases the amount of the unconventional nucleotide necessary for DNA labeling. The reduced efficiency of incorporation of a particular nucleotide can also adversely affect the performance of techniques or assays, such as DNA sequencing, that depend upon unbiased incorporation of unconventional nucleotides for homogeneous signal strength.

The identity and exact arrangement of the amino acids of a DNA polymerase that contact an incoming nucleotide triphosphate determine the nature of the nucleotides, both conventional and unconventional, that may be incorporated by that polymerase enzyme. Changes in the exact placement of the amino acids that contact the incoming nucleotide triphosphate at any stage of binding or chain elongation can dramatically alter the polymerase's capacity for utilization of unusual or unconventional nucleotides. Sometimes changes in distant amino acids can influence the incorporation of nucleotide analogs due to indirect global or structural effects. Polymerases with increased capacity to incorporate nucleotide analogs are useful for labeling DNA or RNA strands with nucleotides modified with signal moieties such as dyes, reactive groups or unstable isotopes.

In addition to labeled nucleotides, an extremely important class of modified nucleotides is the dideoxynucleotides. The so-called "Sanger" or "dideoxy" DNA sequencing method (Sanger et al., 1977, Proc. Natl. Acad. Sci. USA 74: 5463, which is incorporated herein by reference) relies upon the template-directed incorporation of nucleotides onto an annealed primer by a DNA polymerase from a mixture containing deoxy- and dideoxynucleotides. The incorporation of a dideoxynucleotide results in chain termination, the inability of the enzyme to catalyze further extension of that strand. Electrophoretic separation of reaction products results in a "ladder" of extension products wherein each extension product ends in a particular dideoxynucleotide complementary to the nucleotide opposite it in the template. The distance of the dideoxynucleotide analog from the primer is indicated by the length of the extension product. When four reactions, each containing one of the four dideoxynucleotide analogs ddA, ddC, ddG, or ddT (ddNTPs) are separated on the same gel, the sequence of the template may be read directly from the ladder patterns. Extension products may be detected in several ways, including for example, the inclusion of isotopically- or fluorescently-labeled primers, deoxynucleotide triphosphates or dideoxynucleotide triphosphates in the reaction.

Fluorescent labeling has the advantages of faster data collection, since detection may be performed while the gel is running, and longer reads of sequence data from a single reaction and gel. Further, fluorescent sequence detection has allowed sequencing to be performed in a single reaction tube containing four differentially-labeled fluorescent dye terminators (the so-called dye-terminator method, Lee et al., 1992, Nucleic Acids Res. 20: 2471, incorporated herein by reference).

A desirable quality of a polymerase useful for DNA sequencing is improved incorporation of dideoxynucleotides. Improved incorporation of dideoxynucleotides can make processes such as DNA sequencing more cost effective by reducing the requirement for expensive radioactive or fluorescent dye-labeled dideoxynucleotides. Moreover, unbiased dideoxynucleotide incorporation provides improved signal uniformity, leading to increased accuracy of base determination. The even signal output further allows subtle sequence differences caused by factors like allelic variation to be detected. Allelic variation, which produces two different half strength signals at the position of relevance, can easily be concealed by the varied signal strengths caused by polymerases with non-uniform ddNTP utilization.

Incorporation of ribonucleotides by the native form of DNA polymerase is a rare event. Mutants that incorporate higher levels of ribonucleotides can be used for applications such as sequencing by partial ribosubstitution. In this system, a mixture of ribonucleotides and deoxynucleotides corresponding to the same base are incorporated by the mutant polymerase (Barnes, 1978 J. Mol. Biol. 119:83–99). When the ribosequencing reactions are exposed to alkaline conditions and heat, fragmentation of the extended strand occurs. If the reactions for all four bases are separated on a denaturing acrylamide gel, they produce a sequencing ladder. there is a need in the art for polymerase mutants with higher utilization of ribonucleotides for this alternative method of sequencing.

Alternatively, the incorporation of ribonucleotides followed by alkaline hydrolysis could be utilized in a system that requires random cleavage of DNA molecules such as DNA shuffling ((Stemmer, 1994, Nature, 370: 389–391) which has also been called molecular breeding, sexual PCR and directed evolution).

Another desirable quality in a DNA labeling enzyme is thermal stability. DNA polymerases exhibiting thermal stability have revolutionized many aspects of molecular biology and clinical diagnostics since the development of the polymerase chain reaction (PCR), which uses cycles of thermal denaturation, primer annealing, and enzymatic primer extension to amplify DNA templates. The prototype thermostable DNA polymerase is Taq polymerase, originally isolated from the thermophilic eubacterium *Thermus aquaticus*. So-called "cycle sequencing" reactions using thermostable DNA polymerases have the advantage of requiring smaller amounts of starting template relative to conventional (i.e., non-cycle) sequencing reactions.

There are three major families of DNA polymerases, termed families A, B and C. The classification of a polymerase into one of these three families is based on structural similarity of a given polymerase to *E. coli* DNA polymerase I (Family A), II (Family B) or III (family C). As examples, Family A DNA polymerases include, but are not limited to Klenow DNA polymerase, *Thermus aquaticus* DNA polymerase I (Taq polymerase) and bacteriophage T7 DNA polymerase; Family B DNA polymerases, formerly known as α-family polymerases (Braithwaite and Ito, 1991, Nuc. Acids Res. 19:4045), include, but are not limited to human α, δ and ε DNA polymerases, T4, RB69 and Φ29 bacteriophage DNA polymerases, and *Pyrococcus furiosus* DNA polymerase (Pfu polymerase); and family C DNA polymerases include, but are not limited to *Bacillus subtilis* DNA polymerase III, and *E. coli* DNA polymerase III α and ε subunits (listed as products of the dnaE and dnaQ genes, respectively, by Brathwaite and Ito, 1993, Nucleic Acids Res. 21: 787). An alignment of DNA polymerase protein sequences of each family across a broad spectrum of archaeal, bacterial, viral and eukaryotic organisms is presented in Braithwaite and Ito (1993, supra), which is incorporated herein by reference.

The term used to describe the tendency of DNA polymerases to not to carry the incorporation of unnatural nucleotides into the nascent DNA polymer is "discrimination". In Family A DNA polymerases, the effective discrimination against incorporation of dideoxynucleotide analogs is largely associated with a single amino acid residue. The majority of enzymes from the Family A DNA polymerases have a phenylalanine (phe or F) residue at the position equivalent to F762 in *E. coli* Klenow fragment of DNA polymerase and demonstrate a strong discrimination against dideoxynucleotides. A few polymerases (e.g. T7 DNA polymerase) have a tyrosine (tyr or Y) residue at the corresponding position and exhibit relatively weak discrimination against dideoxynucleotides. Family A polymerases with tyrosine at this position readily incorporate dideoxynucleotides at levels equal to or only slightly different from the levels at which they incorporate deoxynucleotides. Conversion of the tyrosine or phenylalanine residues in the site responsible for discrimination reverses the dideoxynucleotide discrimination profile of the Family A enzymes (Tabor and Richardson, 1995, Proc. Natl. Acad. Sci. USA 92:6449).

Among the thermostable DNA polymerases, a mutant form of the Family A DNA polymerase from *Thermus aquaticus*, known as AmpliTaq FS® (Perkin Elmer), contains a F667Y mutation at the position equivalent to F762 of Klenow DNA polymerase and exhibits increased dideoxynucleotide uptake (i.e., reduced discrimination against ddNTPs) relative to the wild-type enzyme. The reduced discrimination for dideoxynucleotide uptake makes it more useful for fluorescent and labeled dideoxynucleotide sequencing than the wild-type enzyme.

The F667Y mutant of Taq DNA polymerase is not suited, however, for use with fluorescein-labeled dideoxynucleotides, necessitating the use of rhodamine dye terminators. Rhodamine dye terminators that are currently utilized with Taq sequencing reactions, however, stabilize DNA secondary structure, causing compression of signal. Efforts to eliminate compression problems have resulted in systems that use high amounts of the nucleotide analog deoxyinosine triphosphate (dITP) in place of deoxyguanosine triphosphate. While incorporation of (dITP) reduces the compression of the signal, the presence of dITP in the reaction produces additional complications including lowered reaction temperatures and increased reaction times. Additionally, the use of rhodamine dyes in sequencing requires undesirable post-reaction purification (Brandis, 1999 Nuc. Acid Res. 27:1912).

Family B DNA polymerases exhibit substantially different structure compared to Family A DNA polymerases, with the exception of the position of acidic residues involved in catalysis in the so-called palm domain (Wang et al., 1997, Cell 89:1087; Hopfner et al., 1999, Proc. Natl. Acad. Sci. USA 96:3600). The unique structure of Family B DNA polymerases may permit a completely different spectrum of interactions with nucleotide analogs, perhaps allowing utilization of analogs which are unsuitable for use with Family A DNA polymerases due to structural constraints. Thermostable Family B DNA polymerases have been identified in hyperthermophilic archaea. These organisms grow at temperatures higher than 91° C. and their enzymes demonstrate greater themostability (Mathur et al., 1992, Stratagies 5:11) than the thermophilic eubacterial Family A DNA polymerases. Family B polymerases from hyperthermophilic archaea may be well suited starting substrates for modification(s) to reduce discrimination against nonconventional nucleotides.

Although the crystal structures of three Family B DNA polymerases have been solved (Wang et al., 1997, supra; Hopfner, K.-P. et al., 1999, Proc. Natl. Acad. Sci. 96: 3600; Zhao, 1999, Structure Fold Des., 7:1189), the structures of DNA-polymerase or dNTP-polymerase co-complexes have not yet been reported. At present, identification of amino acid residues contributing to nucleotide analog discrimination can only be inferred from extrapolation to Family A-dNTP structures or from mutagenesis studies carried out with related Family B DNA polymerases (e.g., human polα, phage T4, phage Φ29, *T. litoralis* DNA polymerase).

Sequence comparison of the Family B DNA polymerases indicate six conserved regions numbered I–VI (Braithwaite and Ito, 1993, supra). The crystal structure of bacteriophage RB69 DNA polymerase (Family B) proposed by Wang et al. (Wang et al., 1997, supra) shows that Y416 in region II ( which corresponds to Y409 in the Family B DNA polymerase of *Thermococcus* species JDF-3) has the same position as Y115 in HIV reverse transcriptase (RT) and E710 in the Klenow fragment (Family A polymerases). Modeling of the dNTP and primer template complex in RB69 was carried out using the atomic coordinates of the reverse transcriptase-DNA cocrystal. This model predicts the RB69 Y416 packs under the deoxyribose portion of the dNTP. Tyrosine at this position has been implicated in ribose selectivity, contributing to polymerase discrimination between ribonucleotides and deoxribonucleotides in mammalian reverse transcriptases (Y115) (Gao et al., 1997, Proc. Natl. Acad. Sci. USA 94:407; Joyce, 1994, Proc. Natl. Acad. Sci. USA 94:1619) and in Family A DNA polymerases where modification of the corresponding invariable glutamate residue (E710) reduces discrimination against ribonucleotides (Gelfand et al., 1998, Pat. No. EPO823479; Astatke et al., 1998, Proc. Natl. Acad. Sci. USA 96:3402).

Mutagenesis studies done in Family B DNA polymerases also implicate the region containing the analogous Y in region II in dNTP incorporation and ribose selectivity. Mutations at the corresponding Y865 in human DNA polymerase α affect polymerase fidelity and sensitivity to dNTP nucleotide inhibitors such as AZT-TP, which has a bulky 3'-azido group in place of the 3'-OH group, BuPdGTP, which contains a butylphenyl group attached to the amino group at the C-2 position in the guanine base of dGTP (resulting in a bulkier and more hydrophobic purine base nucleotide) and aphidicolin, a competitive inhibitor of pyrimidine deoxynucleotide triphosphate. Interestingly, the mutants showed no difference in their uptake of ddCTP (Dong et al., 1993, J. Biol. Chem. 268: 24163). Additionally, mutants of bacteriophage T4 DNA polymerase, which have converted L412 to methionine (M) or isoleucine (I) just one amino acid before the analogous Y (Y411), show extreme and mild sensitivity, respectively, to the inorganic pyrophosphate analog phosphonoacetic acid (PAA). Alterations in PAA sensitivity have been shown to predict polymerase interactions with nucleotide analogs. L412 in T4 DNA polymerase corresponds to L410 in *Thermococcus* species JDF-3 DNA polymerase. The L412M T4 DNA polymerase mutant was inhibited with 50-fold less ddGTP than wild-type polymerase while the $K_m$s for dGTP was similar. As stated by the authors in that study, "[d]espite the sensitivity of the L412M DNA polymerase to ddGTP, there was no difference found in the incorporation of ddNTPs by wild-type and L412M DNA polymerase." (Reha-Krantz et al., 1993, J. Virol. 67:60). In bacteriophage Φ29, mutations in region II (LYP where Y is analogous to *Thermococcus* species JDF3 DNA polymerase Y409) produce mixed results when challenged with PAA; P255S was hypersensitive to PAA while L253V was shown to be less sensitive than the wild-type enzyme (Blasco et al., 1993, J. Biol. Chem. 268: 24106). These data support the role of the LYP region (region II) in polymerase-nucleotide interactions, but improved incorporation of ddNTPs was not achieved in these references.

In another study, extensive mutation of region II in the archaeal Family B DNA polymerase from *Thermococcus litoralis* DNA polymerase (VENT™ polymerase, New England Biolabs) was performed. In that study, 26 different site-directed mutants were made for the sole intent of examining nucleotide analog discrimination (Gardner and Jack, 1999, Nucleic Acids Res. 27: 2545). Site-directed mutagenesis of VENT™ DNA polymerase demonstrated that three mutations at Y412 (which corresponds to JDF-3 DNA polymerase Y409) could alter nucleotide binding (Gardner and Jack, 1999, supra). Y412V was most significant with a 2 fold increase in dideoxynucleotide incorporation and a 200 fold increase in the incorporation of ribonucleotide ATP. The mutation Y412F showed no change in analog incorporation.

Region III of the Family B polymerases (also referred to as motif B) has also been demonstrated to play a role in nucleotide recognition. This region, which corresponds to AA 487 to 495 of JDF-3 Family B DNA polymerase, has a consensus sequence KX$_3$NSXYG (SEQ ID NO: 5) (Jung et al., 1990, supra; Blasco et al., 1992, supra; Dong et al., 1993, J. Biol. Chem. 268:21163; Zhu et al., 1994, Biochem. Biophys. Acta 1219:260; Dong and Wang, 1995, J. Biol. Chem. 270:21563), and is functionally, but not structurally (Wang et al., 1997, supra), analogous to KX$_3$(F/Y)GX$_2$YG (SEQ ID NO: 6) in helix O of the Family A DNA polymerases. In Family A DNA polymerases, such as the Klenow fragment and Taq DNA polymerases, the O helix contains amino acids that play a major role in dNTP binding (Astatke et al., 1998, J. Mol. Biol. 278:147; Astatke et al., 1995, J. Biol. Chem. 270:1945; Polesky et al., 1992, J. Biol. Chem 267:8417; Polesky et al., 1990, J. Biol. Chem. 265:14579; Pandey et al., 1994, J. Biol. Chem. 269:13259; Kaushik et al., 1996, Biochem. 35:7256). Specifically, helix O contains the F (F763 in the Klenow fragment; F667 in Taq) which confers ddNTP discrimination in Family A DNA polymerases (KX$_3$(F/Y)GX$_2$YG SEQ ID NO: 6) (Tabor and Richardson, 1995, supra).

Directed mutagenesis studies in region III of VENT™ DNA polymerase also targeted an alanine analogous to A485 of the *Thermococcus* species JDF-3 DNA polymerase (Jung et al., 1990, supra). These mutants (A→C, A→S, A→L, A→I, A→F and A→V) exhibited a range of specific activities from 0.12 to 1.2 times the polymerase activity of the progenitor enzyme (Gardner and Jack, 1999, Nucl. Acids Res. 27:2545). The dideoxynucleotide incorporation ranged from 4 to 15 times the unmutated enzyme. Interestingly, the mutant with the highest dideoxynucleotide incorporation (15×) had a specific activity of only 0.12× of the original enzyme.

Site-directed mutagenesis studies on the Family B DNA polymerase from *Thermococcus barossii* modified each residue independently in the sequence ILANSF, which corresponds to AA residues 488–493 of the JDF-3 DNA polymerase, to tyrosine (Reidl et al., U.S. Pat. No. 5,882,904). That study indicated that an L489Y mutant exhibits approximately 3 times greater incorporation of dideoxynucleotides relative to an enzyme bearing the wild-type leucine residue at this site.

One area of active research involves the use of nucleic acid arrays, often referred to as nucleic acid or DNA "chips", in the simultaneous analyses of multiple different nucleic acid sequences. Many of these applications, such as those described in U.S. Pat. No. 5,882,904 (Reidl et al., issued Mar. 16, 1999) will benefit from DNA polymerases exhibiting reduced discrimination against non-conventional nucleotides, particularly fluorescently-labeled non-conventional nucleotides. Applications being addressed in the chip format include DNA sequencing and mutation detection, among others. For example, the "mini-sequencing" methods (e.g., Pastinen et al., 1997, Genome Res. 7: 606; Syvanen, 1999, Human Mutation 13: 1–10) and the arrayed primer extension (APEX) mutation detection method (Shumaker et al., 1996, Hum. Mutat. 7: 346) and methods like them can benefit from DNA polymerases with reduced discrimination against fluorescently-labeled or other non-conventional nucleotides. There is a need in the art for a non-discriminating DNA polymerase for use in chip or gel based mini-sequencing systems. Such a system would advantageously permit detection of multiplexed single nucleotide polymorphisms (SNPs) and allow for quantitative genotyping. Identification of sequence variation permits the diagnosis and treatment of genetic disorders, predisposition to multifactorial diseases, and sensitivity to new or existing pharmaceutical products.

There is a need in the art for DNA polymerases with reduced discrimination against unconventional nucleotides. There is particularly a need in the art for thermostable DNA polymerases exhibiting reduced discrimination against dideoxynucleotides, and further, for DNA polymerases exhibiting reduced discrimination against fluorescently labeled dideoxynucleotides.

SUMMARY OF THE INVENTION

The present invention relates to compositions and methods utilizing DNA polymerase enzymes exhibiting reduced discrimination against non-conventional nucleotides. Enzymes with this quality are useful in many applications calling for the detectable labeling of nucleic acids and are particularly useful in DNA sequencing applications.

The invention further relates to a Family B DNA polymerase having one or more mutations at a site or sites corresponding to L408, P410, S345, and/or A485 of SEQ ID NO: 2, or a fragment thereof which retains the ability to direct the template-dependent polymerization of nucleic acid. The invention also encompasses mutants and modified versions (e.g., reversibly inactivated versions of a Family B polymerase prepared, for example, by chemical modification or antibody complexing) of a Family B polymerase mutated at sites corresponding to L408, P410 and or A485 of SEQ ID NO: 2.

In one embodiment, the DNA polymerase has a dual mutation comprising comprising a serine to proline mutation at a site corresponding to S345 of SEQ ID NO: 2; and a proline to leucine mutation at a site corresponding to P410 of SEQ ID NO: 2.

The invention encompasses purified thermostable DNA polymerase having an amino acid sequence presented in SEQ ID NO: 2 from residue 1 to 776.

In one embodiment, the thermostable DNA polymerase is isolated from *Thermococcus* species JDF-3.

In another embodiment, the thermostable polymerase is isolated from a recombinant organism transformed with a vector that codes for the expression of *Thermococcus* species JDF-3 DNA polymerase.

The invention further encompasses a recombinant vector comprising the nucleotide sequence presented in SEQ ID NO: 1.

The invention further encompasses an isolated recombinant polypeptide comprising the amino acid sequence of SEQ ID NO: 2 or a functional fragment thereof.

The invention further encompasses an isolated recombinant DNA polymerase from *Thermococcus* species JDF-3 that is 3' to 5' exonuclease deficient.

In one embodiment, the isolated recombinant DNA polymerase of has an aspartic acid to threonine or alanine mutation at the amino acid corresponding to D141 of SEQ ID NO: 2 or a glutamic acid to alanine mutation at the amino acid corresponding to E143 of SEQ ID NO: 2.

In another embodiment, the isolated recombinant DNA polymerase has an aspartic acid to threonine or alanine mutation at the amino acid corresponding to D141 of SEQ ID NO: 2 and a glutamic acid to alanine mutation at the amino acid corresponding to E143 of SEQ ID NO: 2.

The invention further encompasses an isolated recombinant DNA polymerase having reduced discrimination against non-conventional nucleotides.

In one embodiment, the DNA polymerase is a Family B DNA polymerase.

In another embodiment, the DNA polymerase further comprises a mutation selected from the group consisting of: a leucine to histidine mutation at a site corresponding to L408 of SEQ ID NO: 2; a leucine to phenylalanine mutation at a site corresponding to L408 of SEQ ID NO: 2; a proline to leucine mutation at a site corresponding to P410 of SEQ ID NO: 2; and an alanine to threonine mutation at a site corresponding to A485 of SEQ ID NO: 2.

The invention further encompasses an isolated recombinant DNA polymerase having the alanine to threonine mutation at the site corresponding to A485 of SEQ ID NO: 2 further comprising a mutation selected from the group consisting of: a leucine to histidine mutation at a site corresponding to L408 of SEQ ID NO: 2; a leucine to phenylalanine mutation at a site corresponding to L408 of SEQ ID NO: 2; and a proline to leucine mutation at a site corresponding to P410 of SEQ ID NO: 2.

The invention further encompasses an isolated recombinant DNA polymerase having the a proline to leucine mutation at a site corresponding to P410 of SEQ ID NO: 2, further comprising of serine to proline mutation at a site corresponding to S345 of SEQ ID NO: 2

In another embodiment, the DNA polymerase has reduced discrimination against a non-conventional nucleotide selected from the group consisting of: dideoxynucleotides, ribonucleotides and conjugated nucleotides.

In another embodiment, conjugated nucleotide is selected from the group consisting of radiolabeled nucleotides, fluorescently labeled nucleotides, biotin labeled nucleotides, chemiluminescently labeled nucleotides and quantum dot labeled nucleotides.

The invention further encompasses an isolated recombinant Family B DNA polymerase comprising an alanine to threonine mutation at the site corresponding to A485 of SEQ ID NO: 2 or a mutation at a site corresponding to L408 or P410 of SEQ ID NO: 2, wherein the DNA polymerase has reduced discrimination against non-conventional nucleotides relative to the wild-type form of that polymerase.

In one embodiment, the Family B DNA polymerase is 3' to 5' exonuclease deficient.

In another embodiment, the Family B DNA polymerase has a mutation at an amino acid corresponding to D141 or E143 of SEQ ID NO: 2.

In another embodiment, the Family B DNA polymerase has an aspartic acid to threonine or alanine mutation at a site corresponding to D141 of SEQ ID NO: 2.

In another embodiment, the Family B DNA polymerase has a glutamic acid to alanine mutation at a site corresponding to E143 of SEQ ID NO: 2.

In another embodiment, the Family B DNA polymerase has a glutamic acid to alanine mutation at a site corresponding to E143 of SEQ ID NO: 2 and has an aspartic acid to threonine or alanine mutation at the amino acid corresponding to D141 of SEQ ID NO: 2.

In another embodiment, the Family B DNA polymerase is thermostable.

In another embodiment, the Family B DNA polymerase is archaeal.

In another embodiment, the Family B DNA polymerase comprises a leucine to histidine mutation at a site corresponding to L408 of SEQ ID NO: 2.

In another embodiment, the Family B DNA polymerase comprises a leucine to phenylalanine mutation at a site corresponding to L408 of SEQ ID NO: 2.

In another embodiment, the Family B DNA polymerase comprises a proline to leucine mutation at a site corresponding to P410 of SEQ ID NO: 2.

In another embodiment, the Family B DNA polymerase comprises an alanine to threonine mutation at a site corresponding to A485 of SEQ ID NO: 2.

In another embodiment, the Family B DNA polymerase comprising an alanine to threonine mutation at a site corresponding to A485 of SEQ ID NO: 2 comprises a leucine to histidine mutation at a site corresponding to L408 of SEQ ID NO: 2.

In another embodiment, the Family B DNA polymerase comprising an alanine to threonine mutation at a site corresponding to A485 of SEQ ID NO: 2 comprises a leucine to phenylalanine mutation at a site corresponding to L408 of SEQ ID NO: 2.

In another embodiment, the Family B DNA polymerase comprising an alanine to threonine mutation at a site corresponding to A485 of SEQ ID NO: 2 comprises a proline to leucine mutation at a site corresponding to P410 of SEQ ID NO: 2.

In another embodiment, the Family B DNA polymerase comprising a proline to leucine mutation at a site corresponding to P410 of SEQ ID NO: 2, further having a serine to proline mutation at a site corresponding to S345 of SEQ ID NO: 2.

In another embodiment, the Family B DNA polymerase comprises a serine to proline mutation at a site corresponding to S345 of SEQ ID NO: 2, and may further comprise a mutation at a site corresponding to T604 of SEQ ID NO: 2.

In another embodiment, the Family B DNA polymerase comprises a tyrosine to cysteine mutation at a site corresponding to Y497 of SEQ ID NO: 2, and may further comprise an isoleucine to valine mutation at a site corresponding to I630 of SEQ ID NO: 2.

In another embodiment, the Family B DNA polymerase comprises a glutamic acid to lysine mutation at a site corresponding to E645 of SEQ ID NO: 2.

In another embodiment, the Family B DNA polymerase comprises a glutamic acid to lysine mutation at a site corresponding to E578 of SEQ ID NO: 2, and may further comprise an arginine to methionine mutation at a site corresponding to R465 of SEQ ID NO: 2.

In another embodiment, the Family B DNA polymerase comprises a leucine to glutamine mutation at a site corresponding to L396 of SEQ ID NO: 2, and may further comprise a mutation at a site corresponding to V401, N424, P569, E617, or V640 of SEQ ID NO: 2.

In another embodiment, the Family B DNA polymerase comprises a serine to asparagine mutation at a site corresponding to S651 of SEQ ID NO: 2.

In another embodiment, the Family B DNA polymerase comprises a leucine to proline mutation at a site corresponding to L396 of SEQ ID NO: 2, and may further comprise a mutation at a site corresponding to E459 of SEQ ID NO: 2.

In another embodiment, the Family B DNA polymerase comprises a leucine to proline mutation at a site corresponding to L456 of SEQ ID NO: 2, and may further comprise a mutation at a site corresponding to E658 of SEQ ID NO: 2.

In another embodiment, the Family B DNA polymerase comprises a leucine to histidine mutation at a site corresponding to L408 of SEQ ID NO: 2, and may further comprise a mutation at a site corresponding to V437, or L478 of SEQ ID NO: 2. The L408H mutation was isolated both in the dideoxynucleotide and the dye-dideoxynucleotide screens described herein.

In another embodiment, the Family B DNA polymerase comprises an tyrosine to asparagine mutation at a site corresponding to Y496 of SEQ ID NO: 2.

In another embodiment, the Family B DNA polymerase has reduced discrimination against a non-conventional nucleotide selected from the group consisting of: dideoxynucleotides, ribonucleotides and conjugated nucleotides.

In another embodiment, the conjugated nucleotide is selected from the group consisting of radiolabeled nucleotides, fluorescently labeled nucleotides, biotin labeled nucleotides, chemiluminescently labeled nucleotides and quantum dot labeled nucleotides.

In another embodiment, an isolated recombinant DNA polymerase having reduced discrimination against non-conventional nucleotides or an isolated recombinant Family B DNA polymerase comprising an alanine to threonine mutation at the site corresponding to A485 of SEQ ID NO: 2 or a mutation at a site corresponding to L408 or P410 of SEQ ID NO: 2, wherein the DNA polymerase has reduced discrimination against non-conventional nucleotides relative to the wild-type form of that polymerase further comprises a mutation at an amino acid residue in the polymerase that corresponds to a mutation selected from the group consisting of: a Y to V mutation at amino acid 409 of SEQ ID NO: 2; an A to C, S, L, I, F, or V mutation at amino acid 485 of SEQ ID NO: 2; a Y to S mutation at amino acid 494 of SEQ ID NO: 2; a Y to L mutation at amino acid 496 of SEQ ID NO: 2; and an A to Y mutation at amino acid 490 of SEQ ID NO: 2.

In another embodiment, an isolated recombinant DNA polymerase having reduced discrimination against non-conventional nucleotides or an isolated recombinant Family B DNA polymerase comprising an alanine to threonine mutation at the site corresponding to A485 of SEQ ID NO: 2 or a mutation at a site corresponding to L408 or P410 of SEQ ID NO: 2, wherein the DNA polymerase has reduced discrimination against non-conventional nucleotides relative to the wild-type form of that polymerase further comprises a mutation at an amino acid of the polymerase corresponding to one of amino acids 483 to 496, inclusive, of SEQ ID NO: 2.

In one embodiment, the mutation is at an amino acid of the polymerase corresponding to one of amino acids 485, 490, 494, or 496 of SEQ ID NO: 2.

The invention further encompasses an isolated recombinant Family B DNA polymerase comprising an alanine to threonine mutation at an amino acid corresponding to A485T of SEQ ID NO: 2 and at least one substitution in the polymerase of an amino acid corresponding to L408, Y409, or P410, respectively, of SEQ ID NO: 2.

The invention further encompasses an isolated recombinant Family B DNA polymerase comprising an amino acid other than A at an amino acid of the polymerase corresponding to A485 of SEQ ID NO: 2, and at least one substitution in the polymerase of an amino acid corresponding to L408, Y409, or P410, respectively, of SEQ ID NO: 2.

The invention further encompasses a recombinant vector comprising a nucleic acid sequence encoding the Family B DNA polymerase.

The invention further encompasses a method of labeling a complementary strand of DNA, the method comprising the step of contacting a template DNA molecule with a recombinant Family B DNA polymerase from *Thermococcus* species JDF-3, wherein the DNA polymerase has reduced discrimination against non-conventional nucleotides, and a non-conventional nucleotide, under conditions and for a time sufficient to permit the DNA polymerase to synthesize a complementary DNA strand and to incorporate the non-conventional nucleotide into the synthesized complementary DNA strand.

The invention further encompasses a method of labeling a complementary strand of DNA, the method comprising the step of contacting a template DNA molecule with a recombinant Family B DNA polymerase comprising an alanine to threonine mutation at a site corresponding to A485 of SEQ ID NO: 2 or a mutation at a site corresponding to L408 or P410 of SEQ ID NO: 2, wherein the DNA polymerase has reduced discrimination against non-conventional nucleotides, and a non-conventional nucleotide, under conditions and for a time sufficient to permit the DNA polymerase to synthesize a complementary DNA strand and to incorporate the non-conventional nucleotide into the synthesized complementary DNA strand.

In one embodiment, the recombinant Family B DNA polymerase is 3' to 5' exonuclease deficient.

In another embodiment, the recombinant Family B polymerase comprises a leucine to histidine mutation at a site corresponding to amino acid L408 of SEQ ID NO: 2.

In another embodiment, the recombinant Family B polymerase comprises a leucine to phenylalanine mutation at a site corresponding to amino acid L408 of SEQ ID NO: 2.

In another embodiment, the recombinant Family B polymerase comprises a proline to leucine mutation at a site corresponding to amino acid P410 of SEQ ID NO: 2.

In another embodiment, the recombinant Family B polymerase comprises an alanine to threonine mutation at a site corresponding to amino acid A485 of SEQ ID NO: 2.

In another embodiment, the recombinant Family B polymerase comprising an alanine to threonine mutation at a site corresponding to amino acid A485 of SEQ ID NO: 2 comprises a leucine to histidine mutation at an amino acid corresponding to L408 of SEQ ID NO: 2.

In another embodiment, the recombinant Family B polymerase comprising an alanine to threonine mutation at a site corresponding to amino acid A485 of SEQ ID NO: 2 comprises a leucine to phenylalanine mutation at an amino acid corresponding to L408 of SEQ ID NO: 2.

In another embodiment, the recombinant Family B polymerase comprising an alanine to threonine mutation at a site corresponding to amino acid A485 of SEQ ID NO: 2 comprises a proline to leucine mutation at an amino acid corresponding to P410 of SEQ ID NO: 2.

In another embodiment, the recombinant Family B polymerase has reduced discrimination against a non-conventional nucleotide selected from the group consisting of: dideoxynucleotides, ribonucleotides, and conjugated nucleotides.

In another embodiment, the conjugated nucleotide is selected from the group consisting of radiolabeled nucleotides, fluorescently labeled nucleotides, biotin labeled nucleotides, chemiluminescently labeled nucleotides and quantum dot labeled nucleotides.

The invention further encompasses a method of sequencing DNA comprising the steps of contacting a DNA strand to be sequenced with a sequencing primer, a recombinant Family B DNA polymerase from *Thermococcus* species JDF-3, wherein the DNA polymerase has reduced discrimination against non-conventional nucleotides, and a chain-terminating nucleotide analog, under conditions that permit the DNA polymerase to synthesize a complementary DNA strand, and to incorporate nucleotides into the synthesized complementary DNA strand, wherein incorporation of a chain-terminating nucleotide analog results in the termination of chain elongation, such that the nucleotide sequence of the template DNA strand is determined.

The invention further encompasses a method of sequencing DNA comprising the steps of contacting a DNA strand to be sequenced with a sequencing primer, a recombinant Family B DNA polymerase comprising an alanine to threonine mutation at a site corresponding to A485 of SEQ ID NO: 2 or a mutation at a site corresponding to L408, S345 or P410 of SEQ ID NO: 2, where the DNA polymerase has reduced discrimination against non-conventional nucleotides, and a chain-terminating nucleotide analog, under conditions that permit the DNA polymerase to synthesize a complementary DNA strand, and to incorporate nucleotides into the synthesized complementary DNA strand, wherein incorporation of a chain-terminating nucleotide analog results in the termination of chain elongation, such that the nucleotide sequence of the template DNA strand is determined.

In one embodiment, the recombinant DNA polymerase is deficient in 3' to 5' exonuclease activity.

In another embodiment, the recombinant Family B polymerase has a leucine to histidine mutation at a site corresponding to amino acid L408 of SEQ ID NO: 2.

In another embodiment, the recombinant Family B polymerase has a leucine to phenylalanine mutation at a site corresponding to amino acid L408 of SEQ ID NO: 2.

In another embodiment, the recombinant Family B polymerase has a proline to leucine mutation at a site corresponding to amino acid P410 of SEQ ID NO: 2.

In another embodiment, the Family B DNA polymerase comprising a proline to leucine mutation at a site corresponding to P410 of SEQ ID NO: 2, further having a serine to proline mutation at a site corresponding to S345 of SEQ ID NO: 2.

In another embodiment, the recombinant Family B polymerase has an alanine to threonine mutation at a site corresponding to amino acid A485 of SEQ ID NO: 2.

In another embodiment, the recombinant Family B polymerase having an alanine to threonine mutation at a site corresponding to amino acid A485 of SEQ ID NO: 2 has a leucine to histidine mutation at a site corresponding to L408 of SEQ ID NO: 2.

In another embodiment, the recombinant Family B polymerase having an alanine to threonine mutation at a site corresponding to amino acid A485 of SEQ ID NO: 2 has a leucine to phenylalanine mutation at a site corresponding to L408 of SEQ ID NO: 2.

In another embodiment, the recombinant Family B polymerase having an alanine to threonine mutation at a site corresponding to amino acid A485 of SEQ ID NO: 2 has a proline to leucine mutation at a site corresponding to P410 of SEQ ID NO: 2.

In another embodiment, the chain-terminating nucleotide analog is a dideoxynucleotide.

In another embodiment, the dideoxynucleotide is detectably labeled.

In another embodiment, the dideoxynucleotide is fluorescently labeled.

In another embodiment, the dideoxynucleotide is labeled with a moiety selected from the group consisting of fluorescein and rhodamine.

The invention also encompasses a kit for performing the methods disclosed herein.

The invention also encompasses methods of making a recombinant DNA polymerase as disclosed here, comprising culturing a host cell containing a nucleic acid sequence encoding said polymerase under conditions which permit production of said DNA polymerase.

The invention encompasses a mixture of a mutant DNA polymerase described herein and another DNA polymerase such as Taq DNA polymerase (preferably the mutant form, F667Y). Such a mixture is useful in that it may increase signal uniformity generated from polymerization of a labeled nucleotide into a synthetic nucleotide.

As used herein, "discrimination" refers to the tendency of DNA polymerase to not incorporate non-conventional nucleotides into a nascent DNA polymer. DNA polymerase has the ability to sense nucleotide structure, including but not limited to nucleotide base complementarity, and structural features of the sugar and heterocyclic base, thereby allowing DNA polymerase to preferentially utilize conventional deoxynucleotides rather than non-conventional nucleotides for incorporation into a nascent polymer. DNA polymerase strongly prefers to incorporate the conventional deoxynucleotides dATP, dCTP, dGTP and TTP into DNA polymers; the polymerase is unlikely to progress with an unconventional nucleotide in its binding pocket.

As used herein, "reduced discrimination" refers to a reduction of at least 50% in the tendency of a DNA polymerase to exclude a non-conventional nucleotide from (that is, to not incorporate non-conventional nucleotides into) a nascent DNA polymer, relative to a parental or wild type DNA polymerase which does not exhibit reduced discrimination. The preference of DNA polymerase to incorporate the conventional deoxynucleotides dATP, dCTP, dGTP and TTP rather than non-conventional nucleotides into DNA polymers is thereby reduced compared to the natural level of preference, such that non-conventional nucleotides are more readily incorporated into DNA polymers by DNA polymerase. According to the invention, a polymerase exhibiting reduced discrimination will exhibit reduced discrimination against at least one non-conventional nucleotides, but may not exhibit reduced discrimination against all non-conventional nucleotides.

According to the invention, discrimination is quantitated by measuring the concentration of a non-conventional nucleotide required to inhibit the incorporation of the corresponding conventional nucleotide by 50%. This concentration is referred to herein as the "$I_{50\%}$" for a non-conventional nucleotide. Discrimination against a given non-conventional nucleotide is "reduced" if the $I_{50\%}$ for that non-conventional nucleotide is reduced by at least two fold (50%) relative to an identical assay containing, in place of the mutant DNA polymerase, a parental DNA polymerase.

Alternatively, reduced discrimination may be quantitated by determining the amount of a non-conventional nucleotide (for example, a dideoxynucleotide, ribonucleotide, or cordycepin) required in a reaction with a mutant polymerase having reduced discrimination to generate a sequencing ladder identical to a sequencing ladder produced using the wild-type or parental enzyme. The sequencing ladder can be examined, for example, in the range of 1 to 400 bases from the primer terminus, and the ladders will be identical in the number of extension products generated as well as the lengths of extension products generated in the sequencing reaction. For this type of assay, a constant amount of dNTPs and varying amounts of non-conventional nucleotides are used to generate a sequencing ladder with both the wild-type (or parental) enzyme and the mutant polymerase (for ribonucleotides, a sequencing ladder is generated by alkali cleavage of the polymerization products). See Gardner & Jack, 1999, supra. A mutant exhibits reduced discrimination if it requires at least two-fold (50%) less, five-fold (80%) less, ten-fold (100%) less, etc. of the amount of the non-conventional nucleotide used by the wild-type or parental polymerase to produce a sequencing ladder identical (with respect to the number and length of extension products generated) to that generated by the wild-type or parental enzyme.

As used herein, the term "parental" or "progenitor" refers to a polymerase used as the starting material in generating a mutant polymerase having reduced discrimination. The term "parental" is meant to encompass not only a so-called "wild-type" enzyme as it occurs in nature, but also intermediate forms, for example, an exonuclease deficient enzyme that is used as the starting material for generating an enzyme with reduced discrimination against non-conventional nucleotides.

As used herein, "non-conventional nucleotide" refers to a) a nucleotide structure that is not one of the four conventional deoxynucleotides dATP, dCTP, dGTP, and TTP recognized by and incorporated by a DNA polymerase, b) a synthetic nucleotide that is not one of the four conventional deoxynucleotides in (a), c) a modified conventional nucleotide, or d) a ribonucleotide (since they are not normally recognized or incorporated by DNA polymerases) and modified forms of a ribonucleotide. Non-conventional nucleotides include but are not limited to those listed in Table III, which are commercially available, for example, from New England Nuclear. Any one of the above non-conventional nucleotides may be a "conjugated nucleotide", which as used herein refers to nucleotides bearing a detectable label, including but not limited to a fluorescent label, isotope, chemiluminescent label, quantum dot label, antigen, or affinity moiety.

As used herein, the term "cell", "cell line" and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, the term "organism transformed with a vector" refers to an organism carrying a recombinant gene construct.

As used herein, "thermostable" refers to a property of a DNA polymerase, such that the enzyme active at elevated temperatures and is resistant to DNA duplex-denaturing temperatures in the range of about 93° C. to about 97° C. "Active" means the enzyme retains the ability to effect primer extension reactions when subjected to elevated or denaturing temperatures for the time necessary to effect denaturation of double-stranded nucleic acids. Elevated temperatures as used herein refer to the range of about 70° C. to about 75° C., whereas non-elevated temperatures as used herein refer to the range of about 35° C. to about 50° C.

As used herein, "archaeal" refers to an organism or to a DNA polymerase from an organism of the kingdom Archaea As used herein, "sequencing primer" refers to an oligonucleotide, whether natural or synthetic, which serves as a point of initiation of nucleic acid synthesis by a polymerase following annealing to a DNA strand to be sequenced. A primer is typically a single-stranded oligodeoxyribonucleotide. The appropriate length of a primer depends on the intended use of the primer, but for DNA sequencing applications typically ranges from about 15 to about 40 nucleotides in length.

As used herein, "Family B DNA polymerase" refers to any DNA polymerase that is classified as a member of the Family B DNA polymerases, where the Family B classification is based on structural similarity to E. coli DNA polymerase II. The Family B DNA polymerases, formerly known as α-family polymerases, include, but are not limited to those listed as such in Table I.

As used herein, "Family A DNA polymerase" refers to any DNA polymerase that is classified as a member of the Family A DNA polymerases, where the Family A classification is based on structural similarity to E. coli DNA polymerase I. Family A DNA polymerases include, but are not limited to those listed as such in Table I.

As used herein, "3' to 5' exonuclease deficient" or "3' to 5' exo⁻" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, or a "substantial" lack of activity. "Substantial" lack of activity means that the 3' exonuclease activity of the mutant polymerase relative to the parental polymerase is 0.03%, and also may be 0.05%, 0.1%, 1%, 5%, 10%, or 20%, but is not higher than 50% of the 3' exonuclease activity of the parental or wild type polymerase.

As used herein, "mutation" refers to a change introduced into a starting parental DNA sequence that changes the amino acid sequence encoded by the DNA. The consequences of a mutation include but are not limited to the creation of a new character, property, function, or trait not found in the protein encoded by the parental DNA.

As used herein, "wild-type" refers to the typical state of an organism, strain, gene, protein or characteristic as it occurs in nature. The wild-type is therefore the natural state that is distinguished from a mutant, which was derived from the wild type by introduction of change(s) to the wild-type.

As used herein, "corresponding" refers to sequence similarity in a comparison of two or more nucleic acids or polypeptides, where functionally equivalent domains or sub-sequences are identified; such functionally equivalent domains or sub-sequences or amino acids within such a domain or sub-sequence are said to "correspond". That is, two or more sequences are compared through a comparative alignment analysis in which an entire sequence is examined for regions of sequence that are similar or identical, and thus regions likely to be functionally equivalent to regions from the other sequence(s) are identified.

As used herein in reference to comparisons of an amino acid, amino acid sequence, or protein domain, the term "similar" refers to amino acids or domains that although not identical, represent "conservative" differences. By "conservative" is meant that the differing amino acid has like characteristics with the amino acid in the corresponding or reference sequence. Typical conservative substitutions are among Ala, Val, Leu and Ile; among Ser and Thr; among the acidic residues Asp and Glu; among Asn and Gln; and among the basic residues Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "functionally equivalent" means that a given motif, region, or amino acid within a motif or region performs the same function with regard to the overall function of the enzyme as a motif, region or amino acid within a motif or region performs in another enzyme.

As used herein, "chain terminating nucleotide analog" refers to a nucleotide analog that once incorporated cannot serve as a substrate for subsequent extension by a DNA polymerase, thereby terminating the elongation of a DNA polymer by a DNA polymerase. Such a nucleotide analog typically lacks a hydroxyl group on its sugar moiety to which DNA polymerase can synthesize a phosphodiester bond with an incoming nucleotide. Chain terminating nucleotide analogs are a subset of non-conventional nucleotides, and include but are not limited to dideoxynucleotides.

As used herein, "detectably labeled" refers to a structural modification that incorporates a functional group (label) that can be readily detected by various means. Compounds that can be detectably labeled include but are not limited to nucleotide analogs. Detectable nucleotide analog labels include but are not limited to fluorescent compounds, isotopic compounds, chemiluminescent compound, quantum dot labels, biotin, enzymes, electron-dense reagents, and haptens or proteins for which antisera or monoclonal antibodies are available. The various means of detection include but are not limited to spectroscopic, photochemical, biochemical, immunochemical, or chemical means.

As used herein in reference to a polynucleotide or polypeptide, the term "isolated" means that a naturally occurring sequence has been removed from its normal cellular environment or is synthesized in a non-natural environment (e.g., artificially synthesized). Thus, the sequence may be in a cell-free solution or placed in a different cellular environment. The term does not imply that the sequence is the only nucleotide or polypeptide chain present, but that it is essentially free (about 90–95% pure at least) of non-nucleotide or non-polypeptide material, respectively, naturally associated with it.

As used herein, the term "recombinant" refers to a polynucleotide or polypeptide that is altered by genetic engineering (i.e., by modification or manipulation of the genetic material encoding that polynucleotide or polypeptide).

The invention encompasses full length mutant DNA polymerases, as described herein, as well as a functional fragment of a mutant polymerase, that is, a fragment of a DNA polymerase that is less than the entire amino acid sequence of the mutant polymerase and retains the ability, under at least one set of conditions, to catalyze the polymerization of a polynucleotide. Such a functional fragment may exist as a separate entity, or it may be a constituent of a larger polypeptide, such as a fusion protein.

As used herein, the term "complementary DNA strand" refers to that DNA molecule synthesized from a template DNA molecule by a DNA polymerase in a primer extension reaction.

As used herein, the term "template DNA molecule" refers to that strand of a nucleic acid from which a complementary nucleic acid strand is synthesized by a DNA polymerase, for example, in a primer extension reaction.

Further features and advantages of the invention will become more fully apparent in the following description of the embodiments and drawings thereof, and from the claims.

BRIEF DESCRIPTION OF THE DRAWINGS

FIG. 1 shows the DNA sequence encoding *Thermococcus* species JDF-3 DNA polymerase (intein removed) (SEQ ID NO: 1).

FIG. 2 shows the amino sequence of *Thermococcus* species JDF-3 DNA polymerase (intein removed) (SEQ ID NO: 2).

FIG. 3 shows the amino acid sequence of the genomic clone encoding *Thermococcus* species JDF-3 DNA polymerase (SEQ ID NO: 3). The position of an intein, removed by post-translational processing, is shown.

FIG. 4 shows the DNA sequence of the genomic clone encoding *Thermococcus* species JDF-3 DNA polymerase (SEQ ID NO: 4). DNA sequences are shown which correspond to 5' and 3' untranslated regions, polymerase-coding regions (exteins), and an intein-coding region.

FIG. 14 shows the sequence alignment of dye-dideoxynucleotide selected JDF-3 mutants (amino acids 301–480). Underlined nucleic acid residues indicate the location of mutations. The mutation S345P is one of two mutations present in mutant 28. Sequence assignments are as follows: 4: SEQ ID NO: 21; 10: SEQ ID NO: 22; 13: SEQ ID NO: 23; 16: SEQ ID NO: 24; 18: SEQ ID NO: 25; 19: SEQ ID NO: 26; 28: SEQ ID NO: 27; 34: SEQ ID NO: 28; 41: SEQ ID NO: 29; 33: SEQ ID NO: 30; 48: SEQ ID NO: 31; 55: SEQ ID NO: 32; 64: SEQ ID NO: 33; Jdf3: SEQ ID NO: 34.

FIG. 15 shows the sequence alignment of dye-dideoxynucleotide selected JDF-3 (amino acids 481–660). Underlined nucleic acid residues indicate the location of mutations. Sequence assignments are as follows: 4: SEQ ID NO: 35; 10: SEQ ID NO: 36; 13: SEQ ID NO: 37; 16: SEQ ID NO: 38; 18: SEQ ID NO: 39; 19: SEQ ID NO: 40; 28: SEQ ID NO: 41; 34: SEQ ID NO: 42; 41: SEQ ID NO: 43; 33: SEQ ID NO: 44; 48: SEQ ID NO: 45; 55: SEQ ID NO: 46; 64: SEQ ID NO: 47; Jdf3: SEQ ID NO: 48.

DESCRIPTION

Figure 5:
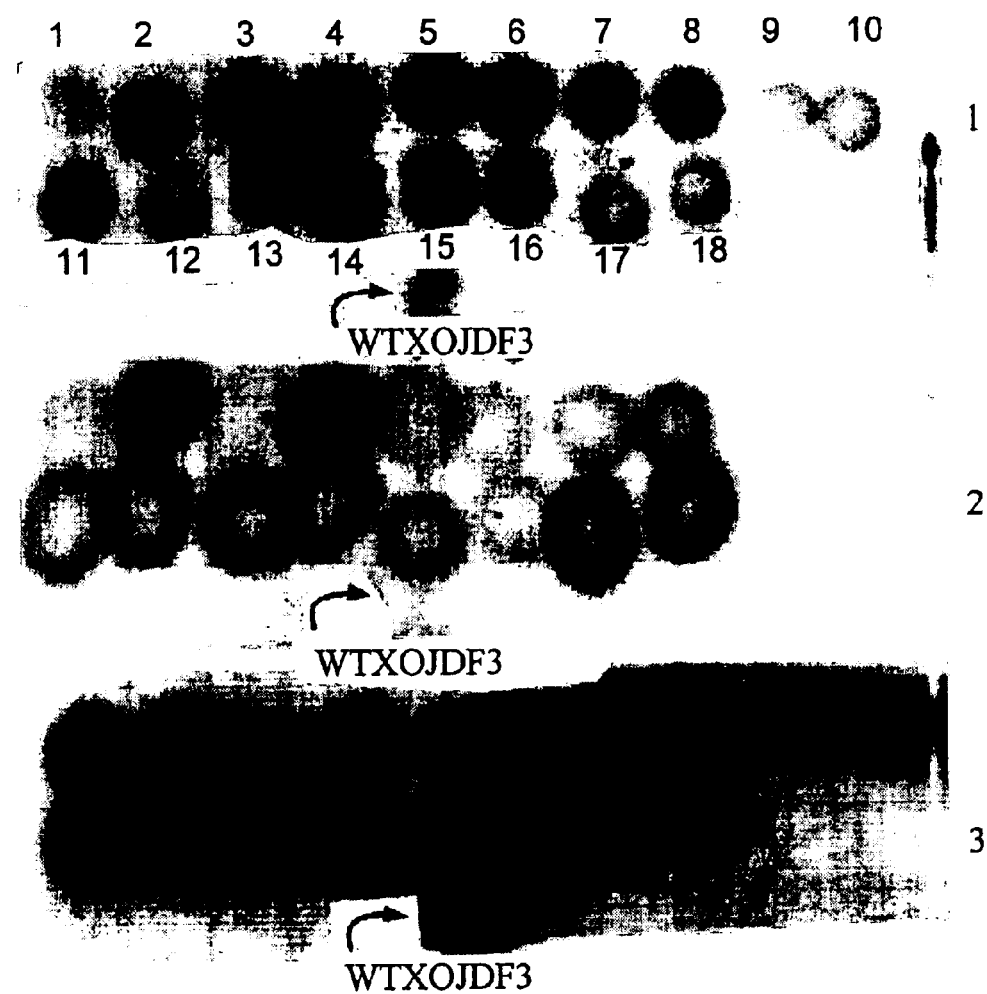
FIG. 5 shows nucleotide incorporation by JDF-3 mutants. Lambda phage clones which incorporated $^{33}$P-labeled ddNTPs in the primary library screen were rescreened to assess $^{33}$P-ddNTP incorporation in the presence of: (panel 1) 0.5 mM $MnCl_2$ or (panel 2) 1.5 mM $MgCl_2$. Polymerase activity was measured using $^{33}$P-dNTPs in the presence of 1.5 mM $MgCl_2$ (panel 3). Nucleotide utilization is shown for clones 1–18 and for the parental #550 clone.

The invention is based on the discovery of Family B DNA polymerases that bear one or more genetic alterations resulting in reduced discrimination against non-conventional nucleotides relative to their unmodified wild-type forms. All references described herein are incorporated by reference herein in their entirety.

Family B DNA Polymerase Exhibiting Reduced Discrimination Against Non-Conventional Nucleotides A. DNA Polymerases Useful According to the Invention According to the invention, DNA polymerases of Family B may be mutated to generate enzymes exhibiting reduced discrimination against non-conventional nucleotides. Table I includes a non-limiting list of known DNA polymerases categorized by family.

TABLE I

DNA POLYMERASES BY FAMILY

| | Reference |
|---|---|
| FAMILY A DNA POLYMERASES | |
| Bacterial DNA Polymerases | |
| a) *E. coli* DNA polymerase I | (1) |
| b) *Streptococcus pneumoniae* DNA polymerase I | (2) |
| c) *Thermus aquaticus* DNA polymerase I | (3) |
| d) *Thermus flavus* DNA polymerase I | (4) |
| e) *Thermotoga maritima* DNA polymerase I | |
| Bacteriophage DNA Polymerases | |
| a) T5 DNA polymerase | (5) |
| b) T7 DNA polymerase | (6) |
| c) Spo1 DNA polymerase | (7) |
| d) Spo2 DNA polymerase | (8) |
| Mitochondrial DNA polymerase | |
| Yeast Mitochondrial DNA polymerase II | (9, 10, 11) |
| FAMILY B DNA POLYMERASES | |
| Bacterial DNA polymerase | |
| *E. coli* DNA polymerase II | (15) |

TABLE I-continued

DNA POLYMERASES BY FAMILY

| | Reference |
|---|---|
| Bacteriophage DNA polymerase | |
| a) PRD1 DNA polymerase | (16, 17) |
| b) φ29 DNA polymerase | (18) |
| c) M2 DNA polymerase | (19) |
| d) T4 DNA polymerase | (20) |
| Archaeal DNA polymerase | |
| a) *Thermococcus litoralis* DNA polymerase (Vent) | (21) |
| b) *Pyrococcus furiosus* DNA polymerase | (22) |
| c) *Sulfolobus solfataricus* DNA polymerase | (23) |
| d) *Thermococcus gorgonarius* DNA polymerase | (64) |
| e) *Thermococcus* species TY | (65) |
| f) *Pyrococcus* species strain KODI | (66) |
| g) *Sulfolobus acidocaldarius* | (67) |
| h) *Thermococcus* species 9°N-7 | (68) |
| i) *Pyrodictium occultum* | (69) |
| j) *Methanococcus voltae* | (70) |
| k) *Desulfurococcus* strain TOK (D. Tok Pol) | (71) |
| Eukaryotic Cell DNA polymerase | |
| (1) DNA polymerase alpha | |
| a) Human DNA polymerase (alpha) | (24) |
| b) *S. cerevisiae* DNA polymerase (alpha) | (25) |
| c) *S. pombe* DNA polymerase I (alpha) | (26) |
| d) *Drosophila melanogaster* DNA polymerase (alpha) | (27) |
| e) *Trypanosoma brucei* DNA polymerase (alpha) | (28) |
| (2) DNA polymerase delta | |
| a) Human DNA polymerase (delta) | (29, 30) |
| b) Bovine DNA polymerase (delta) | (31) |
| c) *S. cerevisiae* DNA polymerase III (delta) | (32) |
| d) *S. pombe* DNA polymerase III (delta) | (33) |
| e) *Plasmodiun falciparum* DNA polymerase (delta) | (34) |
| (3) DNA polymerase epsilon | |
| *S. cerevisiae* DNA polymerase II (epsilon) | (35) |
| (4) Other eukaryotic DNA polymerase | |
| *S. cerevisiae* DNA polymerase Rev3 | (36) |
| Viral DNA polymerases | |
| a) Herpes Simplex virus type 1 DNA polymerase | (37) |
| b) Equine herpes virus type 1 DNA polymerase | (38) |
| c) Varicella-Zoster virus DNA polymerase | (39) |
| d) Epstein-Barr virus DNA polymerase | (40) |
| e) Herpesvirus saimiri DNA polymerase | (41) |
| f) Human cytomegalovirus DNA polymerase | (42) |
| g) Murine cytomegalovirus DNA polymerase | (43) |
| h) Human herpes virus type 6 DNA polymerase | (44) |
| i) Channel Catfish virus DNA polymerase | (45) |
| j) Chlorella virus DNA polymerase | (46) |
| k) Fowlpox virus DNA polymerase | (47) |
| l) Vaccinia virus DNA polymerase | (48) |
| m) Choristoneura biennis DNA polymerase | (49) |
| n) Autographa california nuclear polymerase virus (AcMNPV) DNA polymerase | (50) |
| o) Lymantria dispar nuclear polyhedrosis virus DNA polymerase | (51) |
| p) Adenovirus-2 DNA polymerase | (52) |
| q) Adenovirus-7 DNA polymerase | (53) |
| r) Adenovirus-12 DNA polymerase | (54) |
| Eukaryotic linear DNA plasmid encoded DNA polymerases | |
| a) S-1 Maize DNA polymerase | (55) |
| b) kalilo neurospora intermedia DNA polymerase | (56) |
| c) pAI2 ascobolus immersus DNA polymerase | (57) |
| d) pCLK1 *Claviceps purpurea* DNA polymerase | (58) |
| e) maranhar neurospora crassa DNA polymerase | (59) |
| f) pEM *Agaricus bitorquis* DNA polymerase | (60) |
| g) pGKL1 *Kluyveromyces lactis* DNA polymerase | (61) |
| h) pGKL2 *Kluyveromyces lactis* DNA polymerase | (62) |
| i) pSKL *Saccharomyces kluyveri* DNA polymerase | (63) |

B. Plasmids

The starting sequences for the generation of Family B DNA polymerases according to the invention may be contained in a plasmid vector. A non-limiting list of cloned Family B DNA polymerases and their GenBank Accession numbers are listed in Table II.

TABLE II

Accession Information for Cloned Family B Polymerases

Vent *Thermococcus litoralis*
ACCESSION AAA72101
PID g348689
VERSION AAA72101.1 GI:348689
DBSOURCE locus THCVDPE accession M74198.1
THEST *THERMOCOCCUS* SP. (STRAIN TY)
ACCESSION O33845
PID g3913524
VERSION O33845 GI:3913524
DBSOURCE swissprot: locus DPOL__THEST, accession O33845
Pab *Pyrococcus abyssi*
ACCESSION P77916
PID g3913529
VERSION P77916 GI:3913529
DBSOURCE swissprot: locus DPOL__PYRAB, accession P77916
PYRHO *Pyrococcus horikoshii*
ACCESSION O59610
PID g3913526
VERSION O59610 GI:3913526
DBSOURCE swissprot: locus DPOL__PYRHO, accession O59610
PYRSE *PYROCOCCUS* SP. (STRAIN GE23)
ACCESSION P77932
PID g3913530
VERSION P77932 GI:3913530
DBSOURCE swissprot: locus DPOL__PYRSE, accession P77932
DeepVent *Pyrococcu* sp.
ACCESSION AAA67131
PID g436495
VERSION AAA67131.1 GI:436495
DBSOURCE locus PSU00707 accession U00707.1
Pfu *Pyrococcus furiosus*
ACCESSION P80061
PID g399403
VERSION P80061 GI:399403
DBSOURCE swissprot: locus DPOL__PYRFU, accession P80061
JDF-3 *Thermococcus* sp.
Unpublished
Baross gi|2097756|pat|US|5602011|12 Sequence 12 from patent US 5602011
9degN *THERMOCOCCUS* SP. (STRAIN 9ON-7).
ACCESSION Q56366
PID g3913540
VERSION Q56366 GI:3913540
DBSOURCE swissprot: locus DPOL__THES9, accession Q56366
KOD *Pyrococcus* sp.
ACCESSION BAA06142
PID g1620911
VERSION BAA06142.1 GI:1620911
DBSOURCE locus PYWKODPOL accession D29671.1
Tgo *Thermococcus gorgonarius*.
ACCESSION 4699806
PID g4699806
VERSION GI:4699806
DBSOURCE pdb: chain 65, release Feb. 23, 1999
THEFM *Thermococcus fumicolans*
ACCESSION P74918
PID g3913528
VERSION P74918 GI:3913528
DBSOURCE swissprot: locus DPOL__THEFM, accession P74918
METTH *Methanobacterium thermoautotrophicum*
ACCESSION O27276
PID g3913522
VERSION O27276 GI:3913522
DBSOURCE swissprot: locus DPOL__METTH, accession O27276
Metja *Methanococcus jannaschii*
ACCESSION Q58295
PID g3915679
VERSION Q58295 GI:3915679
DBSOURCE swissprot: locus DPOL__METJA, accession Q58295
POC *Pyrodictium occultum*
ACCESSION B56277
PID g1363344
VERSION B56277 GI:1363344
DBSOURCE pir: locus B56277

TABLE II-continued

Accession Information for Cloned Family B Polymerases

ApeI *Aeropyrum pernix*
ACCESSION BAA81109
PID  g5105797
VERSION BAA81109.1 GI:5105797
DBSOURCE locus AP000063 accession AP000063.1
ARCFU *Archaeoglobus fulgidus*
ACCESSION O29753
PID  g3122019
VERSION O29753 GI:3122019
DBSOURCE swissprot: locus DPOL_ARCFU, accession O29753
*Desulfurococcus* sp. Tok.
ACCESSION 6435708
PID  g64357089
VERSION GT:6435708
DBSOURCE pdb. chain 65, release Jun. 2, 1999

Plasmids acceptable for the expression of modified forms of Family B DNA polymerases may be selected from a large number known in the art by one of skill in the art. A plasmid vector for expression of a modified DNA polymerase according to the invention will preferably comprise sequences directing high level expression of a DNA polymerase, and will more preferably comprise sequences directing inducible, high level expression of a DNA polymerase. As one example of an inducible high level expression system, plasmids placing a modified DNA polymerase coding sequence according to the invention under the control of a bacteriophage T7 promoter may be introduced to bacteria containing an inducible T7 RNA polymerase gene within their chromosome. Induction of the T7 RNA polymerase gene subsequently induces high level expression of the T7 promoter-driven modified DNA polymerase gene (see for example, Gardner & Jack, Nucleic Acids Res. 27: 2545).

C. Mutagenesis

The cloned wild-type form of a Family B DNA polymerase may be mutated to generate forms exhibiting reduced discrimination against non-conventional nucleotides by a number of methods.

First, methods of random mutagenesis which will result in a panel of mutants bearing one or more randomly-situated mutations exist in the art. Such a panel of mutants may then be screened for those exhibiting reduced discrimination relative to the wild-type polymerase (see "Methods of Evaluating Mutants for Reduced Discrimination", below). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Second, there are a number of site-directed mutagenesis methods known in the art which allow one to mutate a particular site or region in a straightforward manner. There are a number of kits available commercially for the performance of site-directed mutagenesis, including both conventional and PCR-based methods. Examples include the EXSITE™ PCR-Based Site-directed Mutagenesis Kit available from Stratagene (Catalog No. 200502; PCR based) and the QUIKCHANGE™ Site-directed mutagenesis Kit from Stratagene (Catalog No. 200518; non-PCR-based), and the CHAMELEON® double-stranded Site-directed mutagenesis kit, also from Stratagene (Catalog No. 200509).

Older methods of site-directed mutagenesis known in the art relied upon sub-cloning of the sequence to be mutated into a vector, such as an M13 bacteriophage vector, that allows the isolation of single-stranded DNA template. In these methods one annealed a mutagenic primer (i.e., a primer capable of annealing to the site to be mutated but bearing one or mismatched nucleotides at the site to be mutated) to the single-stranded template and then polymerized the complement of the template starting from the 3' end of the mutagenic primer. The resulting duplexes were then transformed into host bacteria and plaques were screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25–30 down to 5–10 without dramatically reducing product yield. Second, the restriction endonuclease DpnI (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase. The method is described in detail as follows:

PCR-based Site Directed Mutagenesis of the 3'–5' Exonuclease domain

Plasmid template DNA (approximately 0.5 pmole) is added to a PCR cocktail containing: 1× mutagenesis buffer (20 mM Tris HCl, pH 7.5; 8 mM MgCl2; 40 ug/ml BSA); 12–20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 uM each dNTP, 2.5 U Taq DNA polymerase, and 2.5 U of Taq Extender (Available from Stratagene; See Nielson et al. (1994) Strategies 7: 27, and U.S. Pat. No. 5,556,772). The PCR cycling is performed as follows: 1 cycle of 4 min at 94° C., 2 min at 50° C. and 2 min at 72° C.; followed by 5–10 cycles of 1 min at 94° C., 2 min at 54°

C. and 1 min at 72° C. The parental template DNA and the linear, PCR-generated DNA incorporating the mutagenic primer are treated with DpnI (10 U) and Pfu DNA polymerase (2.5U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2–4 U) is added. The ligation is incubated for greater than 60 min at 37° C. Finally, the treated solution is transformed into competent *E. coli* according to standard methods.

D. Non-Conventional Nucleotides Useful According to the Invention

There is a wide variety of non-conventional nucleotides available in the art. Any or all of them are contemplated for use with a DNA polymerase of the invention. A non-limiting list of such non-conventional nucleotides is presented in Table III.

TABLE III

Non-Conventional Nucleotides

DIDEOXYNUCLEOTIDE ANALOGS

| Fluorescein Labeled | Fluorophore Labeled |
| --- | --- |
| Fluorescein-12-ddCTP | Eosin-6-ddCTP |
| Fluorescein-12-ddUTP | Coumarin-5-ddUTP |
| Fluorescein-12-ddATP | Tetramethylrhodamine-6-ddUTP |
| Fluorescein-12-ddGTP | Texas Red-5-ddATP |
| Fluorescein-N6-ddATP | LISSAMINE ™-rhodamine-5-ddGTP |

| FAM Labeled | TAMRA Labeled |
| --- | --- |
| FAM-ddUTP | TAMRA-ddUTP |
| FAM-ddCTP | TAMRA-ddCTP |
| FAM-ddATP | TAMRA-ddATP |
| FAM-ddGTP | TAMRA-ddGTP |

| ROX Labeled | JOE Labeled |
| --- | --- |
| ROX-ddUTP | JOE-ddUTP |
| ROX-ddCTP | JOE-ddCTP |
| ROX-ddATP | JOE-ddATP |
| ROX-ddGTP | JOE-ddGTP |

| R6G Labeled | R110 Labeled |
| --- | --- |
| R6G-ddUTP | R110-ddUTP |
| R6G-ddCTP | R110-ddCTP |
| R6G-ddATP | R110-ddATP |
| R6G-ddGTP | R110-ddGTP |

| BIOTIN Labeled | DNP Labeled |
| --- | --- |
| Biotin-N6-ATP | DNP-N6-ddATP |

DEOXYNUCLEOTIDE ANALOGS

| TTP Analogs | dATP-Analogs |
| --- | --- |
| Fluorescein-12-dUTP | Coumarin-5-dATP |
| Coumarin-5-dUTP | Diethylaminocoumarin-5-dATP |
| Tetramethylrhodamine-6-dUTP | Fluorescein-12-dATP |
| Tetraethylrhodamine-6-dUTP | Fluorescein Chlorotriazinyl-4-dATP |
| Texas Red-5-dUTP | LISSAMINE ™-rhodamine-5-dATP |
| LISSAMINE ™-rhodamine-5-dUTP | Naphthofluorescein-5-dATP |

TABLE III-continued

Non-Conventional Nucleotides

| | |
| --- | --- |
| Naphthofluorescein-5-dUTP | Pyrene-8-dATP |
| Fluorescein Chlorotriazinyl-4-dUTP | Tetramethylrhodamine-6-dATP |
| Pyrene-8-dUTP | Texas Red-5-dATP |
| Diethylaminocoumarin-5-dUTP | DNA-N6-dATP |
| | Biotin-N6-dATP |

| dCTP Analogs | dGTP Analogs |
| --- | --- |
| Coumarin-5-dCTP | Coumarin-5-dGTP |
| Fluorescein-12-dCTP | Fluorescein-12-dGTP |
| Tetramethylrhodamine-6-dCTP | Tetramethylrhodamine-6-dGTP |
| Texas Red-5-dCTP | Texas Red-5-dGTP |
| LISSAMINE ™-rhodamine-5-dCTP | LISSAMINE ™-rhodamine-5-dGTP |
| Naphthofluorescein-5-dCTP | |
| Fluorescein Chlorotriazinyl-4-dCTP | |
| Pyrene-8-dCTP | Diethylaminocoumarin-5-dCTP |
| Fluorescein-N4-dCTP | |
| Biotin-N4-dCTP | |
| DNP-N4-dCTP | |

RIBONUCLEOTIDE ANALOGS

| CTP Analogs | UTP Analogs |
| --- | --- |
| Coumarin-5-CTP | Fluorescein-12-UTP |
| Fluorescein-12-CTP | Coumarin-5-UTP |
| Tetrainethylrhodainine-6-CTP | Tetramethylrhodamine-6-UTP |
| Texas Red-5-CTP | Texas Red-5-UTP |
| LISSAMINE ™-rhodamine-5-CTP | LISSAMINE ™-5-UTP |
| Naphthofluorescein-5-CTP | Naphthofluorescein-5-UTP |
| Fluorescein Chlorotriazinyl-4-CTP | Fluorescein Chlorotriazinyl-4-UTP |
| Pyrene-8-CTP | Pyrene-8-UTP |
| Fluorescein-N4-CTP | |
| Biotin-N4-CTP | |

| ATP Analogs | |
| --- | --- |
| Coumarin-5-ATP | |
| Fluorescein-12-ATP | |
| Tetramethylrhodamine-6-ATP | |
| Texas Red-5-ATP | |
| LISSAMINE ™-rhodamine-5-ATP | |
| Fluorescein-N6-ATP | |
| Biotin-N6-ATP | |
| DNP-N6-ATP | |

Additional non-conventional nucleotides useful according to the invention include, but are not limited to 7-deaza-dATP, 7-deaza-dGTP, 5'-methyl-2'-deoxycytidine-5'-triphosphate. Further non-conventional nucleotides or variations on those listed above are discussed by Wright & Brown, 1990, Pharmacol. Ther. 47: 447. It is specifically noted that ribonucleotides qualify as non-conventional nucleotides, since ribonucleotides are not generally incorporated by DNA polymerases. Modifications of Family B DNA polymerases that result in the ability, or enhanced ability, of the polymerase to incorporate labeled or unlabeled ribonucleotides are specifically contemplated herein.

E. Methods of Evaluating Mutants for Reduced Discrimination

Random or site-directed mutants generated as known in the art or as described herein and expressed in bacteria may be screened for reduced discrimination against non-conventional nucleotides by several different assays. In one method, Family B DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) *Gene* 97:119–123). For this approach, lambda phage clones are plated at a density of 10–20 plaques per square centimeter. Proteins present in the plaques are transferred to filters and moistened with polymerase screening buffer (50 mM Tris (pH 8.0), 7 mM $MgCl_2$, 3 mM β-ME). The filters are kept between layers of plastic wrap and glass while the host cell proteins are heat-inactivated by incubation at 65° C. for 30 minutes. The heat-treated filters are then transferred to fresh plastic wrap and approximately 35 μl of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 ug/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 1.29 μCi/ml α-$^{33}$P ddNTP or dideoxynucleotides (at a dNTP:dye-ddNTP ratio of 1:15). Initial screening was done in the presence of $MnCl_2$, but the preferred method was to screen in 1× Taq Polymerase buffer (1.5 mM $MgCl_2$) The filters are placed between plastic wrap and a glass plate and then incubated at 65° C. for one hour, and then at 70° C. for one hour and fifteen minutes. Filters are then washed three times in 2× SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measure of the activity of the polymerase with regard to that particular unconventional nucleotide or combination of unconventional nucleotides used in the assay. Unconventional nucleotides corresponding to all four conventional nucleotides may be included in the reactions, or, alternatively, only one unconventional nucleotide may be included to assess the effect of the mutation(s) on utilization of a given unconventional nucleotide. One approach is to use unconventional nucleotides corresponding to all four nucleotides in a first screen to identify clones that incorporate more than a reference wild-type clone, and then to monitor the incorporation of individual unconventional nucleotides in a subsequent screen. In the preferred screening mode, only the dideoxynucleotides and dideoxynucleotide analogs of ddATP, ddCTP, and ddTTP would be used since ddGTP is not discriminated against by some DNA polymerases and increases the background signal of any screen In order to screen for clones with enhanced ability to incorporate dideoxynucleotides, clones identified in first screens utilizing only dideoxynucleotides may then be characterized by their sensitivity to low levels of each of the four dideoxynucleotides in a DNA polymerase nucleotide incorporation assay employing all four dNTPs, a ;H-TTP tracer, and a low level of each ddNTP. Since incorporation of dideoxynucleotides stops DNA chain elongation, superior ability to incorporate dideoxynucleotides diminishes the incorporation of tritium labeled deoxynucleotides relative to wild-type DNA polymerase. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

In order to measure incorporation of individual ddNTPs, cocktails are prepared which consist of varying concentrations of the ddNTP of interest, and a total of 200 μM of each nucleotide triphosphate. For example, the incorporation of ddATP by wild type JDF-3 polymerase may be measured at 0, 40, 80, 120 and 160 μM ddATP. In these reactions, dATP concentrations would be adjusted to 200, 160, 120, 80, and 40 μM, respectively, so that the total amount of adenine nucleotide triphosphate is 200 μM. In comparison, mutants may be assayed using ddATP concentrations of 0, 5, 10, and 20 μm ddATP, and adjusted dATP concentrations of 200, 195, 190, and 180 μM, respectively (dATP+ddATP=200 μM). Additional cocktails are prepared to similarly measure ddCTP, ddGTP, and ddTTP incorporation.

Incorporation of nucleotides under the concentration parameters described above may be measured in extension reactions by adding, for example, 1 μl of appropriately diluted bacterial extract (i.e., heat-treated and clarified extract of bacterial cells(see Example 1, part M) expressing a cloned polymerase or mutated cloned polymerase) to 10 ul of each nucleotide cocktail, followed by incubation at 72° C. for 30 minutes. Extension reactions are quenched on ice, and then 5 μl aliquots are spotted immediately onto DE81 ion-exchange filters (2.3 cm; Whatman #3658323). Unincorporated label is removed by 6 washes with 2× SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms" (wash filters as above).

Cpms bound is proportional to the amount of polymerase activity present per volume of bacterial extract. The volume of bacterial extract (generally about 0.25–1 μl) which brings about incorporation of approximately 10,000 cpms is determined for use in subsequent nucleotide analog incorporation testing.

Genes for mutant DNA polymerases generated by random mutagenesis may be sequenced to identify the sites and number of mutations. For those mutants comprising more than one mutation, the effect of a given mutation may be evaluated by introduction of the identified mutation to the exo⁻ progenitor gene by site-directed mutagenesis in isolation from the other mutations borne by the particular mutant. Screening assays of the single mutant thus produced will then allow the determination of the effect of that mutation alone.

F. Expression of Mutated Family B DNA Polymerase According to the Invention

Methods known in the art may be applied to express and isolate the mutated forms of Family B DNA polymerase according to the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter (see Gardner & Jack, 1999, supra).

Appropriate host strains of bacteria may be selected from those available in the art by one of skill in the art. As a non-limiting example, *E coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, PCR Meth. & App. 2: 275) is well suited for the isolation of thermostable DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure thermostable DNA polymerase. Further, as detailed in Example 1, part N, below, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

G. Preparation of *Thermococcus* species JDF-3 Thermostable DNA Polymerase With Reduced Discrimination To prepare thermostable Family B polymerases which exhibit reduced discrimination for dideoxynucleotide triphosphates (ddNTPs), the DNA sequence encoding a 3' to 5' exonuclease- deficient (D141A) Family B polymerase from the hyperthermophilic archaeon *Thermococcus* species JDF-3 was subjected to random mutagenesis using "error-prone PCR" as described herein, and cloned into the bacteriophage lambda Zap®II. The polymerase from JDF-3 was chosen due to superior processivity, polymerization rate and ddNTP incorporation relative to the Family B DNA polymerase from *Pyrococcus furiosus* (Pfu) (see Table IV, below). The library of mutants was plated on *E. coli* hosts and the proteins present in the lytic plaques were transferred to a solid support that was then immersed in a buffer containing DNA template and all four α-$^{33}$P labeled dideoxynucleotides. Mutants that incorporated the labeled dideoxynucleotide produced signals that corresponded to their ability to incorporate the α-$^{33}$P ddNTPs. Isolated clones were then characterized by their sensitivity to low levels of each of the four dideoxynucleotides in a DNA polymerase nucleotide incorporation assay employing all four dNTPs and a ;H-TTP tracer. Since incorporation of dideoxynucleotides stops DNA chain elongation, superior ability to incorporate dideoxynucleotides diminishes the incorporation of tritium labeled deoxynucleotides. The unmutated progenitor DNA polymerase rarely incorporates dideoxynucleotides and is only 50% inhibited at high ddNTP levels (100–160 micromolar each ddNTP). The mutant enzymes show 50% inhibition at 5 to 40 micromolar concentrations of ddNTP and improved incorporation was observed for all four ddNTPs (ddATP, ddCTP, ddTTP and ddGTP; see Tables V and VI in Example 1, below).

The incorporation of non-conventional nucleotides was also evaluated through use of purified mutant polymerases in cycle sequencing, with α-$^{33}$P labeled ddNTPs present at 0.021 μM and dNTPs present at 2.1 μM each. The mutants readily utilized all four dideoxynucleotides and produced sequencing ladders that compared favorably to Thermo Sequenase®, which uses an F667Y Taq DNA polymerase mutant (VanderHorn et al., 1997, BioTechniques 22: 758).

The domains of relevance in 17 of the 40 purified mutants were sequenced. Most randomly mutated clones contained more than one mutation in the regions sequenced but all mutants contained mutations at one of three sites. Mutations predicted to confer an enhanced ddNTP uptake phenotype were introduced into the progenitor exonuclease deficient DNA polymerase sequence by site-directed mutagenesis to eliminate ancillary mutations which were not expected to contribute to the improved dideoxynucleotide uptake phenotype.

Sixteen of the seventeen JDF-3 DNA polymerase mutations were found in region II (motif A) on either side of the tyrosine in the consensus sequence 404 DxxSLYPSII 413 (SEQ ID NO: 7). These mutations consisted of DFRSLYL-SII (P410L) (SEQ ID NO: 8), DFRSHYPSII (L408H) (SEQ ID NO: 9) and DFRSFYPSII (L408F) (SEQ ID NO: 10). Therefore, the LYP motif of region II appears to be important in ddNTP discrimination in the JDF-3 Family B polymerase.

The prior art modification of the tyrosine corresponding to Y409 in JDF3 Family B DNA polymerase is recognized for its positioning in the nucleotide binding pocket. As shown herein, however, modification of the residues neighboring Y409 (L408H or L408F or P410L) had the unexpected effect of profoundly altering nucleotide binding, particularly with respect to ddNTP incorporation.

The only JDF-3 DNA polymerase mutation leading to enhanced incorporation of non-conventional nucleotides occurring outside of region II is an alanine (ala or A) to threonine (thr or T) conversion at position 485 in region III (A485T). This site is two residues upstream of KX$_3$NSXYG (SEQ ID NO: 5) (Jung et al., 1990, Supra; Blasco et al., 1992, supra; Dong et al., 1993, J. Biol. Chem. 268:21163; Zhu et al., 1994, Biochem. Biophys. Acta 1219:260; Dong and Wang, 1995, J. Biol. Chem. 270:21563) (referred to as region III or motif B) which is functionally, but not structurally (Wang et al., 1997, supra), analogous to KX$_3$(F/Y) GX$_2$YG (SEQ ID NO: 6) in helix O of the Family A DNA polymerases. In Family A DNA polymerases, such as the Klenow fragment and Taq DNA polymerases, the O helix contains amino acids that play a major role in dNTP binding (Astatke et al., 1998, J. Mol. Biol. 278:147; Astatke et al., 1995, J. Biol. Chem. 270:1945; Polesky et al., 1992, J. Biol. Chem 267:8417; Polesky et al., 1990, J. Biol. Chem. 265:14579; Pandey et al., 1994, J. Biol. Chem. 269:13259; Kaushik et al., 1996, Biochem. 35:7256). Specifically, helix O contains the F (F762 in the Klenow fragment; F667 in Taq) which confers ddNTP discrimination in Family A DNA polymerases (KX$_3$(K/Y)GX$_2$YG SEQ ID NO: 6) (Tabor and Richardson, 1995, supra).

The effect of the A485T mutation on ddNTP incorporation in the JDF-3 DNA polymerase is surprising since the RB69 and *Thermococcus gorgonarius* crystal structures (Hopfner et al., 1999, supra) show it facing away from the proposed active site of the nucleotide binding surface. Moreover, the type of side chain conferring ribose selectivity in archaeal Family B DNA polymerases (A: small, non-polar) is different from that of the bulky, aromatic Y and F residues that dictate ddNTP discrimination in Family A DNA polymerases (Tabor and Richardson, 1995, supra). Additionally, this position (A485) is not well conserved among either DNA polymerase family and is not included in the consensus sequence for this domain (Braithwaite and Ito, 1993, supra), implying a lack of critical importance in dNTP recognition.

A JDF-3 double mutant was constructed that contains mutations P410L and A485T. In dideoxynucleotide cycle sequencing, the banding pattern intensity demonstrated by the double mutant was extremely uniform, suggesting little if any preference for any dNTP over its corresponding ddNTP (See FIG. 8 and Example 1Q). This polymerase characteristic improves the accuracy of base calling in automated sequencing. We presume that combinations of P410L and A485 mutations, L408H and A485 mutations, and L408F and A485 mutations would result in enzymes that exhibit improved ddNTP incorporation. The efficiency of dideoxynucleotide incorporation by such double mutant enzymes may also be characterized or quantitated by measurement of the $I_{50\%}$ as described herein to determine the relative degree of improvement in incorporation.

EXAMPLES

The following examples are offered by way of illustration only and are by no means intended to limit the scope of the claimed invention.

Example 1

A. Cloning a DNA Polymerase Gene from *Thermococcus* species JDF-3 DNA Polymerase A *Thermococcus* species was cultured from submarine samples taken from the Juan de Fuca ridge. Genomic DNA was isolated and used to prepare a genomic DNA library in ZAP II (Stratagene) using standard procedures. The lambda library was plated on XL1-Blue MRF' *E. coli* and screened for clones with DNA polymerase activity using a variation of the method described by Sagner et al. (Sagner, G., Ruger, R., and Kessler, C. (1991) *Gene* 97:119–123). Plaques containing active polymerase were cored and stored in SM buffer. Positive primary plaques were re-plated and re-assayed to allow purification of isolated clones. Secondary clones were excised according to the instructions provided with the ZAP II system (Stratagene), and the DNA sequence of the insert determined (FIG. 1).

The translated amino acid sequence of the JDF-3 DNA polymerase is shown in FIG. 2. Amino acid sequence alignments show that JDF-3 DNA polymerase exhibits homology to the class of DNA polymerases referred to as Family B.

Recombinant JDF-3 DNA polymerase was purified as described below (see "Purification of JDF-3" (method 1)). The biochemical properties of JDF-3 DNA polymerase have been compared to those of other commercially available archaeal DNA polymerases. The results shown in Table IV and V indicated that, compared to other enzymes, JDF-3 exhibits higher processivity, a faster polymerization rate ($K_{cat}$), and a greater tendency to utilize ddNTPs. JDF-3 DNA polymerase was therefore chosen for development of a DNA sequencing enzyme.

TABLE IV

Polymerase Activities of Archaeal Family B DNA Polymerases

| Polymerase | Specific Activity (U/mg) × $10^4$ Activated DNA | Primed M13 | DNA (nM) | dNTP ($\mu$M each) |
|---|---|---|---|---|
| Pfu | 2.6 ± .07  4.1 ± .07 | 2.0 ± .02 | 0.7 | 16 ± 2 |
| exo⁻ Pfu |  | 2.3 | 0.5 | 12 |
| JDF-3 | 1.2 ± .07 | 5.2 | 2.0 | 16 ± 2 |
| Vent | 1.8[a] | 0.7[a] | 0.1[a] | 57[a] |

[a]H. Kong, R. B. Kucera, and W. E Jack, J. Biol. Chem. 268, 1965 (1993).

B. Intein Removal From the Gene Encoding JDF-3 DNA Polymerase

By alignment to Family B DNA polymerase sequences, the JDF-3 DNA polymerase clone was found to contain an intein sequence (FIGS. 3 and 4). To improve expression of recombinant JDF-3 polymerase, the intein was removed by inverse PCR. PCR primers were designed to prime immediately upstream and downstream to the sequence coding for the intein termini, and were oriented such that the 3' ends of the primers were pointed away from the intein. The primers were also modified with 5'-phosphate groups to facilitate ligation. The plasmid/insert sequence was PCR amplified and circularized by standard methods.

C. Construction of a JDF-3 DNA Polymerase Mutant with Diminished 3'-5' Exonuclease Activity DNA polymerases lacking 3'–5' exonuclease (proofreading) activity are preferred for applications requiring nucleotide analog incorporation (e.g., DNA sequencing) to prevent removal of nucleotide analogs after incorporation. The 3'–5' exonuclease activity associated with proofreading DNA polymerases can be reduced or abolished by mutagenesis. Sequence comparisons have identified three conserved motifs (exo I (DXE), II ($NX_{2-3}$(F/Y)D), III ($YX_3D$)) in the 3'–5' exonuclease domain of DNA polymerases (reviewed V. Derbyshire, J. K. Pinsonneault, and C. M. Joyce, *Methods Enzymol.* 262, 363 (1995)). Replacement of any of the conserved aspartic or glutamic acid residues with alanine has been shown to abolish the exonuclease activity of numerous DNA polymerases, including archaeal DNA polymerases such as Vent (H. Kong, R. B. Kucera, and W. E. Jack, *J. Biol. Chem.* 268, 1965 (1993)) and Pfu (Stratagene, unpublished). Conservative substitutions lead to reduced exonuclease activity, as shown for mutants of the archaeal 9° N-7 DNA polymerase (M. W. Southworth, H. Kong, R. B. Kucera, J. Ware, H. Jannasch, and F. B. Perler, *Proc. Natl. Acad. Sci.* 93, 5281 (1996)).

JDF-3 DNA polymerase mutants exhibiting substantially reduced 3'–5' exonuclease activity were prepared by introducing amino acid substitutions at the conserved 141D or 143E residues in the exo I domain. Using the CHAMELEON® Double-Stranded, Site-Directed Mutagenesis Kit (Stratagene), the following JDF-3 mutants were constructed: D141A, D141N, D141S, D141T, D141E and E143A.

To analyze JDF-3 mutant proteins, the DNA sequence encoding JDF-3 DNA polymerase was PCR amplified using primers GGG AAA CAT <u>ATG</u> ATC CTT GAC GTT GAT TAC (SEQ ID NO: 11) (where NdeI site in bold and start codon underlined) and GGG AAA GGA TCC TCA CTT CTT CTT CCC CTT C (SEQ ID NO: 12) (where BamHI site shown in bold type). The PCR products were digested, purified, and ligated into a high expression level vector using standard methods. Plasmid clones were transformed into BL21 (DE3). Recombinant bacterial clones were grown using standard procedures and JDF-3 polymerase mutants were expressed in the absence of induction. The exonuclease and polymerase activities of recombinant clones were assayed using bacterial lysates. Typically, crude extracts were heated at 70° C. for 15–30 minutes and then centrifuged to obtain a cleared lysate.

There are several methods of measuring 3' to 5' exonuclease activity known in the art, including that of Kong et al. (Kong et al., 1993, J. Biol. Chem. 268: 1965) and that of Southworth et al. (Southworth et al., 1996, Proc. Natl. Acad. Sci. U.S.A. 93: 5281), the full contents of both of which are hereby incorporated by reference. The exonuclease activity of wild type and active mutant polymerases as measured by the Kong et al. method were as follows:

Exo activity (U/mg):
Wt 915
D141A7
D141N953
D141S954
D141T0.5
D141E940
E143A0.3

The combination exonuclease mutant D141A+E143A was made as described in section L.

The E143A JDF-3 mutant (clone #550) exhibited significantly reduced 3'-5' exo activity and was chosen for further mutagenesis to improve incorporation of ddNTP and other nucleotide analogs. Other JDF-3 mutants with substantially reduced exonuclease activity could have been used for this purpose, such as the JDF-3 D141T mutant for experiment or applications requiring the absolute elimination of 3' to 5' exonuclease activity, the double mutant D141A+E143A was preferred.

D. Error-prone PCR Amplification of the JDF-3 DNA Polymerase Gene

Random mutations were introduced into exo⁻ JDF-3 by amplifying the entire gene (clone #550) under conditions which did not support high fidelity replication. To broaden the spectrum of potential mutations, three different PCR enzymes were used under error-prone conditions.

In the preferred mode, ten reactions of 100 µl each were amplified with each PCR enzyme.

i. Amplification with Taq DNA polymerase:

| Reaction Mixture | |
|---|---|
| 1x | magnesium free Taq Buffer (Stratagene catalog #200530) |
| 1 mM | each TTP and dCTP |
| 0.2 mM | each dGTP and dATP |
| 2 ng/µl | Primer 923 (also called 490) |
| 2 ng/µl | Primer 721 |
| 0.05 u/µl | Taq2000 (Stratagene catalog #600195) |
| 1.5 mM | MgCl$_2$ |
| 0.5 mM | MnCl$_2$ |
| 0.1 pM | plasmid DNA (clone #550) |

Cycling Parameters

PCRs were carried out using Stratagene's ROBOCYCLER™40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
e) Repeat steps 2 to 4 thirty times.

ii. Amplification with exo⁻ JDF-3 DNA polymerase
Reaction Mixture 1x magnesium free Taq Buffer (Stratagene catalog #200530)
450 µM each deoxynucleotide (dGTP, dATP, TTP and dCTP)
2 ng/µl Primer 923 (also called 490)
2 ng/µl Primer 721
0.1 u/µl exo⁻ JDF-3 DNA polymerase
0.5 mM MnCl$_2$
0.1 pM plasmid DNA (clone #550)

Cycling Parameters

PCRs were carried out using Stratagene's ROBOCYCLER™40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
5) Repeat steps 2 through 4 thirty times.

iii. Amplification with exo⁻ Pfu DNA polymerase
Reaction Mixture

1x TAQPLUS® Precision Buffer (Stratagene catalog #600210)
200 µM each deoxynucleotide (dGTP, dATP, TTP, dCTP)
2 ng/µl Primer 923 (also called 490)
2 ng/µl Primer 721
0.05 u/µl exo⁻ Pfu DNA polymerase (Stratagene catalog number 600163)
0.1 pM plasmid DNA (clone #550)

Cycling Parameters

PCRs were carried out using Perkin-Elmer's 9600 Temperature Cycler. The following cycling conditions were used:

1) 95° C. for 1 minute
2) 95° C. for 1 minute
3) 53° C. for 1 minute
4) 72° C. for 5 minutes
5) Repeat steps 2 through 4 thirty times.

Forward Primers

Earlier versions of the mutant libraries were made with the forward primer 461, which contains an EcoR I site. When products amplified with primers 461 and 923 were restriction digested and cloned into the lambda vector as described in the following section, JDF-3 DNA polymerase was synthesized as a fusion protein with the first 39 amino acids of the vector-encoded β-galactosidase (lacZ) protein.

Primer 461 5'TCAGATGAATTCGATGATCCTTGACGTTGATTAC3' (SEQ ID NO: 13)

EcoR I JDF-3 specific sequence

The clones isolated using primer 461 were designed as p#.

The preferred mode of amplification and cloning utilizes the forward primer 721, which also contains an EcoR I site followed by three consecutive in-frame stop codons and a ribosome binding site. This arrangement allows the JDF-3 DNA polymerase to be translated without any vector-derived residues at the amino terminus. The clones isolated from libraries constructed with the forward primer 721 were designated as 1-# to differentiate them from the p# series of clones.

Primer 721 5'GAGAGAATTCATAATGATAAGGAGGAAAAAATTATGATCCTTGACGTTGATTAC3' (SEQ ID NO: 14)

EcoR I 3× STOP JDF-3 specific sequence
Reverse Primers
Primer 923(490) 5'TCAGATCTCGAG
TCACTTCTTCTTCCCCTTC3' (SEQ ID NO: 15)
Xho I JDF-3 specific sequence E. Preparing PCR Products for Cloning PCR products were purified and concentrated with the STRATAPREP™ PCR Purification kit (Stratagene catalog number 400771). The PCR products were then digested with 50 units of Xho I and 50 units of EcoR I in 1.5× Universal buffer (10× Universal Buffer: 1M KOAc, 250 mM Tris-Acetate (pH 7.6), 100 mM MgOAc, 5 mM β-mercaptoethanol and 100 µg/ml BSA) for one hour at 37° C. The digested samples were run on a 1% agarose, 1× TBE gel and visualized with ethidium bromide staining. The 2.3 kb amplification product was gel isolated and purified with the STRATAPREP™ DNA Gel Extraction Kit (Stratagene catalog number 400766).

F. Cloning PCR Inserts into the Uni-Zap®XR Lambda Vector 200 ng of purified amplification product was ligated with 1 µg of UNI-ZAP®XR Lambda Vector (Stratagene catalog #239213), which had been predigested with EcoR I and Xho I and then dephosphorylated with alkaline phosphatase (Stratagene catalog number 237211). The DNAs were ligated using 2 units of T4 DNA ligase (Stratagene catalog number 600011) and 0.5 mM ATP in 1× ligase buffer (50 mM Tris-HCL (pH 7.5), 7 mM $MgCl_2$, 1 mM DTT) in reaction volumes of 10 to 15 µl. Ligations were carried out at 16° C. for a minimum of 16 hours.

G. Lambda Packaging and Bacterial Infection

Two microliters of each ligation reaction were packaged with GIGAPACK® III Gold Packaging extract (Stratagene catalog #200201) for 90 minutes at room temperature before being stopped with 500 µl SM buffer (50 mM Tris pH 7.5, 100 mM NaCl, 8 mM $MgSO_4$ and 0.01% gelatin) and 20 µl of chloroform. The packaged lambda vectors were plated on E. coli XL1-Blue MRF' host cells.

H. Dideoxynucleotide Screening

Mutant polymerase libraries were screened using a variation of the technique used by Sagner et al (Sagner, G., Ruger, R., and Kessler, C. (1991) Gene 97:119–123). Lambda phage clones were plated at a density of 10–20 plaques per square centimeter. Proteins present in the plaques were transferred to filters and moistened with polymerase screening buffer (50 mM Tris (pH 8.0), 7 mM $MgCl_2$, 3 mM β-ME). The filters were kept between layers of plastic wrap and glass while the host cell proteins were heat-inactivated by incubation at 65° C. for 30 minutes. The heat-treated filters were transferred to fresh plastic wrap and approximately 35 µl of the polymerase assay cocktail was added for every square centimeter of filter. Polymerase assay cocktail consisted of 1× cloned Pfu magnesium-free buffer (Stratagene catalog #200534), 125 ng/ml activated calf thymus or salmon sperm DNA, 1.29 µCi/ml α-$^{33}$P ddNTP (Amersham), and 0.5 mM $MnCl_2$. Initial screening was done in the presence of $MnCl_2$, but the preferred method was to screen in 1× Taq Polymerase buffer (1.5 mM $MgCl_2$). The filters were sandwiched between plastic wrap and glass again and incubated at 65° C. for one hour, and then at 70° C. for one hour and 15 minutes. The filters were washed three times in 2× SSC for five minutes each time before being rinsed twice in 100% ethanol and dried on a vacuum dryer. The filters were exposed to X-ray film for approximately 16 hours. Plaques corresponding to strong signals were cored and placed in SM buffer. The positive primary plaques were replated at more dilute concentrations and assayed under essentially similar conditions to allow the purification of isolated plaques.

Dye-dideoxynucleotide Screening

To detect mutant polymerases with improved capacity for dye-deoxynucleotide and dye-dideoxynucleotide utilization, the JDF-3 mutant DNA polymerase library was screened as described previously with the following exceptions:

Polymerase assay cocktail for Flu-12-dUTP screening:
0.9× Taq Buffer (Stratagene Catalog #200435), 65 µM dATP, 65 µM dCTP, 65 µM dGTP, 65 µMdTTP, 0.3 µM Fluoresceince-12-dUTP (Stratagene in-house production), 0.75 µg/µl activated calf thymus DNA.

Polymerase assay cocktail for ROX ddNTP
1× Taq Buffer, 0.9 µM dATP, 0.9 µM dCTP, 0.9 µM dGTP, 0.9 µl TTP, 0.6 µM ROX ddATP (New England Nuclear (NEN) NEN478), 0.06 µM ROX ddGTP (NEN NEL479), 0.06 µM ROX ddCTP (NEN NEL477), 0.06 µM ROX ddUTP (NEN NEL476), 0.84 µg/µl activated calf thymus DNA. (Note: A screening system without ROX ddGTP is the preferred method since DNA polymerases do not discriminate against ddGTP).

Polymerase assay cocktail for Fluroesceine ddUTP
1× Taq Buffer, 70 µM dATP, 70 µM dTTP, 70 µM dCTP, 15 µM dTTP, 1 µM Fluroesceine-12-ddUTP (NEN NEL401), 0.84 µg/µl activated calf thymus DNA.

Antibody binding to fluroesceine

The filters were blocked overnight with 1% non-fat dry milk dissolved in TBST (50 mM Tris pH 8.0, 150 mM NaCl, 0.05% Tween-20) at 4° C. The filters were washed briefly in TBST before alkaline phosphatase conjugated anti-fluoresceine antibody from the Illuminator kit (Stratagene catalog #300360) was added at a 1/10,000 dilution in 50 ml TBST. The antibody was detected with NBT/BCIP at concentrations of 0.3 mg/ml and 0.15 mg/ml respectively in a buffer composed of 100 mM Tris pH 9.5, 100 mM NaCl, and 5 mM $MgCl_2$.

Antibody binding to Rhodamine

Anti-ROX antibody (Zymed cat. no. 71-3600 rabbit Rhodamine (5-ROX polyclonal, 1 mg/ml)) was diluted to 1:1000 in TBST. The blocked filters were blotted briefly to remove excess moisture then laid on plastic wrap and covered with 2.5 ml of the diluted antibody solution. An additional sheet of plastic wrap was laid over the filters before incubation at room temperature for 1 hour. The filters were washed briefly three times with TBST, then washed three times with gentle agitation for 15 minutes each time. The washed filters were incubated with alkaline phosphatase conjugated goat anti-rabbit antibodies diluted 1:5000 in TBST. The filters were incubated with the antibody for one hour then detected with NBT/BCIP as described previously.

I. Dideoxynucleotide Qualification

Lambda phage clones which incorporated $^{33}$P-labeled ddNTPs in the primary library screen were re-screened to verify polymerase activity and to assess the contribution of the divalent metal ion to $^{33}$P-ddNTP incorporation. The clones selected during this round of screening were designated as p#. These clones all contained an amino-terminal tag, as discussed in the section entitled "Forward Primers". FIG. 5 shows that clones p1, p2, p3, p6, p7, p8, p9, p10, p11, p12, p14, p15, and p16 exhibited wild type levels of DNA polymerase activity, based upon similarity in signal strength to the parental #550 clone (FIG. 5, panel 3). Although initial screening was carried out in the presence of 0.5 mM $MnCl_2$, all of the clones except p9 and p10 were able to incorporate $^{33}$P-labeled ddNTPs to at least some extent in the presence of 1.5 mM $MgCl_2$ (panel 2), with clones p2, p4, p8, p11, p12, p13, p14, p15, p17, and p18 producing the highest signals.

Eighteen mutants were chosen for evaluation. One microliter of phage isolated from each purified plaque was placed on each of three E. coli XL1-Blue MRF' lawns. Phage containing a parental copy of exo⁻ JDF3 DNA (#550 clone) were also spotted on the grid. The plaques formed by the phage were transferred to filters and treated as described in the preceding screening section with the exception of the final buffer composition. The buffers used for each filter (filters 1–3) are as follows:

| Filter 1: Dideoxynucleotide screen with manganese chloride | |
|---|---|
| 1x | Taq DNA polymerase magnesium-free buffer |
| 1.28 µCi/ml | $^{33}$P ddNTPs |
| 0.5 µg/µl | Activated Calf Thymus DNA (Sigma) |
| 0.5 mM | MnCl$_2$ |

| Filter 2: Dideoxynucleotide screen with magnesium chloride | |
|---|---|
| 1x | Taq DNA polymerase buffer (containing 1.5 mM MgCl$_2$, catalog #200435) |
| 1.28 µCi/ml | $^{33}$P ddNTP |
| 0.5 µg/µl | Activated Calf Thymus DNA (Sigma) |

| Filter 3: Deoxynucleotide screen with magnesium chloride | |
|---|---|
| 1x | Taq DNA polymerase buffer |
| 0.072 mM | dGTP, dCTP and TTP |
| 40 µM | dATP |
| 0.5 µg/ml | Activated Calf Thymus DNA (Sigma) |
| 0.01 µCi | α-$^{33}$P dATP. |

Results are shown in FIG. 5.

Dye-dideoxynucleotide Qualification

As described in the previous segments, primary lambda clones were spotted on an E. coli lawn and re-screened with the appropriate antibody or antibodies.

J. Excision of Lambda Clones

When incubated with helper phage under suitable conditions, Lambda Zap™ vectors are designed to produce phagemid copies of the part of the vector containing pBluescript (SK-) and the insert. This process yields a plasmid (pBluescript SK-) vector carrying the same insert that was contained in the lambda clone. Excision of clones with the desired phenotype was carried out according to the instructions in the EXASSIST™ system (Stratagene catalog #200253).

K. Sequence Analysis of Mutants

The mutants were sequenced by Sequetech Corporation (Mountain View, Calif.) using the following primers:

Primer 3 (or primer G) 5' CCAGCTTTCCAGAC-TAGTCGGCCAAGGCC 3' (SEQ ID NO: 16)

Primer 5 (or JDF3-1128) 5'AACTCTCGACCCGCTG 3' (SEQ ID NO: 17)

L. Dideoxynucleotide Mutagenesis

To conclusively identify the amino acids contributing to reduced ddNTP discrimination, individual point mutations were introduced into the exo⁻ JDF-3 #550 clone using the QUIKCHANGE™ Site-Directed Mutagenesis Kit (Stratagene catalog #200518). The following mutants were prepared: L408H, L408F, P410L, A485T, S345P, D373Y, A619V, and L631V. In addition, a double mutant (P410L/A485T) was constructed by introducing the A485T mutation into the exo⁻ JDF-3 P410L mutant clone. To completely eliminate all 3' to 5' exonuclease activity, the mutation D141A was added to all clones. A pre-existing 5' to 3' exonuclease mutation (E143A) was present in the parental template JDF-3 550.

Dye-dideoxynucleotide mutagenesis

To conclusively identify amino acids responsible for contributing to reduced discrimination of dye nucleotides, the mutation S345P was generated alone and in combination with the P410L and P410L+A485T.

M. Preparation of Heat-treated Bacterial Extracts

E. coli SOLR cells containing the excised plasmid were grown overnight at 37° C. The cells contained in 500 µl of culture were collected by microcentrifugation. The cell pellets were resuspended in 50 µl of 50 mM Tris (pH 8.0). Lysozyme was added to a final concentration of 1 µg/µl, and the cells were lysed during a 10 minute incubation at 37° C., followed by 10 minutes at 65° C. The heat-inactivated cell material was collected by microcentrifugation and the supernatants were assayed for dNTP and ddNTP incorporation as described below.

N. Purification of JDF-3 and JDF-3 Polymerase Mutants

One method for purifying exo⁻ JDF-3 DNA polymerase involves ammonium sulfate fractionation, followed by Q Sepharose and DNA cellulose columns. A second method has been developed to allow rapid purification of JDF-3 polymerase mutants, and entails adsorption of contaminants on a HiTrap Q column, followed by gradient elution from a HiTrap heparin column (section iii).

i. Preparation of bacterial lysate.

Frozen cell paste (3–14 grams) was resuspended with 3x volume of lysis buffer, consisting of 50 mM Tris-HCl (pH 8.0), 1 mM EDTA, and 10 mM β-mercaptoethanol. Lysozyme was added to 0.2 mg/ml and PMSF was added to 1 mM final concentration. The cells were lysed on ice over a period of 1 hour. The lysate was then sonicated for 2 minutes (90% duty, level of 2×2.5, 1×3.0). Following sonication, the lysate was heated at 65° C. for 15 minutes to denature bacterial proteins. The heated lysate was then centrifuged for 30 minutes at 14.5K rpm in a Sorvall RC-2B centrifuge using a Sorvall SS-34 rotor, and the supernatant was recovered.

ii. Ammonium sulfate fractionation and Q Sepharose/DNA cellulose chromatography (method 1)

Ammonium sulfate was added to the bacterial lysate to a final concentration of 45%. The ammonium sulfate was added over a period of 15 minutes, and the mixture was stirred for an additional 30 minutes. The mixture was centrifuged as described above, and the supernatant was recovered. Additional ammonium sulfate was then added to bring the final concentration to 65%. The mixture was centrifuged as described above, and the supernatant removed. The pellet was resuspended in 10 ml of buffer A consisting of 50 mM Tris-HCl (pH 7.5), 1 mM EDTA, 10 mM β-mercaptoethanol, 0.1% (v/v) Tween 20, and 10% (v/v) glycerol. The supernatant was dialyzed overnight against 2 changes of buffer A (3 liters each).

The dialysate was loaded onto a 2.6×9.4 cm Q-Sepharose Fast Flow column (50 mls), pre-equilibrated in buffer A. The column was washed with buffer A until the absorbence ($OD_{280}$) approached baseline. The column was then eluted with a gradient from 0 to 1M NaCl/buffer A. Fractions were collected, and analyzed by SDS-PAGE and DNA polymerase activity assays (see below). Active protein typically eluted between 130 and 240 mM NaCl. Active fractions were pooled and dialyzed overnight against 2 changes of buffer B (3 liters each), consisting of 50 mM Tris-HCl (pH 7.5), 1 mM EDTA, 10 mM β-mercaptoethanol, 0.1% (v/v) Tween 20, 10%(v/v)glycerol, and 50 mM NaCl.

The Q-Sepharose eluate was then loaded onto a 1.6×4.9 cm (10 mls) DNA cellulose column, equilibrated in buffer B. The column was washed with buffer B until the absorbence ($OD_{280}$) approached baseline. The column was then eluted with a gradient from 50 to 1000 mM NaCl/buffer A. Fractions were collected, and analyzed by SDS-PAGE and DNA polymerase activity assays. Active protein typically eluted between 280 and 360 mM NaCl. Active fractions were pooled and dialyzed overnight against JDF-3 final dialysis buffer, consisting of 25 mM Tris-HCl (pH 7.5), 100 mM KCl, 0.1 mM EDTA, 1 mM DTT, 0.1% (v/v) Tween 20, 0.1% (v/v) Igepal 630, 10 μg/ml BSA, and 50% (v/v) glycerol.

iii. HiTrap Q/HiTrap heparin chromatography (method 2)

The preferable method for rapid purification of multiple mutants is as follows. Bacterial cell lysates were prepared as described for method 1, except that Tween 20 and Igepal CA 630 were added to a final concentration of 0.01% (v/v) just prior to the heat denaturation step, and a heat denaturation temperature of 72° C. was used.

The lysate was loaded onto a 1.6×2.5 cm (5 mls) HiTrap Q column (pre-packed column from Pharmacia), pre-equilibrated in buffer C consisting of 50 mM Tris-HCl (pH 8.2), 1 mM EDTA, 10 mM β-mercaptoethanol, 0.1% (v/v) Tween 20, and 0.1% (v/v) Igepal CA 630. The column was washed with buffer C until the absorbence ($OD_{280}$) approached baseline. The flow through fractions ($OD_{280}$ absorbence above background) were collected and then loaded onto a 1.6×2.5 cm (5 mls) HiTrap heparin column (pre-packed column from Pharmacia), pre-equilibrated in buffer D consisting of 50 mM Tris-HCl (pH 8.2), 1 mM EDTA, 1 mM DTT, 0.1% (v/v) Tween 20, 0.1% (v/v) Igepal CA 630, and 10% glycerol (v/v). The column was washed with buffer D until the absorbence ($OD_{280}$) approached baseline. The column was then eluted with a gradient from 0 to 1M KCl/buffer D. Fractions were collected, and analyzed by SDS-PAGE and DNA polymerase activity assays. Active protein typically eluted between 390 and 560 mM NaCl. Active fractions were pooled and dialyzed overnight against JDF-3 final dialysis buffer (see above). Purified polymerases were stored at −20 C.

iv. Analysis of Purified Proteins

The concentrations of JDF-3 and mutant DNA polymerases were determined relative to a BSA standard (Pierce), using Pierce's Coumassie Blue Protein assay reagent. In addition, the purity and relative protein concentrations of different polymerase preparations were verified by SDS-PAGE. Polymerase samples were electrophoresed on 4–20% Tris-glycine gels (Novex), and the gels were silver-stained using standard procedures.

O. Nucleotide Incorporation Assay

DNA polymerase activity was measured using purified JDF-3 polymerase mutants or heat-treated bacterial extracts prepared from various mutant clones. DNA polymerase activity was measured by monitoring the incorporation of $^3$H-TTP into activated calf thymus DNA. A typical DNA polymerase reaction cocktail contained:

10 mM Tris-HCl, pH 8.8

1.5 mM $MgCl_2$ 50 mM KCl 0.001% gelatin

200 μM each dATP, dCTP, dGTP

195 μM TTP

5 μM [$^3$H]TTP (NEN #NET-221H, 20.5 Ci/mmole; partially evaporated to remove EtOH)

250 μg/ml of activated calf thymus DNA (e.g., Pharmacia #27-4575-01)

Incorporation was measured by adding 1 μl of polymerase samples to 10 μl aliquots of polymerase cocktail. DNA polymerase samples were diluted in a suitable storage buffer (e.g., 25 mM Tris-HCl (pH 7.5), 100 mM KCl, 0.1 mM EDTA, 1 mM DTT, 0.1% (v/v) Tween 20, 0.1% (v/v) Igepal 630, 10 μg/ml BSA, and 50% (v/v) glycerol). Polymerization reactions were conducted for 30 minutes at 72° C. Extension reactions were quenched on ice, and then 5 μl aliquots were spotted immediately onto DE81 ion-exchange filters (2.3 cm; Whatman #3658323). Unincorporated [$^3$H] TTP was removed by 6 washes with 2×SCC (0.3M NaCl, 30 mM sodium citrate, pH 7.0), followed by a brief wash with 100% ethanol. Incorporated radioactivity was measured by scintillation counting. Reactions that lacked enzyme were also set up along with sample incubations to determine "total cpms" (omit filter wash steps) and "minimum cpms" (wash filters as above).

Cpms bound is proportional to amount of polymerase activity present per volume of bacterial extract. The volume of bacterial extract (0.25–1 μl) which brought about incorporation of approximately 10,000 cpms was determined for use in subsequent nucleotide analog incorporation testing.

P. Quantitating ddNTP Incorporation Efficiency

JDF-3 polymerase mutants were evaluated to assess relative ddNTP incorporation efficiency. Nucleotide incorporation was measured in the presence of varying concentrations of each ddNTP terminator (ddATP, ddCTP, ddGTP, and ddTTP). Since ddNTP incorporation produces non-extendable termini, polymerization is strongly inhibited for polymerases that incorporate ddNTPs efficiently. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

To measure incorporation of individual ddNTPs, cocktails were prepared which consisted of varying concentrations of the ddNTP of interest, and a total of 200 μM of each nucleotide triphosphate. For example, the incorporation of ddATP by wild type JDF-3 polymerase was measured at 0, 40, 80, 120 and 160 μM ddATP. In these reactions, dATP concentrations were adjusted to 200, 160, 120, 80, and 40 μM, respectively, so that the total amount of adenine nucleotide triphosphate was 200 μM. In comparison, mutants were assayed using ddATP concentrations of 0, 5, 10, and 20 μM ddATP, and adjusted dATP concentrations of 200, 195, 190, and 180 μM, respectively (dATP+ddATP=200 μM).

Additional cocktails were prepared to measure ddCTP, ddGTP, and ddTTP incorporation. To assess ddNTP incorporation by JDF-3 mutants at 3 different ddNTP concentrations, 12 reaction cocktails were prepared consisting of:

10 mM Tris-HCl, pH 8.8
1.5 mM MgCl$_2$
50 mM KCl
0.001% gelatin
5 μM [$^3$H]TTP (NEN #NET-221H, 20.5 Ci/mmole; partially evaporated to remove EtOH) 250 μg/ml of activated calf thymus DNA (e.g., Pharmacia #27-4575-01)

To each of 12 reaction cocktails was added the appropriate amounts of dNTPs and ddNTPs as summarized below:

| Cocktail | DGTP | dDATP | dCTP | TTP | ddGTP | ddATP | ddCTP | ddTTP |
|---|---|---|---|---|---|---|---|---|
| G-0 | 200 μM | 200 μM | 200 μM | 195 μM | 0 | 0 | 0 | 0 |
| G-5 | 195 μM | 200 μM | 200 μM | 195 μM | 5 | 0 | 0 | 0 |
| G-10 | 190 μM | 200 μM | 200 μM | 195 μM | 10 | 0 | 0 | 0 |
| G-20 | 180 μM | 200 μM | 200 μM | 195 μM | 20 | 0 | 0 | 0 |
| A-0 | 200 μM | 200 μM | 200 μM | 195 μM | 0 | 0 | 0 | 0 |
| A-5 | 200 μM | 195 μM | 200 μM | 195 μM | 0 | 5 | 0 | 0 |
| A-10 | 200 μM | 190 μM | 200 μM | 195 μM | 0 | 10 | 0 | 0 |
| A-20 | 200 μM | 180 μM | 200 μM | 195 μM | 0 | 20 | 0 | 0 |
| C-0 | 200 μM | 200 μM | 200 μM | 195 μM | 0 | 0 | 0 | 0 |
| C-5 | 200 μM | 200 μM | 195 μM | 195 μM | 0 | 0 | 5 | 0 |
| C-10 | 200 μM | 200 μM | 190 μM | 195 μM | 0 | 0 | 10 | 0 |
| C-20 | 200 μM | 200 μM | 180 μM | 195 μM | 0 | 0 | 20 | 0 |
| T-0 | 200 μM | 200 μM | 200 μM | 195 μM | 0 | 0 | 0 | 0 |
| T-5 | 200 μM | 200 μM | 200 μM | 190 μM | 0 | 0 | 0 | 5 |
| T-10 | 200 μM | 200 μM | 200 μM | 185 μM | 0 | 0 | 0 | 10 |
| T-20 | 200 μM | 200 μM | 200 μM | 175 μM | 0 | 0 | 0 | 20 |

Incorporation was measured by adding 1 μl of appropriately diluted bacterial extract (10,000 cpms) to 10 μl of each polymerase cocktail. Polymerization reactions were conducted for 30 minutes at 72° C. The extension reactions were counted as described above.

Reactions that lacked enzyme were also set up along with sample incubations to determine "minimum cpms"(wash filters as above). To determine % activity as a function of ddNTP concentration, background ("minimum cpms" value) was first subtracted from each of the sample cpms. "Total cpms", which are equivalent to 100% activity (0 ddNTPs), are determined by averaging the corrected cpms for the 4 reactions lacking ddNTPs (A-0, G-0, C-0, and T-0). Percent remaining activity was then calculated by dividing corrected sample cpms (with ddNTPs) by the corrected total cpms (average 0 ddNTPs).

Percent activity was plotted as a function of ddNTP concentration. $I_{50\%}$ values for each ddNTP (ddNTP concentration which inhibits nucleotide incorporation by 50%) were determined for each mutant. Comparisons allowed the identification of mutants with improved ddNTP incorporation relative to wild type JDF-3.

Initial studies used purified enzymes, and $I_{50\%}$ values were determined from inhibition plots employing 40–160 μM ddNTPs. The results in Table V show that mutants p8 (P41OL), p11 (P41OL), and p12(A485T) are inhibited by lower concentrations of ddNTPs than the parental exo$^-$ JDF-3 polymerase. Greater sensitivity indicates that the mutants incorporate all four ddNTPs more efficiently than the original JDF-3 polymerase.

For enzymes which preferentially incorporate TTP over ddTTP (exo$^-$ JDF-3, exo$^-$ Pfu), the use of increasingly higher concentrations of ddTTP (80–160 μM) and correspondingly lower concentrations of TTP (115–35 μM), in combination with a constant amount of [$^3$H]TTP (5 μM), leads to an increase in cpms incorporated with increasing ddNTP concentration. Therefore, in these initial experiments (where ddTTP>120 μM), $I_{50\%}$ values for TTP are artificially high. While they can be used to compare ddTTP incorporation among different polymerase mutants, they can not be used to assess reduced/enhanced preference for ddTTP relative to ddCTP, ddGTP, or ddATP.

TABLE V $I_{50\%}$ Values for Purified JDF-3 and JDF-3 Mutants.

| Purified Polymerase | Primary Mutation | $I_{50\%}$ Values (μM) ddATP | ddGTP | ddCTP | ddTTP |
|---|---|---|---|---|---|
| Exo$^-$ JDF-3 | — | 160 | 110 | >160 | >>160 |
| Exo$^-$ Pfu | — | >160 | >160 | >160 | >>160 |
| JDF-3 mutant p8 | P410L | 30 | 25 | 40 | 40 |
| JDF-3 mutant p11 | P410L | 30 | 30 | 60 | >160 |
| JDF-3 mutant p12 | A485T | 40 | 25 | 25 | 150 |

To allow a larger number of mutant clones to be screened, subsequent experiments employed bacterial extracts containing JDF-3 polymerase mutants. In addition, sensitivity was improved by using lower concentrations of each ddNTP inhibitor (5–20 μM). The results in Table VI demonstrate that all of the mutants selected from the primary filter screen exhibited improved incorporation of ddNTPs. Improvements in ddNTP incorporation were as high as >20-fold. All of the mutants containing a mutation at amino acid 408 (L408H/F), 410 (P410L), or 485 (A485T) (referred to as the "primary mutation") exhibited reduced discrimination against all four ddNTPs. Most, but not all, mutants with the L408H/F primary mutation produced very similar $I_{50\%}$ values (<2-fold difference) for all four ddNTPs, indicating that base selectivity is diminished or absent.

TABLE VI $I_{50\%}$ Values for JDF-3 Mutants (Bacterial Extracts).

| JDF-3 mutant clones | Primary mutation | $I_{50\%}$ Values (µM) | | | |
|---|---|---|---|---|---|
| | | ddATP | ddGTP | ddCTP | ddTTP |
| Exo⁻ JDF-3 | — | >80 | >80 | >80 | >80 |
| 1-1, 1-4, 1-18 | L408H | 8 to >20 | 4 to 5 | 6 to 13 | 5.5. to 10 |
| 1-25, 1-28, 1-29, 1-17 | L408F | 4.5 to >20 | 3.5 to 10 | 4 to 6.5 | 4 to 8 |
| p8 | P410L | 18.5 | 12 | 9.5 | >20 |
| 1-5, 1-6, 1-17 | P410L | 10 to >20 | 3.5 to 9 | 16.5 to >20 | 11 to >20<br>5 to >20 |
| 1-41, 1-38, 1-37, 1-3, 1-19, 1-30, 1-27, 1, 20 1-26, 1-32, 1-16, 1-12 | Not determined | 7 to >20 | 3.5 to 12 | 4 to >20 | |

Q. Sequencing with Purified JDF-3 Polymerase Mutants i. Sequencing with radioactively labeled dideoxynucleotides 1 to 2 µl of purified enzyme was substituted into the Thermo Sequenase radiolabeled terminator cycle sequencing kit (Amersham-Pharmacia #US79750). The samples were processed according to the manufacturer's instructions using the control primer and template provided with the kit. Three microliters of each sequencing reaction were loaded onto a 6% acylamide-7M urea, 1× TBE CASTAWAY™ Precast gel (Stratagene catalog #s 401090 and 401094). When the bromophenol blue indicator dye reached the end of the gel, the gel was fixed, dried and exposed to film for 24–72 hours (FIG. 6).

Figure 6:
FIG. 6 shows $^{33}$P-ddNTP cycle sequencing reactions performed using JDF-3 polymerase mutants. Purified JDF-3 mutants were substituted into the Thermo Sequenase radiolabeled terminator cycle sequencing kit. DNA sequencing ladders were generated as per the kit's instructions using the following polymerases: (A) Thermo Sequenase (B) JDF-3 #550 clone (parental) (C) JDF-3 A485T mutant (clone p12) (D) JDF-3 P410L mutant (clone p11) (E) JDF-3 P410L mutant (clone p8). The top of the original sequencing gel is shown on the side. The lanes are: (bottom) ddGTP, ddATP, ddTTP, ddCTP (top). Clones p8, p11, and p12 contain ancillary mutations and an amino-terminal tag.

The results in FIG. 6 show that clones p11 (panel D) and p8 (panel E) exhibit a dramatic improvement in the incorporation of all four ddNTPs compared to the parental #550 clone (panel B). Mutants p11 and p8 both contain the primary P410L mutation and an amino tag, but differ with respect to the number and types of ancillary mutations. Mutant p12 (panel C) produced a faint sequencing ladder, presumably due to the use of an insufficient amount of enzyme or the presence of ancillary mutations which reduce thermal stability. There is evidence of termination products in all lanes, suggesting an improvement in the incorporation of all four ddNTPs relative to the parental clone. Mutant p12 contains the primary mutation A485T in addition to ancillary mutations. In contrast to JDF-3 mutants identified here, the parental clone shows a strong preference to incorporate ddGTP, as evidenced both in primer extension (FIG. 6) and ddNTP inhibition assays (Tables V and VI).

ii. Sequencing with a radioactively labeled primer and fluorescent dideoxynucleotides Different DNA polymerases and polymerase mutants will exhibit varying degrees of discrimination against the dye moieties on the dideoxynucleotide analogs. An assessment of usage of dye-labeled dideoxynucleotide analogs by the JDF-3 polymerase mutants was carried out. The procedure used was as follows:

a. Primer Labeling

The sequencing primer SK was radioactively labeled with the KINACE-IT™ Kinasing Kit (Stratagene catalog #200390). The incubation reaction (40 µl) contained the following components:

1× kinase buffer #1
0.75 µCi/µl γ-³³P ATP
0.375 u/µl T4 polynucleotide kinase
2.5 pmol/µl SK primer The reaction was incubated at 37° C. for 45 minutes. The primer was purified away from free nucleotides with a size exclusion matrix (NUC TRAP® Stratagene catalog number 400701).

b. Dye labeled-dideoxynucleotide: dNTP ratios

Fluorescent dideoxynucleotides were purchased from New England Nuclear (NEN):

| | |
|---|---|
| R6G-ddATP | NEN catalog number NEL-490 |
| R110-ddTP | NEN catalog number NEL-495 |
| TAMRA-ddUTP | NEN catalog number NEL-472 |
| ROX-ddCTP | NEN catalog number NEL-477 |

Incorporation was measured using 3 different concentrations of dye labeled dideoxynucleotides (ddNTPs) and a constant amount of deoxynucleotides (dNTPs; 2.14 µM):

Condition 3) 1:1     (2–14 µM each dNTP:2.14 µM dye-labeled ddNTP)
Condition 2) 1:0.1     (2.14 µM each dNTP:0.214 µM dye-labeled ddNTP)
Condition 1) 1:0.01     (2.14 µM each dNTP:0.0214 µM dye-labeled ddNTP)

c. Preparation of the DNA Sequencing Reaction Mixtures

Four polymerases were tested for utilization of dye-labeled ddNTPs, exo⁻ JDF-3 (#550 clone), Thermo Sequenase (4 u/µl), JDF-3 P410L (clone p8 with ancillary mutations and an amino-terminal tag) and JDF-3 L408H (clone 1-1). A mixture containing the following reagents was assembled:

13.7 µl H₂O
1 µl labeled SK primer (2 pmol/µl)
1 µl pBluescript KS (0.2 µg/µl)
1 µl polymerase (~1.5 u/µl)
2 µl 10× buffer (reaction buffer 1 for all but L408H which uses 1.5 mM MgCl₂ buffer (see below)
10× Reaction Buffer 1
260 mM Tris pH 9.5
65 mM MgCl₂
10× 1.5 mM MgCl₂ buffer
24 mM MgCl₂
260 mM Tris pH 9.5

2.5 µl of each dye-labeled ddNTP terminator (ddGTP, ddATP, ddTTP and ddGTP was aliquotted separately into one of four tubes. 4.5 µl of each polymerase reaction was added to each of the four tubes, to give a final reaction volume of 7 µl.

d. Cycle Sequencing Reactions

The samples were cycled in a RoboCycler®96 Temperature Cycler with a Hot Top Assembly (Stratagene Catalog #400870 and #400894) using the following conditions:
1) 1 minute at 95° C.
2) 1 minute at 95° C.
3) 1 minute at 50° C.
4) 2 minutes at 72° C.
5) Repeat steps 2–4 thirty times.

4 µl of stop solution (95% formamide, 20 mM EDTA, 0.05% bromophenol blue, 0.05% xylene cyanol FF) was added to each of the amplified reactions before heating them to 99° C. for five minutes. The samples were electrophoresed on a 6% CASTAWAY™ gel as described above. The gels were dried and then exposed to film for 72 hours (FIG. 7).

Figure 7:
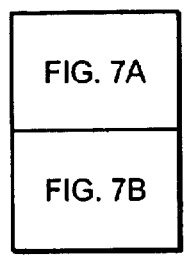
FIG. 7 shows cycle sequencing reactions performed using dye-labeled ddNTPs and JDF-3 polymerase mutants. DNA sequencing ladders were generated using (1) 2.14 $\mu$M dNTP: 0.0214 $\mu$M ddNTP; (2) 2.14 $\mu$M dNTP: 0.214 $\mu$M ddNTP; or (3) 2.14 $\mu$M dNTP: 2.14 $\mu$M ddNTP. The following purified DNA polymerases were used: (A) JDF-3 #550 clone (parental) (B) Thermo Sequenase (C) JDF-3 P410L mutant (clone p8, contains ancillary mutations and an amino tag) (E) JDF-3 L408H mutant (clone 1-1). The top of the original sequencing gel is shown on the right hand side.
Figure 7A:
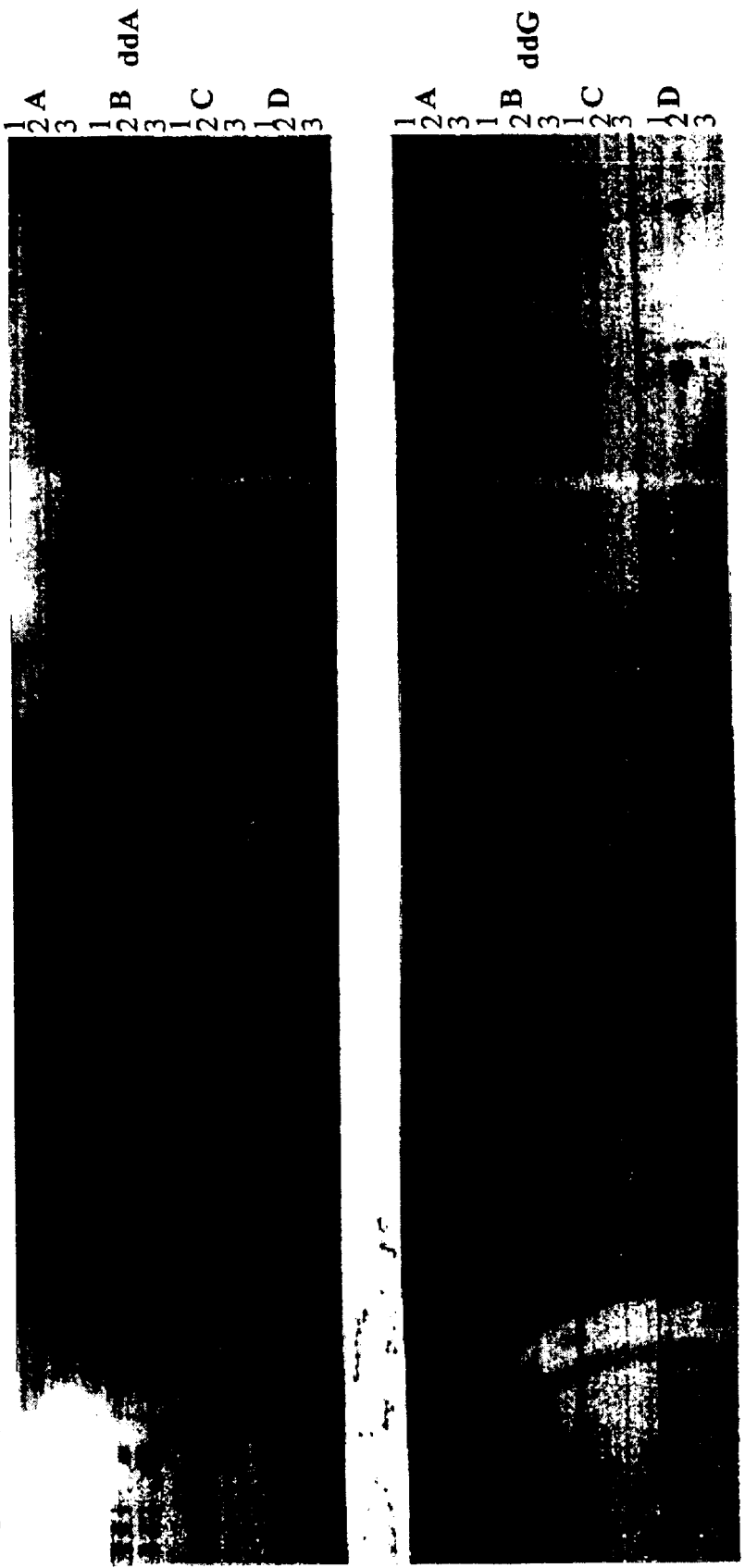
Figure 7B:
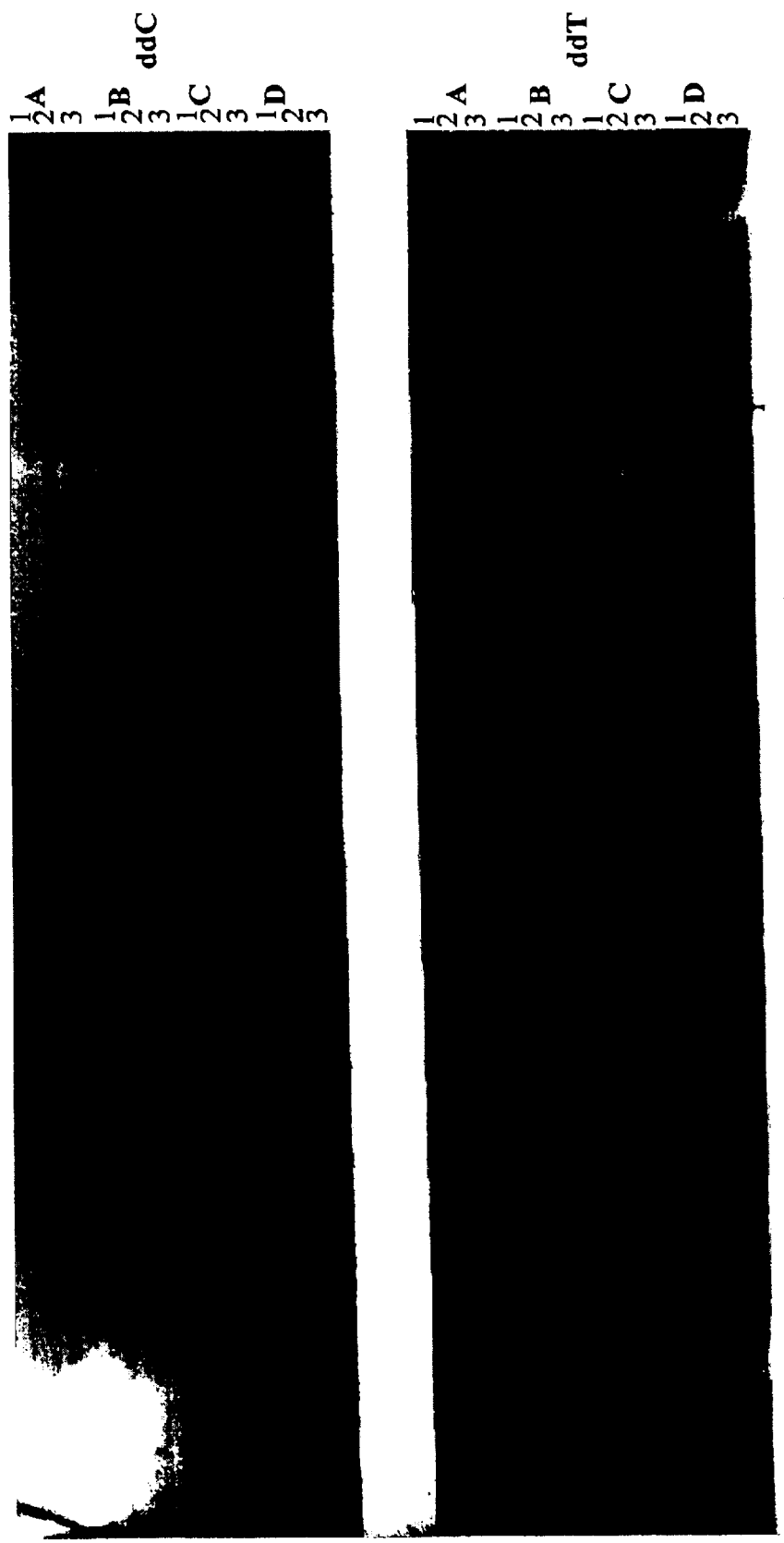

The results of studies designed to assess utilization of dye-labeled ddNTPs by the different polymerase clones are shown in FIG. 7. Clones p8 (panel C) and 1-1 (panel D) exhibited significantly improved incorporation of R6G-ddATP and R110-ddGTP, compared to the parental clone (panel A). Improvement was evidenced by the synthesis of sequencing ladders at 0.01× (1) and 0.1× (2) dye-ddNTP/dNTP ratios. Optimization of reaction conditions and/or dye moieties may be performed to realize improvements in the incorporation of ddTTP and ddCTP.

iii. Sequencing with double-mutant exo⁻ JDF-3 DNA polymerase.

To verify that changes at residues 408, 410, and 485 were sufficient to improve ddNTP incorporation, individual mutations were introduced into the parental 550 (JDF-3 exo⁻ DNA polymerase) clone by site-directed mutagenesis. In addition, point mutations were combined to examine whether they resulted in further improvements in dideoxynucleotide incorporation over polymerases bearing single mutations.

DNA sequencing reactions consisting of 1× reaction buffer, 0.15 pmol/µl long –20 primer, and 10 ng/µg pBluescript KS were prepared as follows:
81 µl H$_2$O
9 µl –20 long primer (2 pmol/µl)
6 µl pBluescript KS (0.2 µg/µl)
** µl polymerase
12 µl 10× buffer (260 mM Tris pH 9.5, 65 mM MgCl$_2$)

18 µl of the cocktail listed above was aliquotted into the appropriate number of tubes (one per polymerase). Each polymerase (2 µl) was added to an aliquot of cocktail and the tubes were mixed well. Each resulting polymerase mixture (4.5 µl) was then added to each of four tubes, already containing 0.06 mM of one of the four –$^{33}$P-dideoxynucleotides (ddATP, ddTTP, ddGTP or ddTTP; 1500 Ci/mmol; 450 µCi/ml) and 6 mM each deoxynucleotide in a volume of 2.5 µl.

The sequencing reactions were cycled in a ROBOCYCLER®96 temperature cycler with a Hot Top Assembly using the following conditions:
1) 1 minute at 95° C.
2) 45 seconds at 95° C.
3) 45 seconds at 60° C.
4) 1.5 minutes at 72° C.
5) Repeat steps 2–4 thirty times.

Stop solution (µl; 95% formamide, 20 mM EDTA, 0.05% bromophenol blue, 0.05% xylene cyanol FF) was added to each reaction before heating to 99° C. for five minutes. Each sample (4 µl) was loaded onto a 6% acrylamide denaturing CastAway gel. The gel was run and treated as described previously.

Figure 8:
FIG. 8 shows cycle sequencing reactions performed using the JDF-3 P410L/A485T double mutant and $\alpha$-$^{33}$P Dideoxynucleotides. DNA sequencing ladders were generated using the JDF-3 P410L/A485T double mutant at (A) 2 $\mu$l (B) 1 $\mu$l (C) 0.5 $\mu$l, the JDF-3 P410L mutant (clone p8, contains ancillary mutations and an amino-terminal tag) (D), or Thermo Sequenase (E). The top of the original sequencing gel is shown on the left side. The lanes are: (bottom) ddGTP, ddATP, ddTTP, ddCTP (top).

FIG. 8 shows that the P410L/A485T double mutant exhibits exceptionally even signals. Band uniformity was improved compared to mutant p8 (P410L mutation plus ancillary mutations that do not include A485T) and mutant A485T (data not shown). Mutant p8 exhibited a tendency to preferentially incorporate ddGTP and ddCTP in a sequence-dependent fashion. The optimal amount of enzyme may be higher than the quantity tested in this experiment. Sequence produced by the commercially available Family A DNA polymerase mutant, Thermo Sequenase, is shown in panel E.

iv. Ribonucleotide incorporation by JDF-3 polymerase mutants.

A primer annealed to single stranded DNA template was extended in a mixture containing all ribonucleotides or all deoxynucleotides with the mutant and progenitor polymerases.

M13mp18+ single stranded DNA was annealed to 95× molar excess of the 38mer primer by heating the mixture to 95° C. and cooling slowly at room temperature.

38mer primer: 5'GGTTTCCCAGTCACGACGTTG-TAAAACGACGGCCAGT 3' (SEQ ID NO: 18)

Preliminary assays were carried out to determine what dilutions of enzyme would be necessary to examine the incorporation activity at non-maximal levels. The final assay solutions were composed as described below:

| Ribonucleotide mixture | |
|---|---|
| 20 ng/µl | annealed primer/template |
| 1× | Cloned Pfu buffer (Stratagene catalog #200532) |
| 200 µM | each GTP, UTP, ATP |
| 50 µM | CTP |
| 1 µM | 5-$^3$H CTP 20.2 Ci/mmole |
| 0.05–0.3 units | JDF-3 polymerase* |
| Deoxyribonucleotide mixture | |
| 20 ng/µl | annealed primer template |
| 1× | Cloned Pfu buffer |
| 200 µM | each dGTP, dATP, dCTP |
| 50 µM | TTP (deoxyribonucleotide) |
| 1 µM | Thymidine 5'-triphosphate, [methyl-$^3$H] 20.5 Ci/mmole |
| 0.05–0.3 units | JDF-3 polymerase* |

*Added separately

Nine microliters of the polymerase-free mixtures were placed in 0.2 ml tubes before the polymerases were added. The samples were incubated at 72° C. in a ROBOCYCLER®96 temperature cycler with Hot Top Assembly (Stratagene Catalog Nos. 400870 and 400894). The deoxyribonucleotide mixture was removed at 2. minutes and placed at approximately 2° C. The ribonucleotide mixture was incubated for 30 minutes. Seven microliters of the assay mixture were spotted onto DE81 filter circles (Whatmann) and dried prior to being washed three times in 2× SSC (0.3M NaCl, 0.03M sodium citrate) for five minutes each wash. The filters were rinsed twice in ethanol and allowed to dry before being quantified with a scintillation counter.

Figure 9:
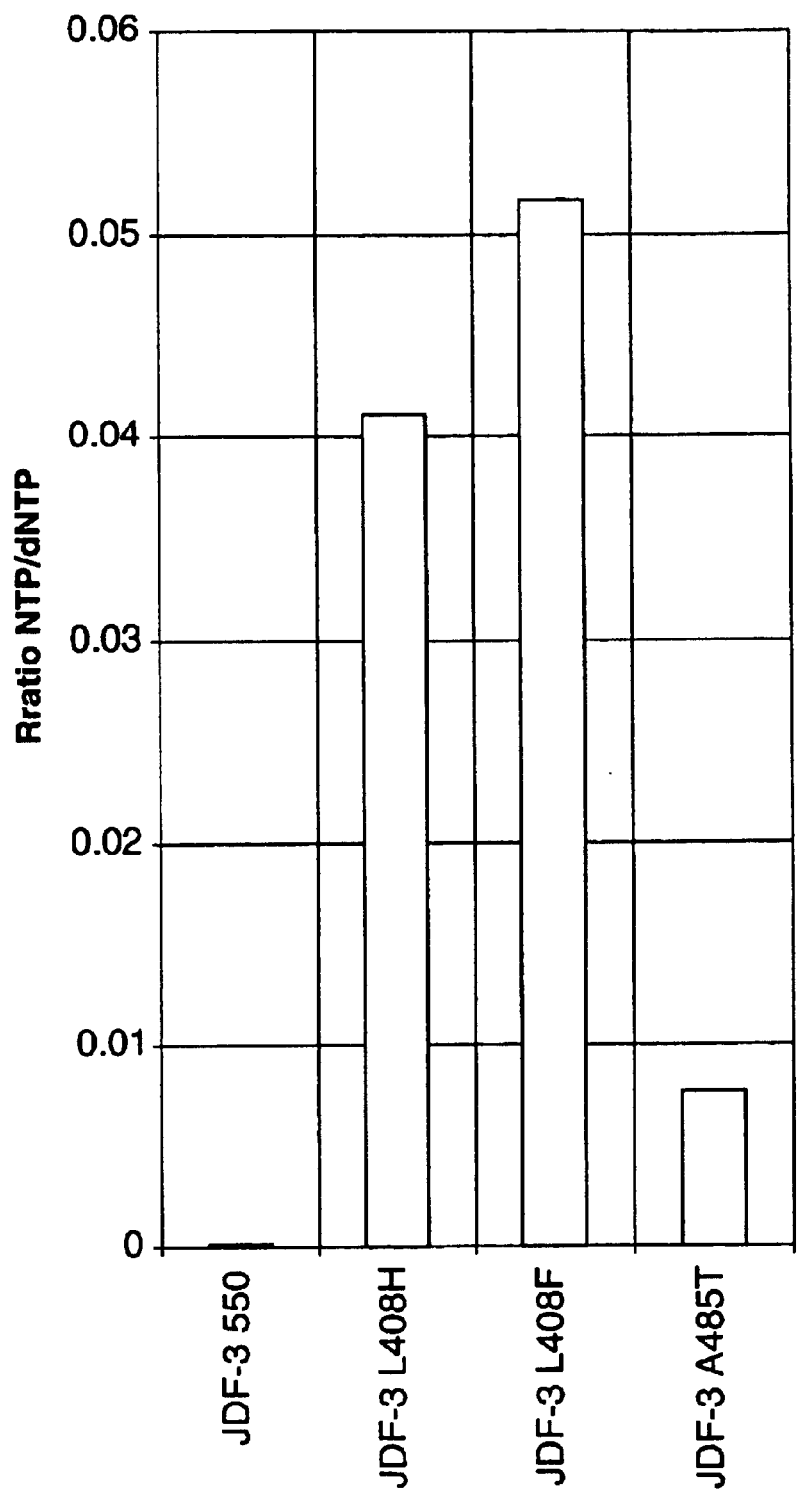
FIG. 9 shows the result of ribonucleotide incorporation assays using exo JDF-3 (550) and mutants of this progenitor clone. The ratios of ribonucleotide versus deoxynucleotide incorporation are plotted for JDF-3 550, JDF-3 L408H, JDF-3 L408F and JDF-3 A485T.
Figure 10:
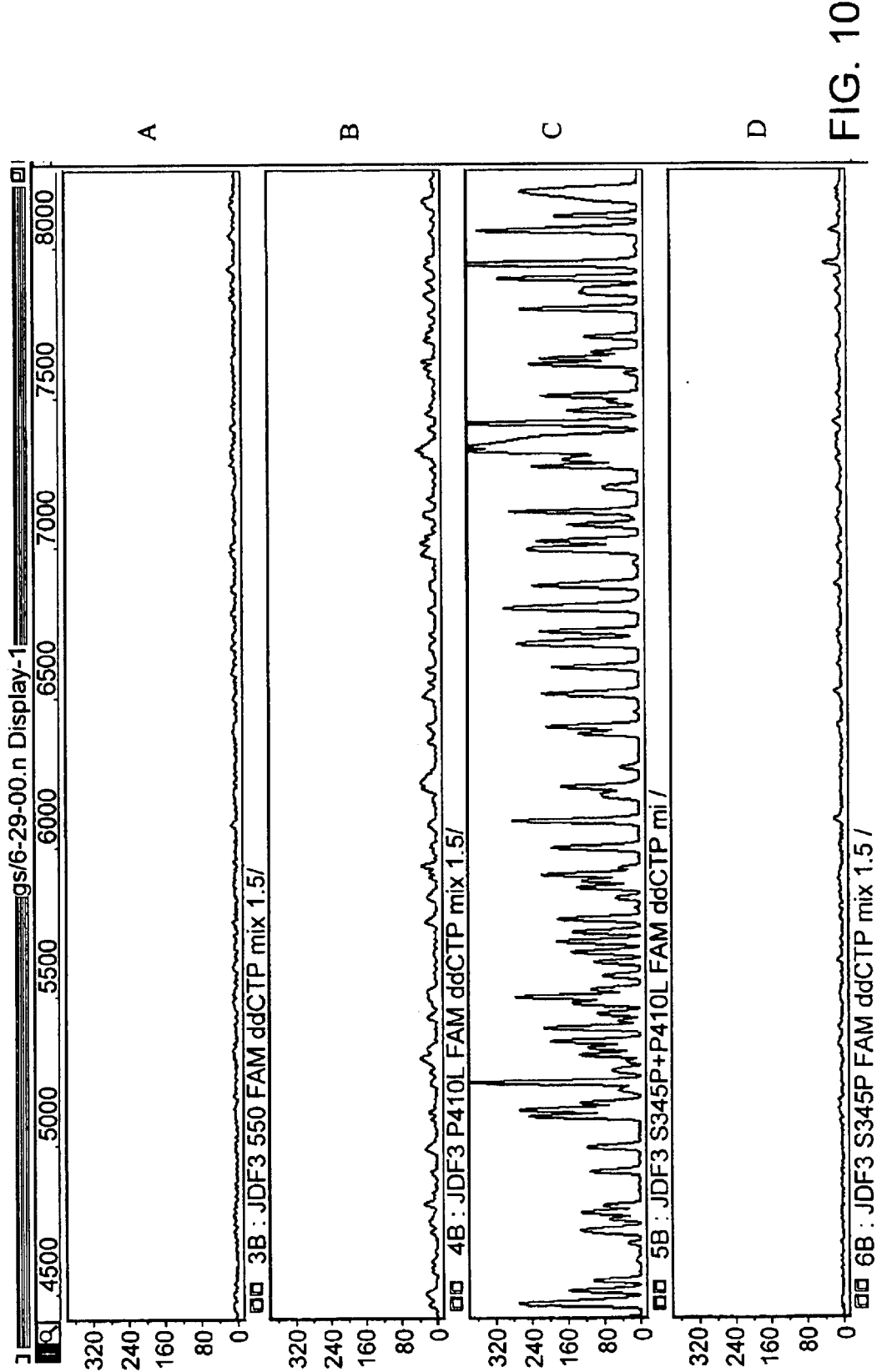
FIG. 10 shows the traces of the sequence generated by four versions of JDF-3 DNA polymerase and FAM ddCTP. Panel A shows the minimal trace produced by the progenitor polymerase JDF-3 550, Panel B demonstrates the slightly improved trace made by JDF-3 P410L, Panel C shows the sequence generated by the double mutant S345P and P410L, and Panel D shows the trace created by JDF-3 S345P.
Figure 11:
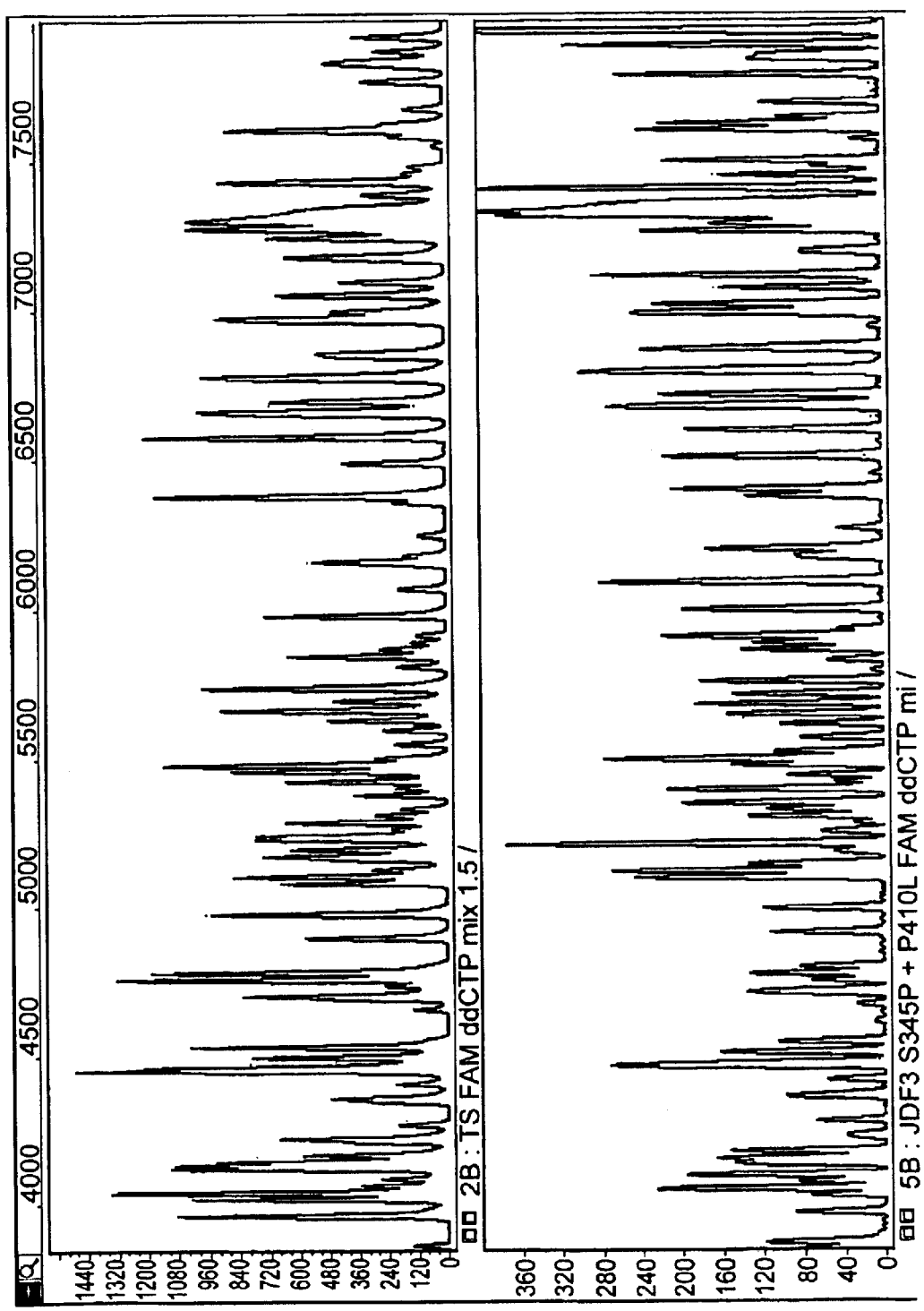
FIG. 11 shows the difference in peak uniformity demonstrated by Thermo Sequenase in Panel A and the double mutant JDF-3 S345P+P410L in Panel B.
Figure 12:
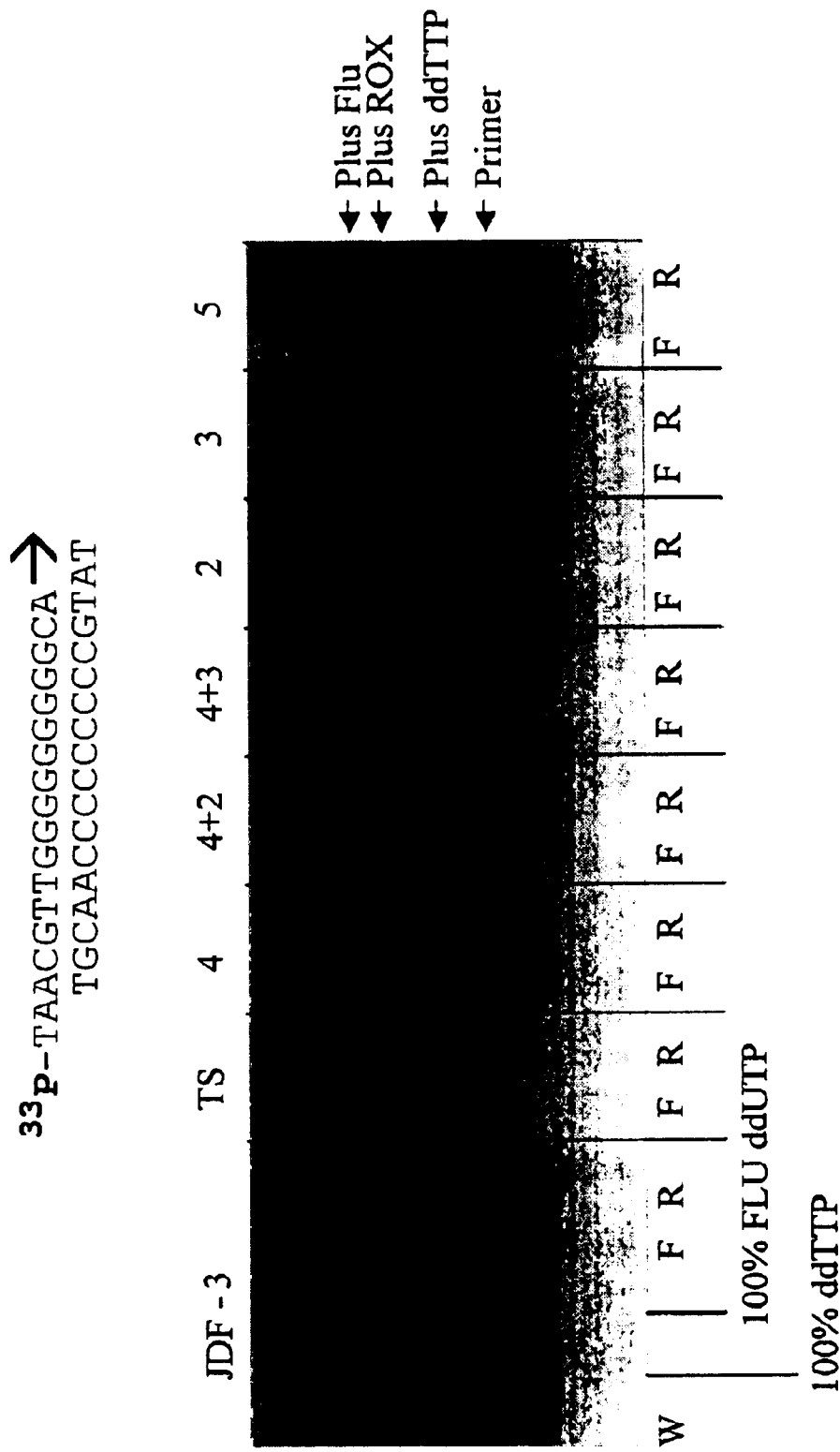
FIG. 12 shows the separated products of 3' extension of a labeled oligonucleotide (SEQ ID NOS: 18 and 19), with the dideoxynucleotide thymidine triphosphate of ROX-ddUTP (New England Nuclear (NEN) NEL476) or Fluorescein-12-ddUTP (NEN NEL401). Mutant 4 is JDF-3 S345P, Mutant 2 is JDF-3 P410L, Mutant 3 is JDF-3 A485T and Mutant 5 is Y496N. F indicates FLU ddUTP and R indicates ROX ddUTP.
Figure 13:
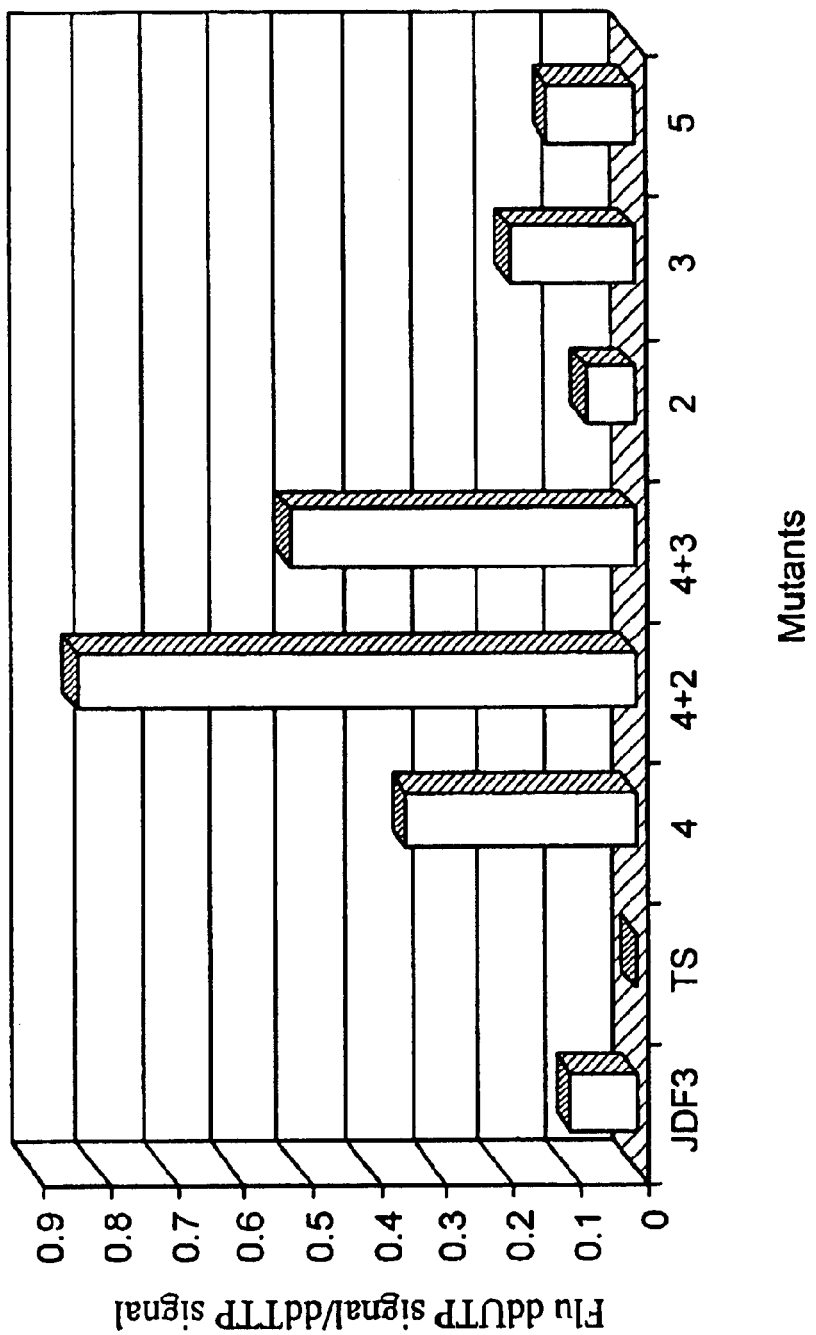
FIG. 13 shows a graphic representation of the relative band intensities from FIG. 12. The numerical values are generated by dividing the intensity value of the ddTTP band into the intensity value for the Fluroescein-12-ddUTP bands.

Background counts per minute (CPM) for the deoxyribonucleotide and the ribonucleotide reactions were subtracted from the respective averaged CPM value of duplicate samples for each enzyme. The background-corrected ribonucleotide CPM value was divided by the background-corrected deoxyribonucleotide CPM value (FIG. 9).

| Polymerase | Ratio NTP/dNTP | Relative to JDF-3 550 |
| --- | --- | --- |
| JDF-3 550 | 0.000165162 | 1 |
| JDF-3 L408H | 0.041087258 | 249 |
| JDF-3 L408F | 0.051703924 | 313 |
| JDF-3 A485T | 0.007628583 | 46 | v. Ribonucleotide sequencing with JDF-3 polymerase mutants.

Ribonucleotides incorporated into a deoxyribonucleotide polymer are susceptible to alkali hydrolysis which can produce a sub-population of polymer lengths. When labeled primer is extended in the presence of a particular ribonucleotide base (for example ATP) and the four deoxyribonucleotide bases, the fragments resulting from alkali hydrolysis create a population of different lengths, which correspond to all the possible positions where ATP was incorporated. When those fragments are size separated, their migration pattern, with respect to other ribonucleotide base (CTP, UTP and GTP) hydrolysis products allows the template sequence to be read. As described previously, most DNA polymerases discriminate against non-conventional deoxynucleotides. A subset of the JDF-3 DNA polymerase mutants which allow improved uptake of the unconventional dideoxynucleotides also show improved tolerance for ribonucleotide incorporation.

100 ng of the 38mer primer was kinased with $\gamma$-$^{33}$P according to the instructions in the KINACE-IT™ Kinasing Kit (Stratagene catalog #300390).

38mer primer: 5'GGTTTTCCCAGTCACGACGTTG-TAAAACGACGGCCAGT 3'(SEQ ID NO: 18)

The labeled oligonucleotide was purified from contaminating free nucleotides with a NUC TRAP® Probe Purification Column (Statagene catalog #400701) in 10T.1E (10 mM Tris pH 8.0, 0.1 mM EDTA). Labeled oligonucleotide (~7 picomoles) was annealed to 0.09 pmoles M13mp18+ by heating to 95° C. then cooling to room temperature in the presence of 0.32 mM MgCl$_2$.

| Extension components | |
| --- | --- |
| 0.054 pM | annealed primer/template |
| 200 □M | each dNTP |
| 1x cPfu | DNA polymerase buffer (Stratagene catalog #200532) |
| 4–200 | ATP* |
| 0.1–5 Units | JDF-3 polymerase* |

*Added separately

Eight microliters of a cocktail containing the first three components listed above were aliquoted into a 0.2 ml tube. 1 µl of polymerase and 1 µl of 2 mM, 0.2 mM or 0.4 mM ATP were added and the reaction was incubated at 72° C. for 15 minutes. The reaction volume was brought to 100 µl with 1x cPfu polymerase buffer and transferred to a 1.5 ml tube. After heating the reactions in the presence of 70 mM NaOH for 15 minutes at 100° C., the reaction was neutralized with 70 mM HCl and precipitated through the addition of 10 µl 3M sodium acetate and 327.5 µl of ethanol. The samples were microcentrifuged for 30 minutes at 14 krpm before the supernatant was removed and the pellet washed in 80% ethanol. After vacuum drying, the samples were resuspended in 5 µl of sequencing stop solution (95% formamide, 20 mM EDTA, 0.05% bromophenol blue, 0.05% xylene cyanol FF) and 2.5 µl was loaded on a 6% acylamide-7M urea, 1x TBE CASTAWAY™ Precast gel (Stratagene catalog numbers 401090 and 401094). The gels were run at 50 watts until the bromophenol blue dye migrated past the bottom of the gel after which the gel was fixed, dried and exposed to film for 72 hours.

Sequencing ladders for JDF-3 550 (wild-type nucleotide incorporation) and all the mutants tested were visible at the 200 µM and 20 µM ATP level. At the 4 µM level, only the L408H and L408F mutants produced ladders (data not shown).

vi. Sequencing with dye-dideoxynucleotide terminators

Primer was extended in the presence of FAM ddCTP (NENNEL481). The sequence reactions were purified and run on an ABI 370.

Reaction conditions for cycle-sequencing were as described below:

1x cPFU buffer, 200 ng pBluescript II KS plasmid, 3 pmole T7 primer, 0.23 mM dCTP, 0.23 mM dATP, 0.23 mM dTTP, 0.23 mM dGTP with 0.046 mM FAM ddCTP. The samples were cycled in a Perkin-Elmer cycler in 10 µl volumes for 25 cycles of the temperatures and times described below:

| | |
| --- | --- |
| 95° C. | 30 s |
| 55° C. | 30 s |
| 72° C. | 2 min |

The samples were purified using CentriSep columns according to the manufacturer's instructions. After drying, the samples were resuspended in 3 µl of a loading dye comprised of 66.7% deionized formamide, 16.7 mg/ml Blue Dextran, and 8.3 mM EDTA. Samples were heated at 95° C. for three minutes and loaded on a 5% LongRangen gel in an ABI PRISM 377 DNA sequencer.

Data was processed in Gene Scan 2.1.

Example 2

Labeling of DNA.

The modified DNA polymerases of the invention are applicable to labeling of DNA. It is known to those skilled in the art that there are several means by which to label DNA, including the incorporation of radiolabeled nucleotides. One such common means is by random priming, which enables one of skill in the art to generate labeled DNA fragments, typically about 50 to about 1000 bases long. The procedure described herein are adapted from F. Ausubel et al., Short Protocols in Molecular Biology, Third Edition, John Wiley and Sons, Inc., 1995.

As a first step toward random priming DNA, a reaction mix containing 2.5 microliters 0.5 mM 3dNTP (dCTP, dGTP, TTP, each at 0.5 mM), 50 µCi [-$^{32}$P]dATP, 1 microliter of 3 to 8 units/microliter DNA polymerase in 50 mM Tris-HCl, pH 7.5, 10 mM MgCl$_2$, 1 mM dithiothreitol, 0.05 mg/ml bovine serum albumin is prepared in a total volume of 11 microliters and incubated on ice. Next, about 30 to about 100 ng of DNA is mixed with about with 1 to 5 µg of random hexanucleotides in 14 microliters and boiled for 2 to 3 minutes and then placed on ice. The 11 microliter reaction mix is then added to the DNA/random hexamer mix, and the random priming reaction is incubated over 10 minutes to as much as 4 hours at room temperature. To stop the reaction, 1 microliter 0.5 M EDTA, 3 microliters 10 mg/ml tRNA, and 100 microliters 10 mM Tris-HCl, pH 7.4 is added and the mixture is extracted with phenol. The labeled DNA is then separated from unincorporated radioactive precursors by chromatography.

R. Gel Assay for Dye-dideoxynucleotide Incorporation

A labeled oligonucleotide duplex was extended with a mixture of dideoxynucleotides and dye-dideoxynucleotides. When the duplex was separated on a denaturing 20% Acrylamide/7 M urea gel, labeled oligonucleotides terminated with a dideoxynucleotide could be resolved from oligonucleotides terminated with dye-deoxynucleotides.

Oligonucleotides:

259C $^{32}$P-TAACGTTGGGGGGGGGCA→(SEQ ID NO: 19)

258C TGCAACCCCCCCCCGTAT (SEQ ID NO: 20)

The 5' end of 259C was labeled and purified as described in Section Q.ii.a except that $^{32}$Pγ-ATP was used. The labeled oligonucleotide 259C was at a concentration of approximately 0.7 ng/μl. The complimentary oligonucleotide (258C) was added as an equal concentration, heated to 95° C. for three minutes, 50° C. for 5 minutes and room temperature for 20 minutes. Heat killed lysates of the relevant mutants were prepared as described in Example section C. The reactions were incubated in a 5 μl volume composed of 30 mM Tris pH 8.0 and 3 mM MgCl$_2$ with a nucleotide mixture totaling 0.1 mM. The ratio of ddTTP to FLU ddUTP or ROXddUTP was 10:1. The dimer was present at a concentration of 1.2 picomoles and 0.5 μl of enzyme or crude lysate or purified enzyme was added to the reaction before incubation at 50° C. in the RobeCycler® Gradient 96 Temperature Cycler with Hot Top. The samples were incubated for 20 s before 3 μl of a formamide based loading dye was added and the samples were heat-denatured at 95° C. for 3 minutes then loaded onto a 20% acrylamide/7 M urea gel and subjected to electrophoresis at a constant 60 watts. The gel was exposed to X-ray film and the film was analyzed in the EagleEye® Eagle Sight software package.

References for Table I

1. Joyce, C. M., Kelley, W. S. and Grindley N. D. F. (1982) J. Biol. Chem. 257, 1958–1964.
2. Lopes, P. Martinez, S., Diaz, A. Espinosa, M. And Lacks, S. A. (1989) J. Biol. Chem. 264, 4255–4263.
3. Lawyer, F. C., Stoffel, S., Saiki, R. K., Myambo, K. Drummond, R. and Gelfand, D. H. (1989) J. Biol. Chem. 264, 6427–6437.
4. Akhmetzjanov, A. A. and Vakhitov, V. A. (1992) Nucl. Acids Res. 20, 5839.
5. Leavitt, M. C. and Ito, J. (1989) Proc. Acad. Sci. U.S.A. 86, 4465–4469.
6. Dunn, J. J. and Studier, F. W. (1983) J. Mol. Biol. 166, 477–535.
7. Scarlato, V. And Gargano, S. (1992) Gene 118, 109–113.
8. Ràdén, B. And Rutberg, L. (1984) J. Virol. 52, 9–15.
9. Foury, F. (1989) J. Biol. Chem. 264, 20552–20560.
10. Ito, J. And Braithwaite, D. K (1990) Nucl. Acids Res. 18, 6716.
11. Blanco, L. Bernad, A. And Salas, M. (1991) Nucl. Acids res. 19, 955.
12. Hahn, S. And Rüger, W, (1989) Nucl. Acids Res. 17, 6729.
13. Hollingsworth, H. C. and Nossal, N. G. (1991) J. Biol. Chem. 266, 1888–1897.
14. Kaliman, A. V., Krutilina, A. I., Kryukov, V. M. and Bayev, A. A. (1986) FEBS Lett. 195, 61–64.
15. Iwasaki, H. Ishino, Y., Toh, H. Nakata, A. and Shinagawa, H. (1991) Mol. Gen Genet. 226, 24–33.
16. Jung, G., Leavitt, M. C., Hsieh, J.-C. and Ito, J. (1987) Proc. Natl. Acad. Sci. U.S.A. 84, 8287–8291.
17. Savilahti, H. And Bamford D. H. (1987) Gene 57, 121–130.
18. Yoshikawa, H. And Ito, J. (1982) Gene 17, 323–335.
19. Matsumoto, K., Takano, H., Kim, C. I. and Hirokawa, H. (1989) Gene 84, 247–255.
20. Spicer, E. K., Rush, J. Fung, C., Reha-Krantz, L. J., Karam, J. D. and Konigsberg, W. H. (1988) J. Biol. Chem. 263, 7478–7486.
21. Perler, F. B., Comb, D. G., Jack, W. E., Moran, L. S., Qiang, B., Kucera, R. B., Benner, J., Slatko, B. E., Nwankwo, D. O., Hempstead, S. K., Carlow, C. K. S. and Jannasch, H. (1992) Proc. Natl. Acad. Sci. USA 89, 5577–5581.
22. Mathur, E. J., Adams, M. W., Callen, W. N. and Cline, J. M. (1991) Nucleic. Acids Res. 19, 6952.
23. Pisani, F. W., De Martino, C. and Rossi, M. (1992) Nucl. Acids Res. 20, 2711–2716.
24. Wong S., W. Wahl, A. F., Yuan, P.-M., Arai, N., Pearson, B. E., Arai, K, -i., Korn, D., Hunkapiller, M. W. and Wang, T. S.-F. (1988) EMBO J. 7, 37–47.
25. Pizzagalli, A., Valsasnini, P., Plevani, P. and Lucchini, G. (1988) Porc. Natl. Acad. Sci. U.S.A. 85, 3772–3776.
26. Damagnez, V., Tillit, J., deRecondo, A.-M. and Baldacci, G. (1991) Mol. Gen. Genet. 226, 182–189.
27. Hirose, F., Yamaguchi, M. Nishida, Y., Masutani, M., Miyazawa, H., Hanaoka, F. and Matsukage, A. (1991) Nucl. Acids Res. 19, 4991–4998.
28. Leegwater, P. A. J., Strating, M., Murphy, N. B., Kooy, R. F., van der Vliet, P. C. and Overdulve, J. P. (1991) Nucl. Acids Res. 19, 6441–6447.
29. Chung, D. W., Zhang, J., Tan C.-K., Davie, E. W., So, A. G. and Downey, K. M. (1991) Proc. Natl. Acad. Sci. USA 88, 11197–11201.
30. Yang, C.-L., Chang, L. S., Zhang, P., Hao, H., Zhu, L., Tommey, N. L. and Lee, M. Y. W. T. (1992) Nucl. Acids Res. 20, 735–745.
31. Zhang, J. Chung, D. W., Tan, C.-K., Downey, K. M., Davie, E. W. and So, A. G. (1991) Biochemistry 30, 11742–11750.
32. Morrison, A. and Sugino, A. (1992) Nucl. Acids Res. 20, 375.
33. Pignéde, G., Bouvier, D., deRecondo, A.-M. And Baldacci, G. (1991) J. Mol. Biol. 222, 209–218.
34. Ridley, R. G., White, J. H., McAleese, S. M., Gorman, M., Alano, P., deVies, E. and Kilbey, B. J. (1991) Nucl. Acids Res. 19, 6731–6736.
35. Morrison, A., Araki, H., Clark, A. B., Hamatake, R. K. and Sugino, A. (1990) Cell 62, 1143–1151.
36. Morrison, A., Christensen, R. B., Alley, J., Beck, A. K., Bernstine, E. G., Lemontt, J. F. and Lawrence, C. W. (1989) J. Bacteriol. 171, 5659–5667.
37. Gibbs, J. S., Chiou, H. C., Hall, J. D., Mount, D. W., Retondo, M. J., Weller, S. K. and Coen, D. M. (1985) Proc. Natl. Acad. Sci. U.S.A. 82, 7969–7973.
38. Telford, E. A., Watson, M. S., McBride, K. and Davison, A. J. (1992) Virology 189, 304–316.
39. Davison, A. J. and Scott, J. E. (1986) J. Gen. Virol. 67, 1759–1816.
40. Baer, R., Bankier, A. T. Biggin, M. D., Deininger, P. L., Farrell, P. J., Gibson, T. J., Hatfull, G., Hudson, G. S., Satchwell, S. C., Séguin, C., Tuffnell, P. S. and Barrell, B. G. (1984) Nature 310, 207–211.
41. Albrecht, J.-C. and Fleckenstein, B. (1990) Virology 174, 533–542.
42. Kouzarides, T. Bankier, A. T., Satchwell, S. C., Weston, K., Tomlinson, P. and Barrell, B. G. (1987) J. Virol, 61, 125–133.

43. Elliott, R., Clark, C. Jaquish, D. and Spector, D. H. (1991) Virology n185, 169–186.
44. Teo, I. A., Griffin, B. E. and Jones, M. D. (1991) J. Virol. 65, 4670–4680.
45. Davison, A. J. (1992) Virology 186, 9–14.
46. Grabherr, R., Strasser, P. and Van Etten, J. L. (1992) Virology 188, 721–731.
47. Binns, M. M., Stenzler, L. Tomley, F. M., Campbell, J. and Broursnell, M. E. G. (1 987) Nucl. Acids Res. 15, 6563–6573.
48. Earl P. L., Jones, E. V. and Moss, B. (1986) Prov. Natl. Acad. Sci. U.S.A. 83, 3659–3663.
49. Mustafa, A. And Yuen, L. (1991) DNA Seq. 2, 39–45.
50. Tomalski, M. D., Wu, J. and Miller, L. K. (1988) Virology 167, 591–600.
51. Bjornson, R. M. and Rohrmann, G. F. (1992) J. Gen. Virol 73, 1499–1504.
52. Gingeras, T. R., Sciaky, D., Gelinas, R. E., Bing-Dong, J., Yen, C. E., Kelly, M. M., Bullock, P. A. Parsons, B. L., O'Neill. K. E. and Roberts, R. J. (1982) J. Biol. Chem, 257, 13475–13491.
53. Engler, J. A., Hoppe, M. S. and van Bree, M. P. (1983) Gene 21, 145–159.
54. Shu, L., Hing, J. S., Wei, Y.-f. and Engler, J. A., (1986) Gene 46, 187–195.
55. Paillard, M., Sederoff, R. R. and Levings, C. S. III (1985) EMBRO J. 4, 1125–1128.
56. Chan, B. S.-S., Court, D. A., Vierula, P. J. and Bertrand, H. (1991) Curr. Genet. 20, 225–237.
57. Kempken, F., Meinhardt, F. and Esser, K. (1989) Mol. Gen. Genet, 218, 623–530.
58. Oester, B. And Tudzynski, P. (1989) Mol. Gen. Genet. 217, 132–140.
59. Court D. A. and Bertrand, H. (1992) Curr. Genet. 22, 385–397.
60. Robison, M. M., Royer, J. C. and Horgen, P. A. (1991) Curr. Genet. 19, 495–502.
61. Stark, M. J. R., Mileham, A. J., Romanos, M. A. and Boyd, A. (1994) Nucl. Acids Res. 12, 6011–6030.
62. Tommasino, M. Ricci, S. and Galeotti, C. L. (1988) Nucl. Acids Res. 16, 5863–5878.
63. Hishinuma, F. and Hirai, K. (1991) J. Gen. Genet. 226, 97–106.
64. Hopfner, K. P. et al. (1999) Proc. Natl. Acad. Sci. U.S.A. 96, 3600–3605.
65. Niehaus, F. et al. (1997) Gene 204, 153–158.
66. Tagaki et al. (1997) Appl. Environ. Microbiol. 63, 4504–4510.
67. Datukishvili, N. et al. (1996) Gene 177, 271–273.
68. Southworth, M. W. et al. (1996) Proc. Natl. Acad. Sci. U.S.A. 93, 5281–5285.
69. Uemori, T. et al. (1995) J. Bacteriol. 177, 2164–2177.
70. Konisky, J. et al. (1994) J. Bacteriol. 176, 6402–6403.
71. Zhao (1999) Structure Fold Des. 7, 1189.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A purified thermostable DNA polymerase having an amino acid sequence presented in SEQ ID NO: 2 from residue 1 to 776.

2. An isolated recombinant polypeptide comprising the amino acid sequence of SEQ ID NO: 2.

3. An isolated recombinant JDF-3 DNA polymerase comprising a sequence of SEQ ID NO: 2 and further comprising a mutation at D141 and/or E143 within said sequence of SEQ ID NO: 2.

4. The isolated recombinant JDF-3 DNA polymerase of claim 3, wherein said mutation at D141 is an aspartic acid (D) to threonine (T) or alanine (A) mutation, and said mutation at E143 is a glutamic acid (E) to alanine (A) mutation.

5. The isolated recombinant JDF-3 DNA polymerase of claim 3 or 4, further comprising a mutation at L408 and/or P410.

6. The isolated recombinant JDF-3 DNA polymerase of claim 5, wherein said mutation at L408 is a leucine (L) to histidine (H) or phenylalanine (F) mutation and said mutation at P410 is a proline (P) to leucine (L) mutation.

7. The isolated recombinant JDF-3 DNA polymerase of claim 3 or 4, further comprising a mutation at one or more additional amino acids selected from the group consisting of: A485, S345, T604, Y497, I630, E645, E578, R465, V401, N424, P569. E617. V640, S651, L396, E459, L456, E658, V437, L478, Y496, Y409 and A490 within the sequence of SEQ ID NO: 2.

8. The isolated recombinant JDF-3 DNA polymerase of claim 7, wherein said mutation at S345 is serine (S) to proline (P), said mutation at A485 is alanine (A) to threonine (T), cysteine (C), serine (S), leucine (L), isoleucine (I), phenylalanine (F) or valine (V), said mutation at Y497 is tyrosine (Y) to cysteine (C), said mutation at I630 is isoleucine (I) to valine (V), said mutation at E645 is glutamic acid (E) to lysine (L), said mutation at E578 is glutamic acid (E) to lysine (L), said mutation at R465 is arginine (R) to methionine (M), said mutation at L396 is leucine (L) to glutamine (Q) or to proline (P), said mutation at S651 is serine (S) to asparagine (B), said mutation at L456 is leucine (L) to histidine (H), said mutation at Y496 is tyrosine (Y) to asparagine (B) or leucine (L), said mutation at Y409 is tyrosine (Y) to valine (V), said mutation at A490 is alanine (A) to tyrosine (Y).

9. The isolated recombinant JDF-3 DNA polymerase of claim 3 or 4, wherein said JDF-3 DNA polymerase has reduced discrimination against a non-conventional nucleotide selected from the group consisting of: dideoxynucleotides, ribonucleotides and conjugated nucleotides.

10. The isolated recombinant JDF-3 DNA polymerase of claim 9, wherein said conjugated nucleotide is selected from the group consisting of radiolabeled nucleotides, fluorescently labeled nucleotides, biotin labeled nucleotides, chemiluminescently labeled nucleotides and quantum dot labeled nucleotides.

11. An isolated JDF-3 DNA polymerase comprising a sequence of SEQ ID NO: 2 and further comprising the following mutations: D141T or D141A, E143A, L408H or L408F, P410L, and A485T within said SEQ ID NO: 2.

12. An isolated JDF-3 DNA polymerase comprising a sequence of SEQ ID NO: 2 and further comprising the following mutations: D141T or D141A and E143A within said SEQ ID NO: 2.

13. An isolated JDF-3 DNA polymerase comprising a sequence of SEQ ID NO: 2 and further comprising the following mutations: D141T or D141A and E143A, and further comprising one or more mutations selected from the group consisting of: L408H or L408F, P410L, and S345P within said SEQ ID NO: 2.

14. An isolated JDF-3 DNA polymerase comprising a sequence of SEQ ID NO: 2 and further comprising mutations at: D141, E143, P410, and A485 within said SEQ ID NO: 2.

15. An isolated JDF-3 DNA polymerase comprising a sequence of SEQ ID NO: 2 and further comprising the following mutations of: D141T or D141A, E143A, P410L, and A485T within said SEQ ID NO: 2.

16. A kit comprising an isolated recombinant polypeptide of claim 2, and packaging material thereof.

17. A kit comprising an isolated recombinant DNA polymerase of claim 3 or 4, and packaging material thereof.

18. A kit comprising an isolated recombinant DNA polymerase of claim 5, and packaging material thereof.

19. A kit comprising an isolated recombinant DNA polymerase of claim 6, and packaging material thereof.

20. A kit comprising an isolated recombinant DNA polymerase of claim 7, and packaging material thereof.

21. A kit comprising an isolated recombinant DNA polymerase of claim 8, and packaging material thereof.

22. A method of making a purified thermostable DNA polymerase of claim 1, comprising a) transfecting a host cell with the nucleic acid sequence presented in SEQ ID NO: 1, and b) culturing said host cell under conditions which permit production of said DNA polymerase.

23. The method of claim 22, wherein said host cell is *E. Coli* or *Thermococcus*.

24. A method of making a purified thermostable DNA polymerase of claim 3 or 4, comprising a) transfecting a host cell with a nucleic acid sequence encoding said polymerase and b) culturing said host cell under conditions which permit production of said DNA polymerase.

25. The method of claim 24, wherein said host cell is *E. Coli* or *Thermococcus*.

\* \* \* \* \*